(12) United States Patent  (10) Patent No.: US 8,872,653 B2
Okuno  (45) Date of Patent: Oct. 28, 2014

(54) DISPLAY CONTROL DEVICE

(75) Inventor: Hiroki Okuno, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 294 days.

(21) Appl. No.: 13/392,471

(22) PCT Filed: Aug. 17, 2010

(86) PCT No.: PCT/JP2010/063868
§ 371 (c)(1),
(2), (4) Date: Feb. 24, 2012

(87) PCT Pub. No.: WO2011/024672
PCT Pub. Date: Mar. 3, 2011

(65) Prior Publication Data
US 2012/0154348 A1    Jun. 21, 2012

(30) Foreign Application Priority Data

Aug. 27, 2009  (JP) .................................. 2009-196932
Aug. 27, 2009  (JP) .................................. 2009-196933

(51) Int. Cl.
*G08B 1/08*    (2006.01)

(52) U.S. Cl.
USPC ................ 340/539.26; 340/539.1; 340/573.1; 435/39; 435/287.1

(58) Field of Classification Search
USPC ......... 340/539.26, 539.1, 573.1, 603; 435/29, 435/39, 287.1, 288.3, 288.5, 288.7, 204, 435/287.3, 287.5, 287.7; 702/5, 19, 21
See application file for complete search history.

(56) References Cited

U.S. PATENT DOCUMENTS

| | | | |
|---|---|---|---|
| 7,532,314 B1 * | 5/2009 | Black et al. | ..................... 356/73 |
| 7,582,473 B2 * | 9/2009 | Kawashima | ................ 435/288.7 |
| 2007/0013910 A1 | 1/2007 | Jiang et al. | |
| 2008/0138841 A1 * | 6/2008 | Vegvary et al. | ............... 435/7.32 |
| 2008/0241875 A1 * | 10/2008 | Hwang et al. | ................... 435/39 |

FOREIGN PATENT DOCUMENTS

| | | |
|---|---|---|
| JP | 11-166754 A | 6/1999 |
| JP | 2000-283533 A | 10/2000 |
| JP | 2002-22503 A | 1/2002 |
| JP | 2003-38163 A | 2/2003 |

(Continued)

OTHER PUBLICATIONS

The Government of the Hong Kong Special Administrative Region, "A Guide on Indoor Air Quality Certification Scheme for Offices and Public Places", The Government of Hong Kong, Sep. 1, 2003, XP055051106, 35 pages.

*Primary Examiner* — Hung T. Nguyen
(74) *Attorney, Agent, or Firm* — Birch, Stewart, Kolasch & Birch, LLP

(57) ABSTRACT

An air purifier includes a detection apparatus, calculates a relative value of the number of microorganisms detected from airborne particles by the detection apparatus to a prescribed total value, and determines a central angle α corresponding to the relative value. Further, regarding the number of airborne particles other than microorganisms detected by the detection apparatus as the number of dusts, relative value of dust particles to a prescribed total value is calculated, and the central angle β corresponding to the relative value is determined. On a display panel, the amount of microorganisms is displayed as a bacteria meter by the area from the start position to the angle α, and by the following area to the angle β, the number of dusts is displayed as a dust meter, in a circle graph.

12 Claims, 55 Drawing Sheets

(56) References Cited

FOREIGN PATENT DOCUMENTS

| | | |
|---|---|---|
| JP | 2008-508527 A | 3/2008 |
| JP | 2010-19430 A | 1/2010 |
| WO | WO 99/37383 A1 | 7/1999 |
| WO | WO 2008/105893 A2 | 9/2008 |
| WO | WO 2011/104770 A1 | 9/2011 |

* cited by examiner

FIG.35

| CONDITION | MESSAGE |
|---|---|
| 1-1 | "ROOM AIR POLLUTED" |
| 1-2 | "PURIFY AIR IMMEDIATELY" |
| 2 | "MOLD DEVELOPMENT PROBABLE" |
| 3-1 | "RISK OF MOLD DEVELOPMENT ELEVATED" |
| 3-2 | "RISK OF MOLD DEVELOPMENT ELEVATED" |
| 4 | "RISK OF MOLD DEVELOPMENT ELEVATED" |
| 5-1 | "WATCH OUT FOR CONTAGIOUS COLD" |
| 5-2 | "WATCH OUT FOR FLU" |
| 6-1 | "WATCH OUT FOR ...COLD" |
| 6-2 | "FLU ALARM" |
| 7-1 | "MOLD DEVELOPMENT PROBABLE" "WATCH OUT FOR SUMMER COLD" |
| 7-2 | "WATCH OUT FOR SUMMER COLD" |
| 8 | "TAKE CARE TO PREVENT DRY THROAT" "WATCH OUT FOR COLD" |
| 9 | "TAKE CARE TO PREVENT DRY THROAT" |
| 10 | "MOLD DEVELOPMENT PROBABLE" |
| 11-1 | "WATCH OUT FOR ...COLD" |
| 11-2 | "WATCH OUT FOR FLU" |
| 12-1 | "CLEAN ENVIRONMENT" |
| 12-2 | "VERY CLEAN ENVIRONMENT" |

- ROOM AIR POLLUTED
- WATCH OUT FOR ALLERGIES
- RUN AIR PURIFIER

- PURIFY AIR IMMEDIATELY

- MOLD DEVELOPMENT PROBABLE
- DEHUMIDIFY/REMOVE BACTERIA

- RISK OF MOLD DEVELOPMENT ELEVATED
- DEHUMIDIFY/REMOVE BACTERIA

- WATCH OUT FOR FLU
- WASH YOUR HANDS AND GARGLE

- FLU ALARM
- IMMEDIATELY HUMIDIFY/REMOVE BACTERIA
- TARGET HUMIDITY 55~65%

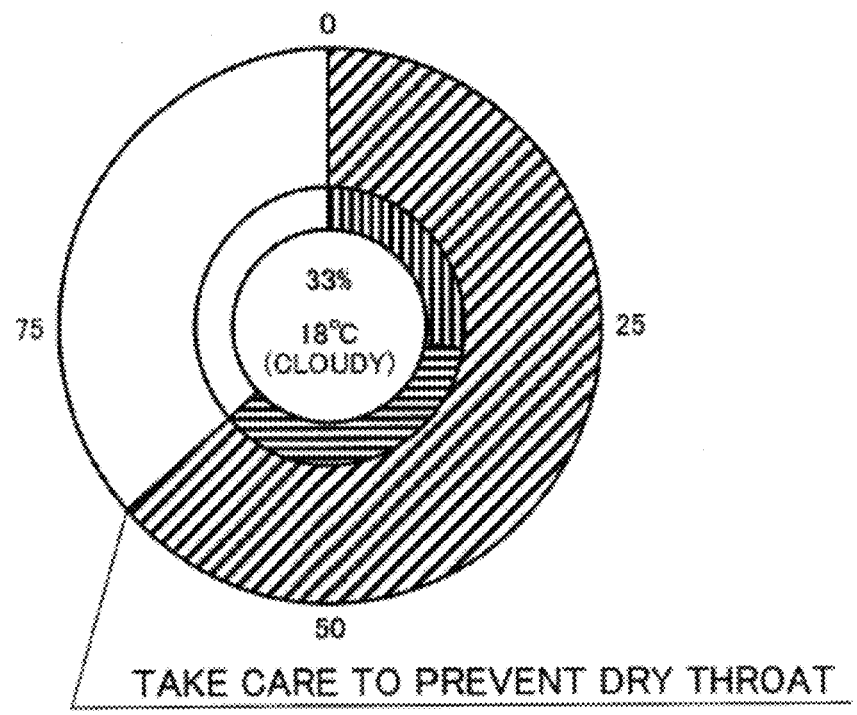

- MOLD DEVELOPMENT PROBABLE
- DEHUMIDIFY/REMOVE BACTERIA

· WATCH OUT FOR FLU
· WASH YOUR HANDS AND GARGLE

- BACTERIA FLOATING
- RUN ION GENERATOR
- RUN AIR PURIFIER

- MUCH BACTERIA FLOATING
- PURIFY AIR IMMEDIATELY

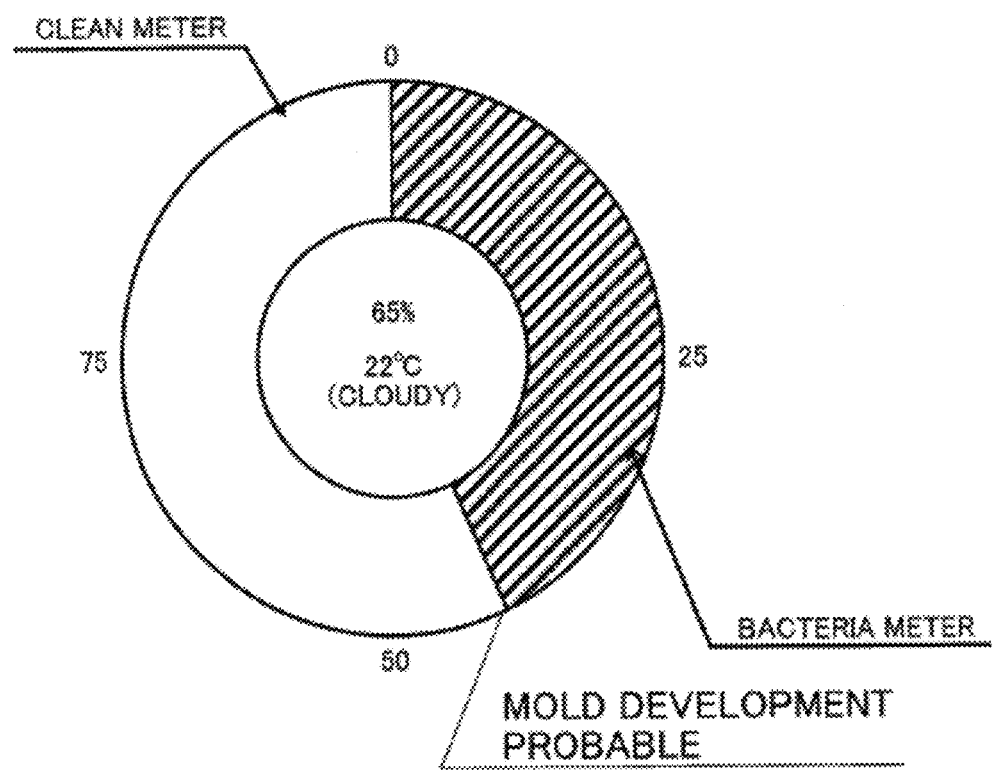

FIG.52

| LEVEL | MESSAGE |
|---|---|
| 0 | "AIR PURIFIED" |
| 1 | •"AIR LITTLE PURIFIED"<br>•"FURTHER PURIFY AIR" |
| 2 | |
| 3 | |
| 4 | |
| 5 | — |

FIG.53

| LEVEL | MESSAGE |
|---|---|
| 5 | "PURIFY AIR IMMEDIATELY" |
| 4 | •"AIR POLLUTION STARTED"<br>•"CLEANLINESS OF AIR DECREASING" |
| 3 | |
| 2 | |
| 1 | |
| 0 | — |

| LEVEL | MESSAGE |
|---|---|
| 5 | "AIR REMAINS POLLUTED" |
| 4 | • "AIR CONDITION NOT IMPROVED" |
| 3 | • "AIR KEPT IMPROVED" |
| 2 | |
| 1 | |
| 0 | "AIR KEPT CLEAN" |

| LEVEL | SOUND | LIGHT |
|---|---|---|
| 0 | MULTI-TONE CHORD MELODY | BLUE LAMP KEPT ON |
| 1 | FOUR-TONE CHORD MELODY | STATE OR FREQUENCY OF FLICKER CHANGED IN ACCORDANCE WITH LEVEL, OR TURNED ON ONLY AT A CERTAIN LEVEL OR LOWER. |
| 2 | THREE-TONE CHORD MELODY | |
| 3 | TWO-TONE CHORD MELODY | |
| 4 | SINGLE TONE MELODY | |
| 5 | — | — |

FIG.59

| LEVEL | SOUND | LIGHT |
|---|---|---|
| 5 | CONTINUOUS BUZZER SOUND | RED LAMP KEPT ON |
| 4 | INTERVAL OF BUZZER SOUND CHANGED IN ACCORDANCE WITH LEVEL, OR BUZZER SOUND PRODUCED ONLY AT A CERTAIN LEVEL OR HIGHER. | STATE OR FREQUENCY OF FLICKER CHANGED IN ACCORDANCE WITH LEVEL, OR TURNED ON ONLY AT A CERTAIN LEVEL OR LOWER. |
| 3 | | |
| 2 | | |
| 1 | | |
| 0 | — | — |

FIG.60

| LEVEL | SOUND | LIGHT |
|---|---|---|
| 5 | BUZZER SOUND MAY BE PRODUCED | RED LAMP MAY BE TURNED ON |
| 4 | INTERVAL OF BUZZER SOUND MAY BE CHANGED IN ACCORDANCE WITH LEVEL, OR BUZZER SOUND MAY NOT BE PRODUCED. | STATE OR FREQUENCY OF FLICKER MAY BE CHANGED IN ACCORDANCE WITH LEVEL, OR LAMP MAY NOT BE TURNED ON. |
| 3 | | |
| 2 | | |
| 1 | | |
| 0 | MELODY MAY BE PRODUCED | BLUE LAMP MAY BE TURNED ON |

DISPLAY CONTROL DEVICE

TECHNICAL FIELD

The present invention relates to a display control device and, more specifically, to a display control device for displaying information related to environment.

BACKGROUND ART

As a device for displaying information related to environment, Japanese Patent Laying-Open No. 2000-283533 (hereinafter referred to as Patent Literature 1) discloses a pollution state display device that detects amount of dust in air by a dust sensor and giving stepwise display of degree of air pollution.

CITATION LIST

Patent Literature

PTL 1: Japanese Patent Laying-Open No. 2000-283533

SUMMARY OF INVENTION

Technical Problem

The device according to Patent Literature 1 only displays the amount of dust as information related to environment. It is noted, however, that not only the amount of dust but also amount of microorganisms, temperature, humidity, climate, and weather may be used as indexes for determining the environmental state including risk of catching a cold or risk of mold development. The environmental status can be determined with high accuracy if these indexes are generally utilized. Therefore, there is a problem that a user cannot appropriately determine the environmental status from the display of the device of Patent Literature 1. Further, if the user does not have knowledge to determine the environmental status using these pieces of information as indexes, he/she cannot appropriately determine the environmental status.

The present invention was made in view of the foregoing, and one of its objects is to provide a display control device that displays information related to environment in an easy-to-understand manner.

Solution to Problem

In order to attain the above-described object, according to an aspect, the present invention provides a display control device, including: a first input unit for receiving an input of detection result related to amount of microorganisms in the air from a detection apparatus; and a computing device; wherein the computing device executes a computing process for obtaining a relative value of the amount of microorganisms detected by the detection apparatus with respect to a predetermined amount of microorganisms, and a display process for causing a display device to give a first display representing the amount of microorganisms detected by the detection apparatus in an area corresponding to the relative value, in a first display area representing the predetermined amount of microorganisms.

According to another aspect, a display control device includes: a first input unit for receiving an input of detection result related to amount of microorganisms in the air from a detection apparatus; and a computing device; wherein the computing device executes a process for determining a message to be displayed at least based on the detection result received by the first input unit, and a process for generating display data causing the display device to display an image including the message.

Preferably, the detection apparatus includes a light emitting element, a light receiving element having a light receiving direction at a prescribed angle to direction of irradiation of the light emitting element, and a processing device for processing amount of light received by the light receiving element as a detection signal; and the processing device includes an input unit for receiving an input of the amount of light received by the light receiving element as a detection signal, and a storage unit, and executes a process for comparing the detection signal with an arbitrary condition, for determining whether or not detected object is a microorganism, and a process for writing result of the determination in the storage unit.

Preferably, the first input unit includes a communication unit for communication with the detection apparatus; and the computing device includes a communication unit for communication with the display device.

Preferably, the first input unit further receives an input of result of detection of amount of particles other than microorganisms in the air from the detection apparatus; the computing device further executes a computing process for obtaining relative value of the amount of particles detected by the detection apparatus with respect to a predetermined amount of the particles other than microorganisms; and in the first display, a total sum of the predetermined amount of the microorganisms and the predetermined amount of the particles other than microorganisms is represented in the first display area, and the amount of particles is represented in an area corresponding to the relative value of the amount of particles other than microorganisms in the first display area.

More preferably, the computing device causes the display device, by the display process, to give a second display representing amount of particles in the air in an area corresponding to relative values of the microorganisms and the particles other than microorganisms in a second display area representing total sum of the predetermined amounts, together with the first display.

Preferably, the display control device further includes a second input unit for receiving an input of information related to environment from another device; and the computing device causes the display device, by the display process, to give a third display representing the information related to environment, together with the first display.

Preferably, the display control device further includes a second input unit for receiving an input of information related to environment from another device; and in the process for determining a message to be displayed, the computing device determines a message to be displayed based on the detection result received by the first input unit and on the value received by the second input unit.

Preferably, the display control device further includes a storage device for storing at least correspondence relation between the detection result received by the first input unit and a message to be displayed.

Preferably, the image includes the message and the detection result received by the first input unit.

Preferably, the first input unit further receives input of detection result of amount of particles other than microorganism in the air from the detection apparatus.

Advantageous Effects of Invention

By the present invention, the user can easily grasp pieces of information of different types related to environment by the display.

BRIEF DESCRIPTION OF DRAWINGS

FIG. 35 shows specific examples of correspondence between messages and conditions for determining messages.

FIG. 43A shows a specific example of display.
FIG. 43B shows a specific example of displayed messages.
FIG. 50A shows a specific example of display in accordance with Modification 1 of the display control of the second example.
FIG. 50B shows a specific example of displayed messages.
FIG. 52 shows specific examples of correspondence between messages and conditions for determining messages in accordance with Modification 2 of the display control of the second example.
FIG. 53 shows specific examples of correspondence between messages and conditions for determining messages in accordance with Modification 2 of the display control of the second example.
FIG. 59 shows specific examples of correspondence between messages and conditions for determining messages in accordance with Modification 2.
FIG. 60 shows specific examples of correspondence between messages and conditions for determining messages in accordance with Modification 2.

DESCRIPTION OF EMBODIMENTS

Figure 1A:
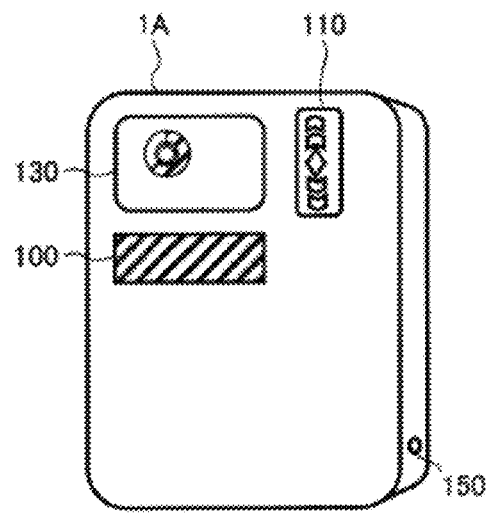
FIG. 1A shows a specific example of an outer appearance of an air purifier as the display control device.

In the following, embodiments of the present invention will be described with reference to the figures. In the following description, the same parts and components are denoted by the same reference characters. Their names and functions are also the same.

In the embodiments, it is assumed that the air purifier functions as a display control device.

<Configuration of Air Purifier>

Referring to FIG. 1A, an air purifier 1 serving as the display control device includes a switch 110 for accepting an operation instruction, a display panel 130 for displaying a detection result and others, and a detection apparatus 100 functioning as a microorganism sensor for detecting microorganisms from airborne particles, as will be described later. In addition, it may include an inlet for introducing air, an outlet for discharging air and the like, not shown. Air purifier 1 may further include a communication unit 150 for communication with other equipment.

Figure 1B:
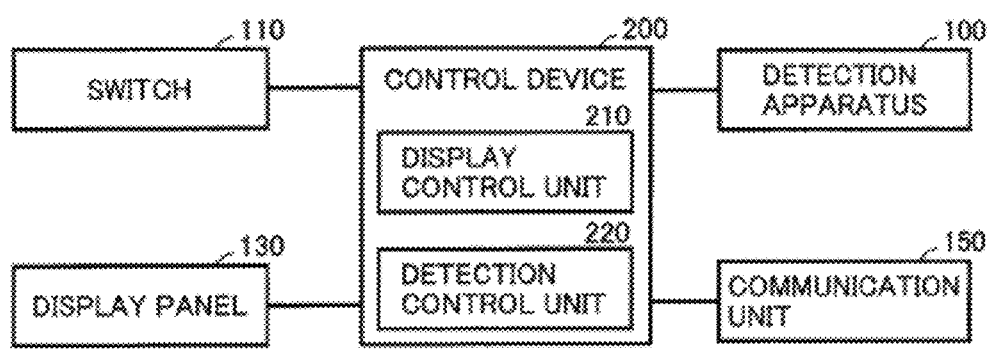
FIG. 1B shows a specific example of a configuration of the display control device in accordance with an embodiment.

Referring to FIG. 1B, air purifier 1 further includes a control device 200. Control device 200 includes a CPU (Central Processing Unit) and a memory, not shown. The CPU reads and executes a program or programs stored in the memory in accordance with an instruction signal from switch 110. Thus, display on display panel 130, control of detection apparatus 100, and control of communication unit 150 are realized. For this purpose, control device 200 includes a display control unit 210 for controlling display on display panel 130, and a detection control unit 220 for controlling detection apparatus 100. Display control unit 210 and detection control unit 220 may be functions realized mainly by the CPU as it executes programs, or they may be functions realized by hardware such as electric circuits.

<Description of Detection Apparatus>

Detection apparatus 100 detects amount of airborne biological particles. Though the "biological particles" are represented by microorganisms (including dead bodies) of bacteria or the like in the following description, the particles refer to any particles that perform vital action or a part or parts thereof, dead or alive, having the size small enough to be airborne, not limited to microorganisms. Specifically, in addition to microorganisms (including dead body) such as bacteria or fungi, pollen, mites (and their dead bodies) and the like may be included. In the following description, the term "microorganisms" represents the "particles of biological origin" including pollen and other particles.

In the following, first to third examples will be referred to as examples of detection apparatus 100.

First Example of the Detection Apparatus

Figure 2:
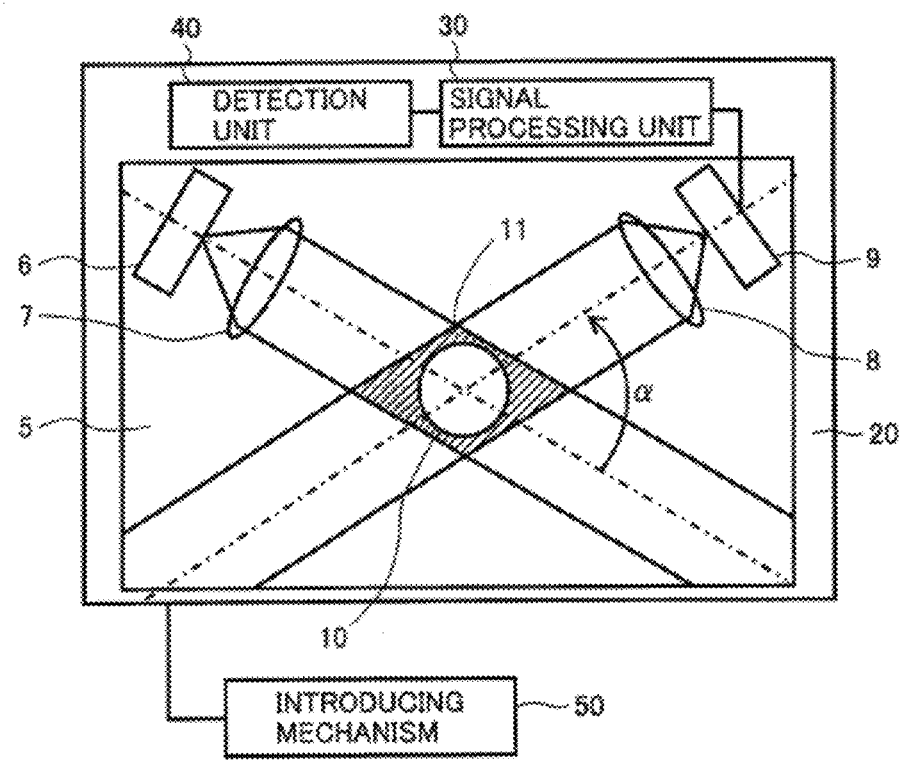
FIG. 2 shows a basic structure of a detection apparatus in accordance with a first example, included in the air purifier.

FIG. 2 shows the first example of detection apparatus 100.

Referring to FIG. 2, detection apparatus 100A in accordance with the first example has a case 5 provided with an inlet 10 for introducing the air through the suction opening and an outlet, not shown, and also includes a sensor 20, a signal processing unit 30 and a detecting unit 40 which are located inside case 5.

Detection apparatus 100A includes an introducing mechanism 50. Introducing mechanism 50 introduces the air through the suction opening into case 5 at a predetermined flow rate. For example, introducing mechanism 50 may be a fan or a pump arranged outside case 5 as well as a drive mechanism for it, or the like. Further, it may be a thermal heater, a micro-pump or a micro-fan arranged in case 5 as well as a drive mechanism for it, or the like. Further, introducing mechanism 50 may have a configuration shared with an air introducing mechanism of the air cleaning device portion in the air purifier.

Detection control unit 220 controls the drive mechanism included in introducing mechanism 50 to control the flow rate of the introduced air. The flow rate at which introducing mechanism 50 introduces the air is not restricted to a predetermined flow rate. Detection apparatus 100 converts a current signal provided from a light receiving element 9 into sizes of suspended particles in a manner to be described later, and therefore the flow rate must be controlled to fall within a range not exceeding an excessive value for allowing such conversion. Preferably, the flow rate of the introduced air is in a range from 0.01 lit/min to 10 lit/min.

Sensor 20 includes a light emitting element 6 that is a light source, a lens 7 that is arranged in a radiation direction of light emitting element 6 for changing the light beams radiated from light emitting element 6 into parallel light beams or light beams having a predetermined width, light receiving element 9, and a collecting lens 8 that is arranged in a light receiving direction of light receiving element 9 for condensing, on light receiving element 9, scattered light occurring from the parallel light beams due to suspended particles in the air.

Light emitting element 6 includes a semiconductor laser or an LED (Light Emitting Diode) element. The wavelength may be in any of ultraviolet, visible and near-infrared ranges. Light receiving element 9 may be a conventional element such as a photodiode or an image sensor.

Each of lens 7, which is a collimate lens, and collecting lens 8 may be made of plastic resin or glass. The width of the parallel light beams produced by lens 7 is not restricted to a specific value, but is preferably in a range from about 0.05 mm to about 5 mm.

When the light radiated from light emitting element 6 has a wavelength in the ultraviolet range, an optical filter for filtering out fluorescence that is emitted from suspended particles of biological origin is arranged before collecting lens 8 or light receiving element 9 so that the fluorescence may not enter light receiving element 9.

Case 5 has a rectangular parallelepiped shape with the length of each side being 3 mm to 500 mm. Though case 5 has a rectangular parallelepiped shape in the present embodiment, the shape is not limited, and the case may have a different shape. Preferably, at least the inner side is painted black or treated with black alumite. This prevents reflection of light from the inner wall surface as a cause of stray light. Though the material of case 5 is not specifically limited, preferably, plastic resin, metal such as aluminum or stainless steel or a combination of these may be used. Inlet 10 and outlet of case 5 have circular shape with the diameter of 1 mm to 50 mm. The shape of inlet 10 and outlet is not limited to a circle, and it may be an ellipse or a rectangle.

Light emitting element 6 and lens 7 as well as light receiving element 9 and collecting lens 8 are arranged such that the radiation direction of the light beams emitted by light emitting element 6 and collimated by lens 7 keeps a predetermined angle α with respect to the direction in which light receiving element 9 can receive the light condensed by collecting lens 8. Further, they are angularly arranged such that the air moving from inlet 10 to the outlet may flow through a region 11 in FIG. 2 where the radiation region of the light emitted by light emitting element 6 and collimated by lens 7 overlaps a reception region where light receiving element 9 can receive the light condensed by collecting lens 8. FIG. 2 shows an example of the positional relationship where the angle α is about 60 degrees and region 11 is located in front of inlet 10. The angle α is not restricted to 60 degrees, and may be of another value.

Light receiving element 9 is connected to signal processing unit 30, and provides a current signal proportional to an amount of the received light to signal processing unit 30. In the structure shown in FIG. 2, the light radiated from light emitting element 6 is scattered by the particles that are suspended in the air and are being moved in region 11 at a predetermined flow rate by introducing mechanism 50 from inlet 10 to the outlet. Light receiving element 9 receives the light beams that are contained in the above scattered light and form an angle α (=60 degrees) with respect to the radiation direction of light emitting element 6, and detects the amount of the received light.

Signal processing unit 30 is connected to detecting unit 40, and provides a result of its processing performed on the pulse-like current signal to detecting unit 40. Based on the processing result provided from signal processing unit 30, detecting unit 40 performs the processing for detecting microorganisms from airborne particles and outputting the results of detection.

A detection principle of detection apparatus 100A is described below.

An intensity of the light scattered by the suspended particles in the air depends on the size and the refraction factor of the suspended particles. Since the microorganisms that are the suspended particles of biological origin have cells filled with liquid similar to water, the microorganisms can be approximated as transparent particles having the refraction factor close to that of the water. Assuming that the suspended particles of biological origin have the refraction factor close to that of the water, detection apparatus 100A utilizes the difference which appears in scattering intensity at a specific scattering angle of the radiated light between the suspended particles of biological origin and the dust particles of the same sizes, and thereby discriminates between the suspended particles of biological origin and the other suspended particles for detecting the former.

Figure 3:
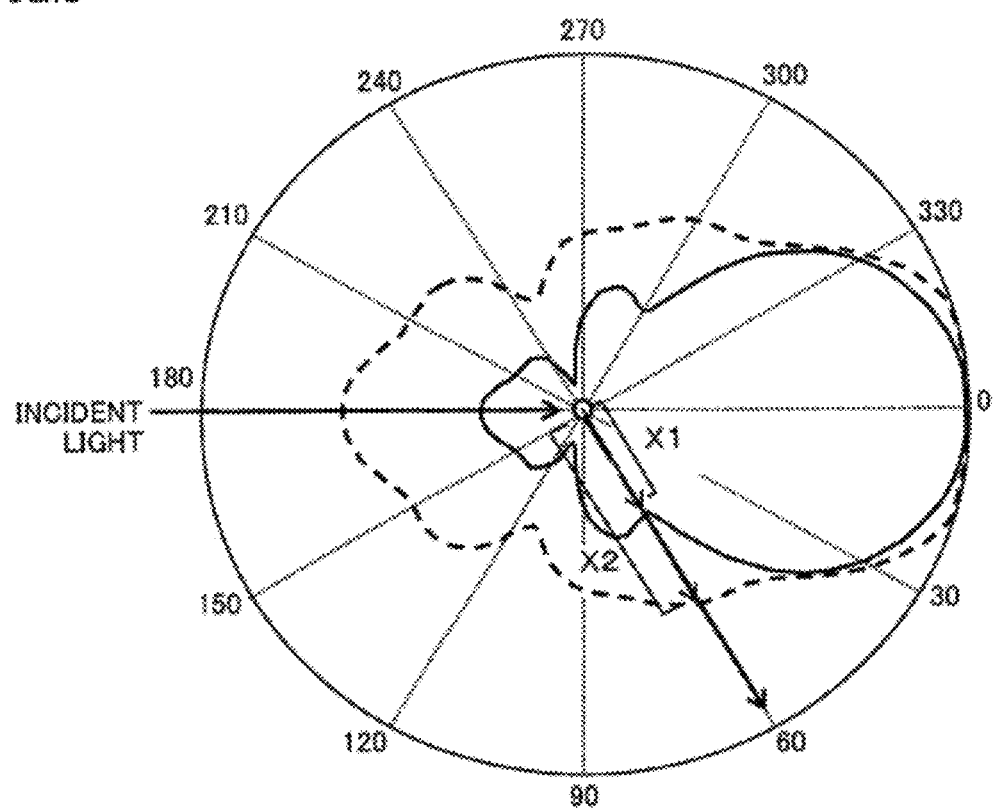
FIG. 3 illustrates a result of simulation of a correlation between a scattering angle and a scattering intensity relating to dust particles and microorganism particles having the same size.

FIG. 3 shows a simulation result in which scattering intensity is plotted with various scattering angles in connection with spherical particles of 1 micron in diameter, and particularly in connection with particles of 1.3 in refraction factor close to that of the water and those of 1.6 in refraction factor different from that of water. In FIG. 3, thick line represents a result of simulation relating to the scattering intensity of the particles of 1.3 in refraction factor, and dotted line represents a result of simulation relating to the scattering intensity of the particles of 1.6 in refraction factor.

Referring to FIG. 3, from a comparison in scattering intensities at the scattering angle, e.g., of 60 degrees, it can be seen that a discriminative difference is present between a scattering intensity X1 of the particles exhibiting the refraction factor of 1.3, i.e., the particles of biological origin and a scattering intensity X2 of the particles exhibiting the refraction factor of 1.6 that are assumed as representative dust. Thus, when a value between scattering intensities X1 and X2 is used in advance as a boundary value, the scattering intensities at the scattering angle of 60 degrees of the spherical particles having a diameter of 1 micron can be determined such that the particles exhibiting the scattering intensities smaller than the boundary value are of biological origin, and the particles of larger scattering intensities are the dust particles.

Detection apparatus 100A applies this principle to the suspended particles in the introduced air to discriminate between the suspended particles of biological origin and other particles. For this, boundary values for discriminating between the suspended particles of biological origin and the other suspended particles are set in advance in detection apparatus 100A for various particle sizes, respectively. Detection apparatus 100 measures the sizes of the suspended particles in the introduced air as well as the scattering intensities, and determines that these are the particles of biological origin when the measured scattering intensity is smaller than the boundary value already set with respect to the measured size, and otherwise determines that the particles are the dust particles.

Detection apparatus 100A can detect the sizes of the suspended particles in the introduced air, using the following principle. When the flow rate of the air is not high, the speed of the suspended particles in the air flowing at a certain speed decreases with increase in size of the suspended particles, as is well known. According to this principle, when the size of the suspended particles increases, its speed decreases so that the time for which the suspended particle moves across the radiated light increases. Light receiving element 9 of detection apparatus 100A receives the scattered light that is generated by the suspended particles when the suspended particles moving at a certain flow rate move across the light radiated from light emitting element 6. Accordingly, the current signal issued from light receiving element 9 takes a pulse-like form, of which pulse width correlates with the time for which the suspended particle moves across the radiated light. Accordingly, the pulse width of the issued current signal is converted into the size of the suspended particle. For allowing this conversion, detection control unit 220 controls the flow rate of the air introduced by introducing mechanism 50 to attain an unexcessive speed so that the pulse width of the current signal provided from light receiving element 9 may reflect the size of the suspended particle.

Figure 4:
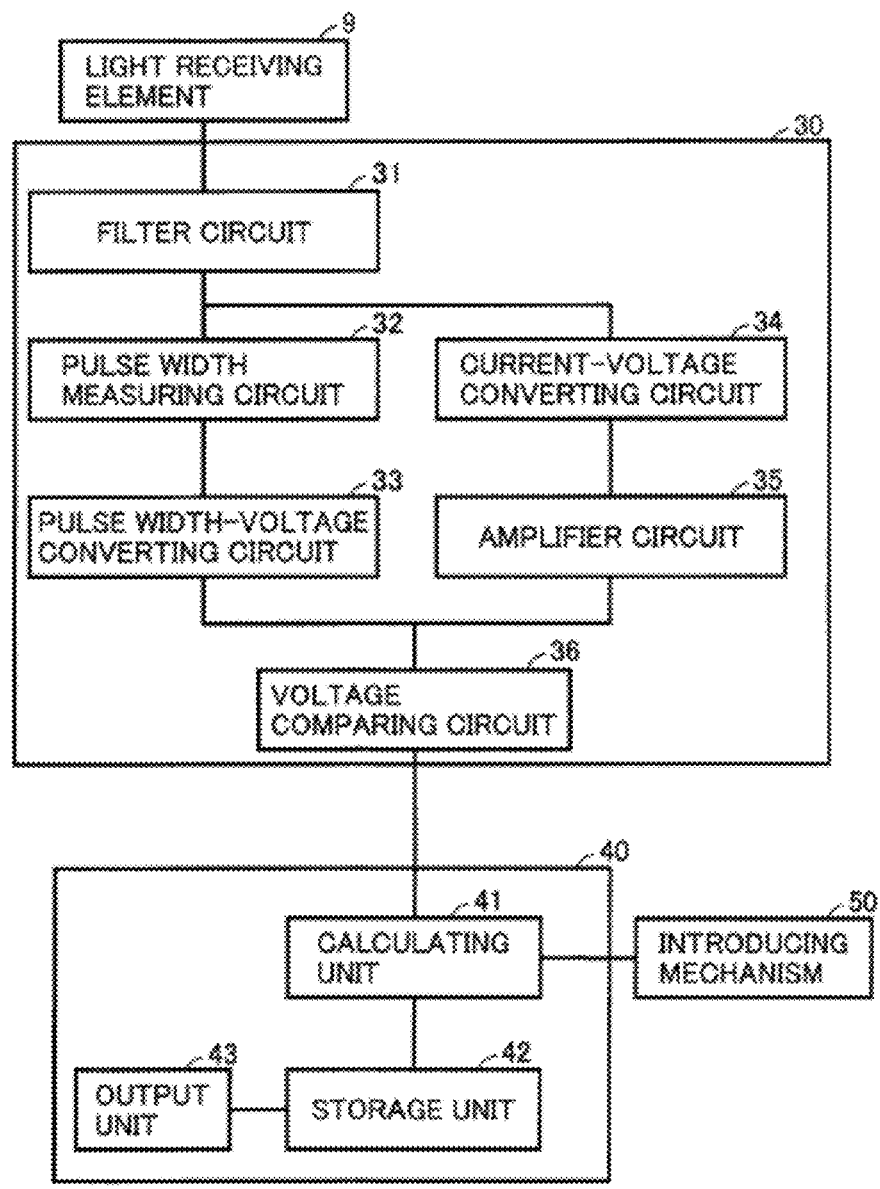
FIG. 4 is a block diagram of a specific example of functional configuration of the detection apparatus in accordance with the first example.

A functional structure of detection apparatus 100A that uses above-described principle for detecting the microorganisms in the air will be described below with reference to FIG. 4. FIG. 4 shows an example in which the functions of signal processing unit 30 are implemented by hardware configuration mainly of electric circuitry. However, at least part of the functions may be implemented by software configuration realized by a CPU, not shown, provided in signal processing unit 30, executing a predetermined program. In the illustrated example, the structure of detecting unit 40 is a software structure. However, a hardware structure such as an electric circuit may implement at least a part of such function.

Referring to FIG. 4, signal processing unit 30 includes a pulse width measuring circuit 32 connected to light receiving element 9, a pulse width-voltage conversion circuit 33 connected to pulse width measuring circuit 32, a current-voltage conversion circuit 34 connected to light receiving element 9, an amplifier circuit 35 connected to current-voltage conversion circuit 34 and a voltage comparison circuit 36 connected to pulse width-voltage conversion circuit 33 and amplifier circuit 35. Preferably, as shown in FIG. 4, a filter circuit 31 for removing signals of current values smaller than a preset value is arranged between light receiving element 9 on one side and pulse width measuring circuit 32 and current-voltage conversion circuit 34 on the other side. The provision of filter circuit 31 can reduce noise components in the detection signal of light receiving element 9 due to stray light.

Detecting unit 40 includes a calculating unit 41, a storage unit 42 and an output unit 43 for outputting the result of detection.

Figure 5:
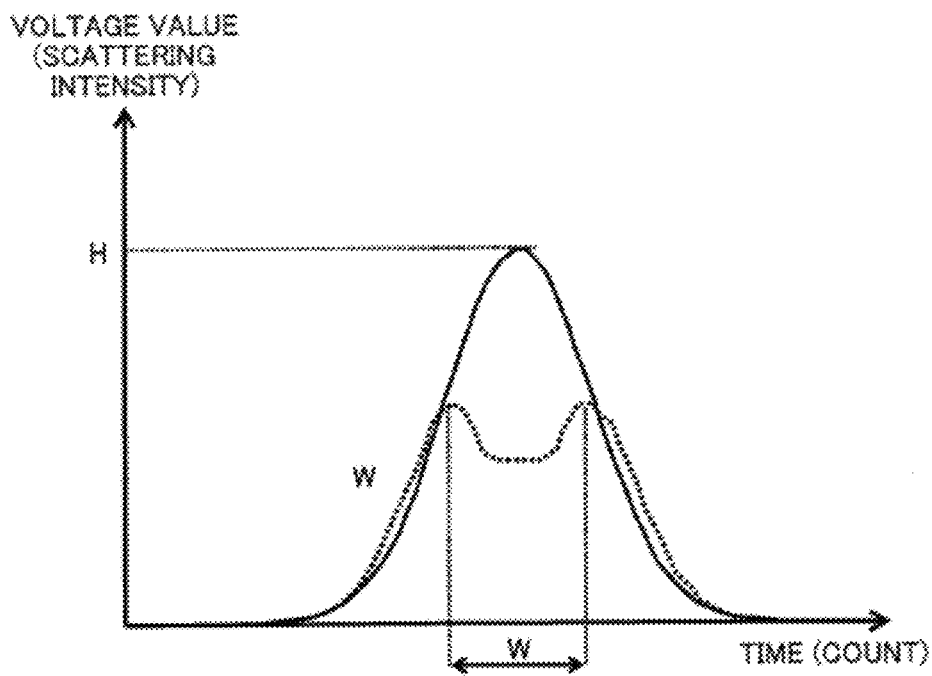
FIG. 5 shows a specific example of a detection signal.

When light emitting element 6 irradiates the suspended particles introduced into case 5 with the light, light receiving element 9 collects the light scattered by the suspended particles in region 11 shown in FIG. 2. Light receiving element 9 provides the pulse-like current signal shown in FIG. 5 and corresponding to the amount of received light to signal processing unit 30. The current signal is provided to pulse width measuring circuit 32 and current-voltage conversion circuit 34 of signal processing unit 30. Among the current signals provided from light receiving element 9, the signals of the current values smaller than the preset value are filtered out by filter circuit 31.

Current-voltage conversion circuit 34 detects a peak current value H representing the scattering intensity from the current signal provided from light receiving element 9, and converts it into a voltage value Eh. Amplifier circuit 35 amplifies voltage value Eh with a preset amplification factor, and provides it to voltage comparison circuit 36.

Pulse width measuring circuit 32 measures a pulse width W of the current signal provided from light receiving element 9. The method of measuring the pulse width or the value related to it by pulse width measuring circuit 32 is not restricted to a specific method, and may be a well-known signal processing method. By way of example, description will be made on a measuring method in the case where a differentiation circuit (not shown) is arranged in pulse width measuring circuit 32. When the pulse-like electric signal is applied, the differentiation circuit generates a certain voltage determined corresponding to the initial pulse signal, and this voltage will return to zero in response to a next pulse signal. Pulse width measuring circuit 32 measures a time between the rising and the falling of the voltage signal that occurs in the differentiation circuit, and can use it as the pulse width. Thus, pulse width W may be a width between peaks of a differentiation curve that is obtained using the differentiation circuit, as represented, e.g., by dotted line in FIG. 5. In other examples, pulse width W may be an interval between halves of the peak voltage values of the pulse waveform, i.e., may be a half-value width, and also may be an interval between the rising and falling of the pulse waveform. The signal indicative of pulse width W that is measured according to one of these or other methods is provided to pulse width-voltage conversion circuit 33.

In pulse width-voltage conversion circuit 33, a voltage value Ew to be used as a boundary value of the scattering intensity for determining whether the suspended particles are of biological origin or not is set in advance for each pulse width W. Pulse width-voltage conversion circuit 33 converts pulse width W provided thereto into voltage value Ew according to the above setting. The correlation between pulse width W and voltage value Ew may be set as a function or a coefficient, and may also be set in a table. Voltage value Ew is output to voltage comparing circuit 36.

Figure 6:
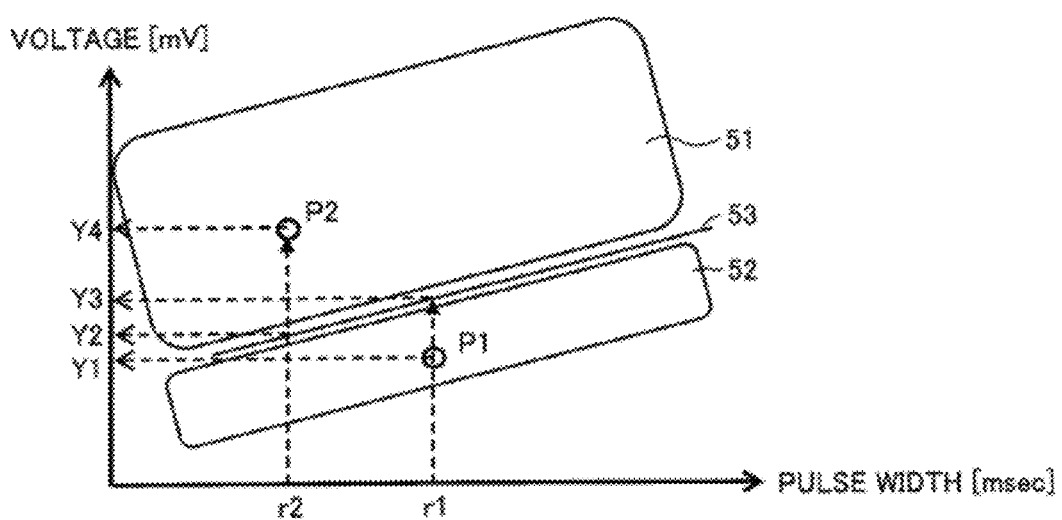
FIG. 6 illustrates a relationship between a pulse width and the scattering intensity.

Voltage value Ew that is the boundary value corresponding to pulse width W is experimentally determined in advance. By way of example, one type of microorganism such as *Escherichia coli*, *Bacillius subtilis* or *Penicillium* is sprayed using a nebulizer in a vessel having the size of 1 m$^3$, and detection apparatus 100 measures the pulse width and the scattering intensity (peak voltage value) from the current signal provided from light receiving element 9. Likewise, polystyrene particles having uniform sizes are used in place of dust, and detection apparatus 100 measures the pulse width and the scattering intensity (peak voltage value). FIG. 6 is a diagram prepared by plotting the scattering intensities (peak voltage values) with respect to the pulse widths, and particularly the scattering intensities that are obtained by detection apparatus 100 from the microorganisms and the polystyrene particles. In a region 51 of FIG. 6, the scattering intensities that are correlated to the pulse widths obtained from the polystyrene particles are plotted. In a region 52, the scattering intensities that are correlated to the pulse widths obtained primarily from the microorganisms are plotted. In practice, these plotted intensities partially overlap in these regions and are mixed with each other to some extent. This is due to variations in flow rate of the air introduced into case 5, variations in route of suspended particle moving across the radiated light, distribution of the intensity of the radiated light and others. Since regions 51 and 52 are experimentally obtained, the boundary between them is determined, e.g., as straight line 53. For example, a function or a coefficient representing straight line 53 is set in pulse width-voltage conversion circuit 33.

The correlation that is present between pulse width W and voltage value Ew and is represented by straight line 53 may be set in voltage comparison circuit 36 by detection control unit 220. Alternatively, communication unit 150 may read such information from a recording medium recording correlation between pulse width W and voltage value Ew, and the correlation may be set by detection control unit 220. Alternatively, communication unit 150 may receive the correlation from a PC connected to a dedicated line or other device communicating through the Internet or infrared ray, and the correlation may be set by detection control unit 220. Further, the correlation between pulse width W and voltage value Ew once set in voltage comparing circuit 36 may be updated by detection control unit 220.

Voltage comparison circuit 36 makes a comparison between voltage value Eh that is provided from current-voltage conversion circuit 34 through amplifier circuit 35 and is indicative of the scattering intensity and voltage value Ew that is provided from pulse width-voltage conversion circuit 33 and is the boundary value corresponding to pulse width W. Based on this comparison, voltage comparison circuit 36 determines whether the suspended particles that cause the scattered light received by light receiving element 9 are of biological origin or not, i.e., are microorganisms or not.

A practical example of the determination method in voltage comparison circuit 36 will be described below with reference to FIG. 6. For example, when a pulse width r1 and a scattered light intensity, i.e., a peak voltage value Y1 are detected from a certain suspended particle P1, pulse width-voltage conversion circuit 33 converts pulse width r1 into a voltage value Y3 based on the correlation represented by straight line 53 that has been set. Voltage comparison circuit 36 receives peak voltage values Y1 and voltage value Y3, and makes a comparison between them. Since peak voltage value Y1 is smaller than voltage value Y3 that is the boundary value, it is determined that particle P1 is of biological origin, i.e., that it is a microorganism.

For example, when a pulse width r2 and a scattered light intensity, i.e., a peak voltage value Y4 are detected from certain suspended particle P2, pulse width-voltage conversion circuit 33 converts pulse width r2 into voltage value Y2 based on the correlation represented by straight line 53 that has been set. Voltage comparison circuit 36 receives peak voltage value Y4 and voltage value Y2, and makes a comparison between them. Since peak voltage value Y4 is larger than voltage value Y2 that is the boundary value, it is determined that particle P2 is not of biological origin.

Voltage comparison circuit 36 performs the determination based on the light scattered by the suspended particle every time the particle moves across the light emitted by light emitting element 6, and provides the signal indicative of the determination result to detecting unit 40. Calculating unit 41 of detecting unit 40 accepts the input of the determination results provided from voltage comparison circuit 36, and successively stores them in storage unit 42.

Calculating unit 41 performs calculation on the determination result that is obtained for a predetermined detection time and is stored in storage unit 42, and specifically it counts the input of signals indicative of the determination result that the suspended particle of the measurement target is a microorganism, and/or counts the input of signals indicative of the determination result other than the above.

Calculating unit 41 reads the flow rate of the air introduced through introducing mechanism 50, and multiplies it by the above detection time to obtain a quantity Vs of the air introduced into case 5 for the above detection time. Calculating unit 41 obtains, as the measurement result, a concentration Ns/Vs of the microorganisms or a concentration Nd/Vs of the dust particles by dividing the result of the above counting, i.e., a number Ns of the microorganisms or a number Nd of the dust particles by air quantity Vs.

The number of microorganisms Ns and the number of dust particles Nd counted in the detection time period as the results of detection, the calculated concentration of microorganisms Ns/Vs and the concentration of dust particles Nd/Vs are stored in storage unit 42. At prescribed timing, the results of detection are output by output unit 43 to display control unit 210. The timing of output from output unit 43 may be prescribed time interval set in advance, or timing requested by display control unit 210.

A specific example of the detection method in detection apparatus 100A will be described below with reference to FIG. 7. The detection method in FIG. 7 is implemented by such operations that signal processing unit 30 and detecting unit 40 receive a control signal from an arithmetic unit such as a CPU which is included in detection apparatus 100A but is not shown in the figure, and thereby the various circuits and functions illustrated in FIG. 4 are implemented according to the received control signal.

Figure 7:
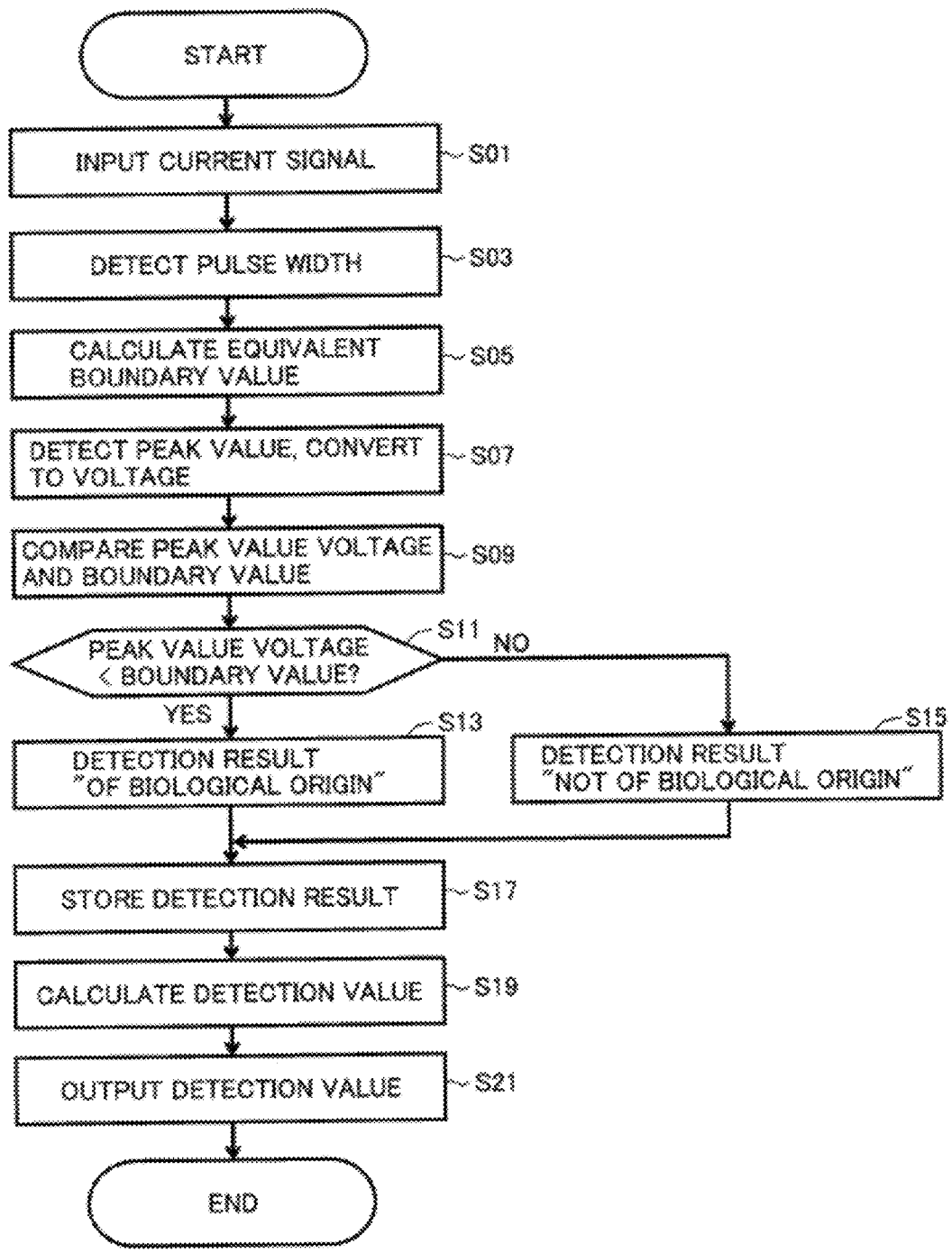
FIG. 7 is a flowchart showing a specific example of a detection method executed by the detection apparatus in accordance with the first example.

Referring to FIG. 7, the suspended particles carried by the moving air move across the light radiated from light emitting element 6. Thereby, when the current signal that is caused by the scattered light generated by the suspended particles is provided from light receiving element 9 to signal processing unit 30 through filter circuit 31 at a step (which will be simply expressed as "S" hereinafter) 101, pulse width measuring circuit 32 detects a pulse width W of this pulse-like current signal at S03. At S05, pulse width-voltage conversion circuit 33 converts pulse width W detected at S03 into the boundary value, i.e., voltage value Ew based on the correlation that is set in advance.

At S07, current-voltage conversion circuit 34 detects peak current value H indicative of the scattering intensity from the pulse-like current signal that is provided from light receiving element 9 in S01, and converts it into peak voltage value Eh. The order of steps S03-S07 is not restricted to the above order.

Amplifier circuit 35 amplifies voltage value Eh obtained at S07 at a preset amplification factor and, at S09, voltage comparison circuit 36 compares it with voltage value Ew obtained at S05. As a result, when the peak voltage value is smaller than the boundary value (YES at S11), voltage comparison circuit 36 determines that the suspended particles that generate the scattered light detected as the current signal in question are of biological origin, and the signal indicative of the result thereof is provided to detecting unit 40. Conversely, when the peak voltage value is larger than the boundary value (NO at S11), voltage comparison circuit 36 determines that the suspended particles are not of biological origin, and provides the signal indicative of the result to detecting unit 40.

At S17, storage unit 42 of detecting unit 40 stores the result of detection provided from voltage comparison circuit 36 at S13 or S15. At S19, calculating unit 41 performs the operation on the determination results that are obtained for the predetermined detection time and are stored in storage unit 42, and specifically counts the inputs of the determination result indicating that the suspended particles are of biological origin and/or the inputs of the determination result indicating that they are not of biological origin. The result of the former counting is handled as number Ns of the microorganisms, and the result of the latter counting is handled as number Nd of the dust particles. Further, calculating unit 41 multiplies the above detection time by the flow rate of the air to obtain quantity Vs of the air introduced into case 5 for the above detection time. Therefore, by dividing number Ns or Nd of the microorganisms or the dust particles obtained by the counting by air quantity Vs, concentration Ns/Vs of the microorganisms or concentration Nd/Vs of the dust particles are obtained as the detection value. The detection value obtained at S19 is output at S21 from output unit 43 at prescribed timing, to display control unit 210.

By the determination about the microorganisms and the dust as described above, detection apparatus 100A can separate the microorganisms among the suspended particles in the air from the dust and can accurately detect them in real time.

Second Example of the Detection Apparatus

Figure 8A:
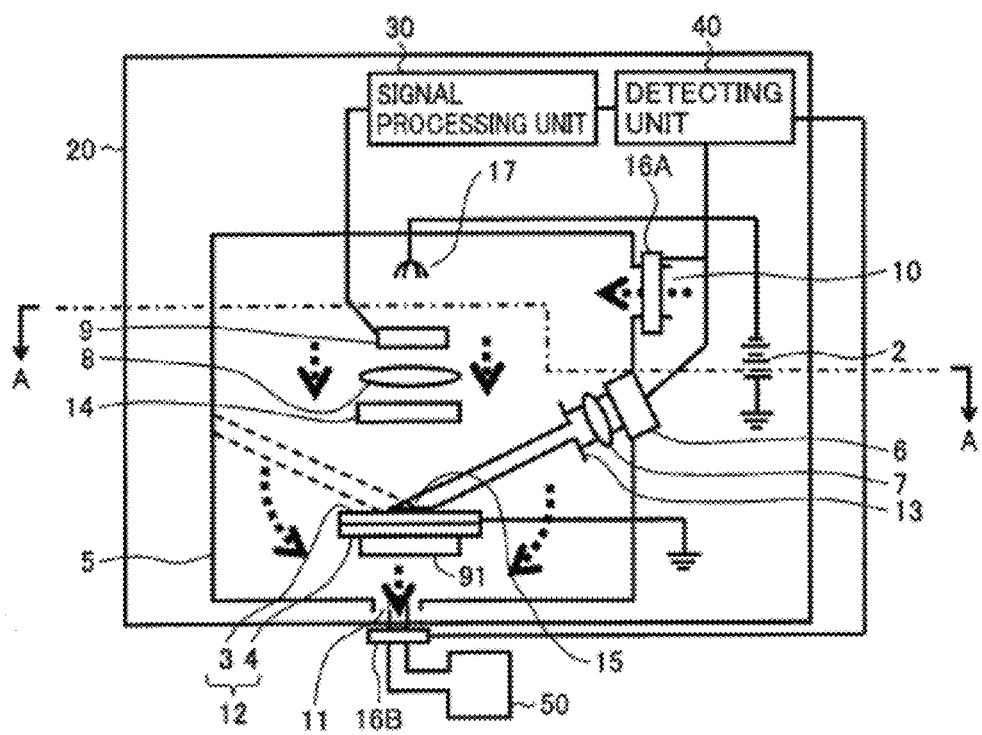
FIG. 8A shows a specific example of basic configuration of a detection apparatus in accordance with a second example, included in the air purifier.

FIG. 8A illustrates the second example of detection apparatus 100.

Referring to FIG. 8A, detection apparatus 100B in accordance with the second example has a case 5 with an inlet 10 for introducing air from the suction opening and an outlet 11, and includes a sensor 20 including the case 5, a signal processing unit 30 and a detecting unit 40. In FIG. 8A, components denoted by the same reference characters as in detection apparatus 100A of the first example are substantially the same as those of detection apparatus 100A and, in the following, the difference from detection apparatus 100A will be mainly described.

In detection apparatus 100B also, an introducing mechanism 50 is provided, which introduces air from the suction opening to case 5. In detection apparatus 100B, preferably, the flow rate of air introduced by introducing mechanism 50 is 1 L (liter)/min to 50 m$^3$/min.

Sensor 20 includes a detecting mechanism, a collecting mechanism and a heating mechanism. FIG. 8A shows, as an example of the collecting mechanism, a collecting mechanism including a discharge electrode 17, a collecting jig 12, and a high-voltage power supply 2. Discharge electrode 17 is electrically connected to a negative electrode of high-voltage power supply 2. The positive electrode of high-voltage power supply 2 is grounded. As a result, particles suspended in the introduced air are negatively charged near discharge electrode 17. Collecting jig 12 has a support board 4 formed, for example, of a glass plate, having a conductive, transparent coating 3. Coating 3 is grounded. Thus, the negatively charged particles suspended in the air move toward collecting jig 12 because of electrostatic force, and are attracted and held by conductive coating 3, whereby the particles are collected on collecting jig 12.

Support board 4 is not limited to a glass plate and it may be formed of ceramic, metal or other materials. Coating 3 formed on support board 4 is not limited to a transparent coating. As another example, support board 4 may include an insulating material such as ceramic, and a metal coating formed thereon. When support board 4 is of metal material, formation of a coating on its surface is unnecessary. More specifically, support board 4 can be a silicon board, a SUS (stainless used steel) board, a copper board, or the like.

The detecting mechanism includes: a light emitting element 6 as a light source; a lens (or lenses) 7, provided in the direction of light irradiation by emitting element 6, for collimating the light beams from light emitting element 6 or to adjust the light beams to a prescribed width; an aperture 13; a light receiving element 9; a collecting lens (or lenses) 8, provided in the direction of light reception by light receiving element 9, for collecting fluorescence generated by irradiation of airborne particles collected on collecting jig 12 by the collecting mechanism with light from light emitting element 6 to light receiving element 9; and a filter (or filters) 14 for preventing entrance of irradiating light beam to light receiving element 9. Aperture 13 is provided as needed. Conventional configurations may be applied to these components.

Light emitting element 6 may include a semiconductor laser or an LED device. Wavelength of light may be in ultraviolet range or visible range, provided that the light can excite and cause fluorescent emission from microorganisms. Preferable wavelength is 300 nm to 450 nm, with which tryptophan, NaDH, riboflavin and the like included in microorganisms and emitting fluorescence are efficiently excited, as disclosed in Japanese Patent Laying-Open No. 2008-508527. As light receiving element 9, conventional photo-diode, image sensor or the like is used.

Each of lens 7 and collecting lens 8 may be formed of plastic resin or glass. By a combination of lens 7 and aperture 13, light beams emitted from light emitting element 6 are collected on a surface of collecting jig 12, and form an irradiation region 15 on collecting jig 12. The shape of irradiation region 15 is not specifically limited, and it may have a circular, elliptical or rectangular shape. Though the size of irradiation region 15 is not specifically limited, preferably, the diameter of a circle, the longer side length of an ellipse or the length of one side of a rectangle is in the range of about 0.05 mm to 50 mm.

Filter 14 is formed of a single filer or a combination of different types of filters, and placed in front of collecting lens 8 or light receiving element 9. This prevents stray light derived from light emitted from light emitting element 6 and reflected by collecting jig 12 and case 5 from entering light receiving element 9 together with the fluorescence from particles collected by collecting jig 12.

The heating mechanism includes a heater 91 electrically connected to detecting unit 40 and having its amount of heating (heating time, heating temperature) controlled by detecting unit 40. Suitable heater 91 includes a ceramic heater. While in the following description, heater 91 is assumed as a ceramic heater, it may be a different heater, such as an infrared heater, an infrared lamp, or the like.

Figure 8B:
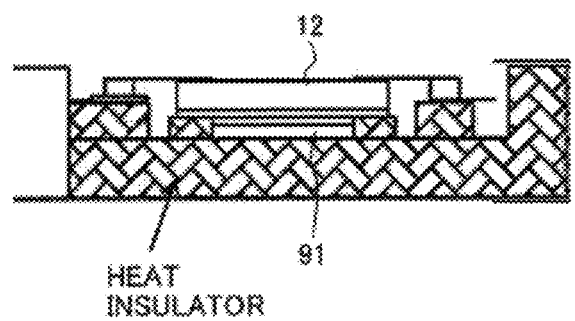
FIG. 8B shows a structure around a collecting jig and a heater, in the detection apparatus in accordance with the second example.

Heater 91 is provided at a position that can heat the airborne particles collected on collecting jig 12 and separated by some means or other at least at the time of heating from sensor equipment including light emitting element 6 and light receiving element 9. Preferably, as shown in FIG. 8A, the heater is arranged on a side away from the sensor equipment such as light emitting element 6 and light receiving element 9, with collecting jig 12 placed in between. By such an arrangement, at the time of heating, heater 91 is separated by collecting jig 12 from the sensor equipment including light emitting element 6 and light receiving element 9, whereby influence of heat on light emitting element 6, light receiving element 9 and the like can be prevented. More preferably, heater 91 is surrounded by heat insulating material as shown in FIG. 8B. Suitable heat insulating material includes glass epoxy resin. With such a structure, the inventors confirmed that when heater 91 implemented by a ceramic heater reached 200° C. in about 2 minutes, the temperature of a portion (not shown) connected to heater 91 with the heat insulating member interposed was not higher than 30° C.

As described above, filter 14 is placed in front of light receiving element 9 and serves to prevent entrance of stray light to light receiving element 9. In order to attain higher fluorescent intensity, however, it becomes necessary to increase intensity of light emitted from light emitting element 6. This leads to higher intensity of reflected light, that is, increased intensity of stray light. Therefore, light emitting element 6 and light receiving element 9 are arranged to have such a positional relation that the stray light intensity is kept lower than the light intercepting effect attained by filter 14.

Figure 9A:
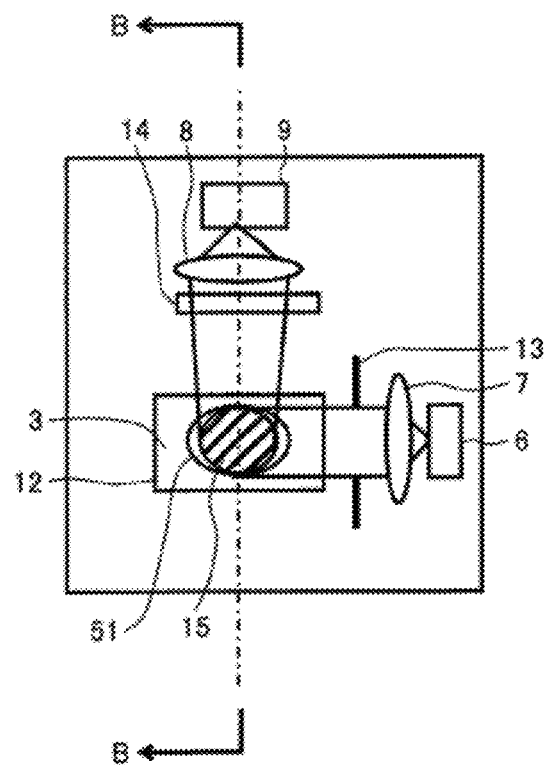
FIG. 9A is an illustration of a detecting mechanism in the detection apparatus.
Figure 9B:
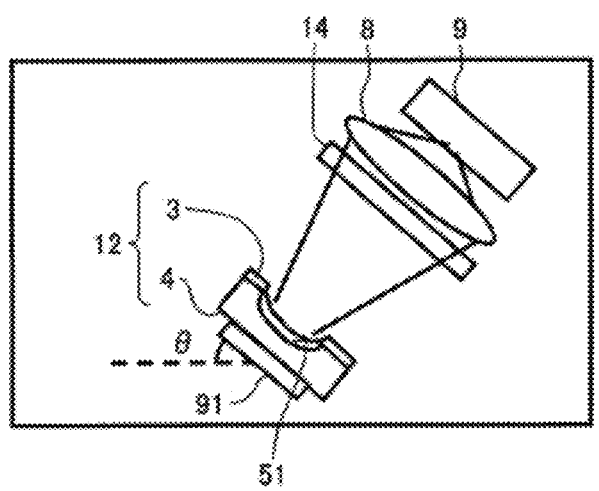
FIG. 9B is an illustration of a detecting mechanism in the detection apparatus.

An exemplary arrangement of light emitting element 6 and light receiving element 9 will be described with reference to FIGS. 8A, 9A and 9B. FIG. 9A is a cross-sectional view of detection apparatus 100B viewed from the position of A-A of FIG. 8A in the direction of the arrow, and FIG. 9B is a cross-sectional view taken from the position of B-B of FIG. 9A in the direction of the arrow. For convenience of description, in these figures, collecting mechanism other than collecting jig 12 is not shown.

Referring to FIG. 9A, when viewed from the direction of arrow A (top surface) of FIG. 8A, light emitting element 6 and lens 7 are arranged at a right angle or approximately at a right angle to light receiving element 9 and collecting lens 8. The light from light emitting element 6, passing through lens 7 and aperture 13 and reflected from irradiation region 15 formed on the surface of collecting jig 12 proceeds in the direction along the incident light. Therefore, by such a structure, direct entrance of the reflected light to light receiving element 9 is avoided. The fluorescence emitted from the surface of collecting jig 12 is isotropic and, therefore, the arrangement is not limited to the above as long as the entrance of reflected light and stray light to light receiving element 9 can be prevented.

More preferably, collecting jig 12 is provided with a configuration for collecting fluorescence emitted from particles trapped on the surface corresponding to irradiation region 15 to light receiving element 9. Such a configuration corresponds, for example, to a spherical recess 51 shown in FIG. 9B. Further, preferably, collecting jig 12 is provided inclined by an angle θ in a direction to light receiving element 9 so that the surface of collecting jig 12 faces light receiving element 9. By such a configuration, the fluorescence isotropically emitted from the particles in spherical recess 51 is reflected on the spherical surface and effectively collected in the direction to light receiving element 9, whereby the light receiving signal can be intensified. Though the size of recess 51 is not limited, preferably, it is made larger than irradiation region 15.

Again referring to FIG. 8A, light receiving element 9 is connected to signal processing unit 30 and outputs a current signal in proportion to the intensity of received light to signal processing unit 30. Therefore, fluorescence emitted from the particles that have been suspended in the introduced air, collected to the surface of collecting jig and irradiated with light from light emitting element 6, is received by light receiving element 9 and the intensity of received light is detected by signal processing unit 30.

Further, inlet 10 and outlet 11 of case 5 are provided with shutters 16A and 16B, respectively. Shutters 16A and 16B are connected to detecting unit 40 and have their opening/closing controlled. When shutters 16A and 16B are closed, air flow and entrance of external light to case 5 are blocked. Detecting unit 40 closes shutters 16A and 16B at the time of fluorescence measurement as will be described later, to block air flow and entrance of external light to case 5. Consequently, at the time of fluorescence measurement, collection of airborne particles by the collecting mechanism is stopped. Further, since entrance of external light to case 5 is blocked, stray light in case 5 can be reduced. Provision of only one of shutters 16A and 16B, for example, only shutter 16B on the side of outlet 11 may suffice.

Figure 10A:
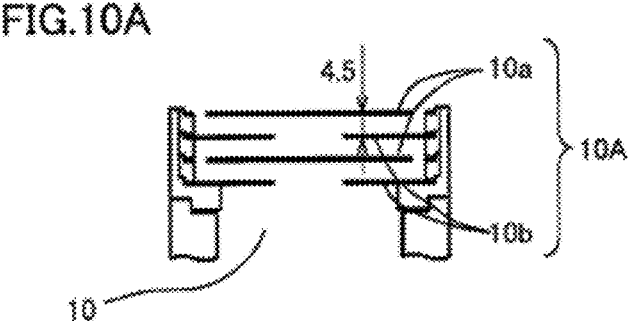
FIG. 10A is an illustration of a mechanism provided at an inlet as another specific example of a light intercepting mechanism in the detecting mechanism in accordance with the second example.
Figure 10B:
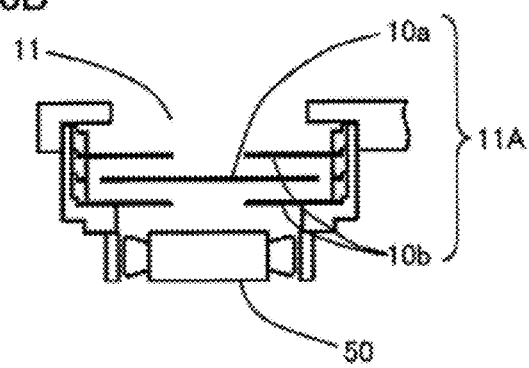
FIG. 10B is an illustration of a mechanism provided at an outlet as another specific example of the light intercepting mechanism in the detecting mechanism in accordance with the second example.

Further, as a configuration allowing air flow to/from case 5 but intercepting entrance of external light, light shielding portions 10A and 11A such as shown in FIGS. 10A and 10B, may be provided on inlet 10 and outlet 11.

Figure 10C:
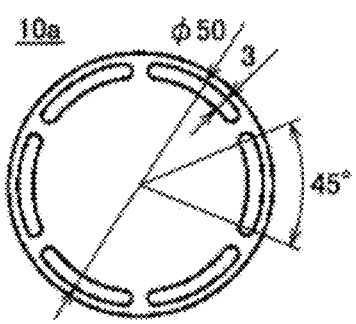
FIG. 10C shows a specific example of one of light shielding plates included in each of the mechanisms provided at the inlet and outlet as another specific example of the light intercepting mechanism in the detecting mechanism in accordance with the second example.
Figure 10D:
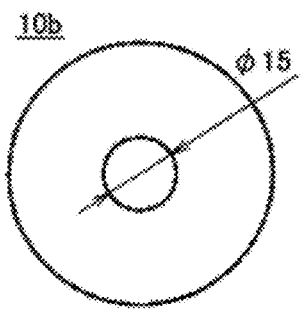
FIG. 10D shows another specific example of one of light shielding plates included in each of the mechanisms provided at the inlet and outlet as another specific example of the light intercepting mechanism in the detecting mechanism in accordance with the second example.

Referring to FIGS. 10A and 10B, light shielding portions 10A and 11A provided on inlet 10 and outlet 11 both have light shielding plates 10a and 10b overlapped alternately at an interval of about 4.5 mm. Light shielding plates 10a and 10b have holes formed therein at portions not overlapping with each other, with the shape of holes corresponding to the shape of inlet 10 and outlet 11 (here, circular shape), such as shown in FIGS. 10C and 10D, respectively. Specifically, light shielding plate 10a has holes opened at the circumferential portions, and light shielding plate 10b has a hole opened at the center. When light shielding plates 10a and 10b are overlapped, the holes formed in respective plates do not overlap. As shown in FIG. 10A, in light shielding portion 10A for inlet 10, light shielding plate 10a, light shielding plate 10b, light shielding plate 10a and light shielding plate 10b are arranged in this order from the outer side to the inner side. As shown in FIG. 10B, in light shielding portion 11A for outlet 11, light shielding plate 10b, light shielding plate 10a and light shielding plate 10b are arranged in this order from the outside (on the side of introducing mechanism 50) to the inside. By this configuration, though air flow to/from case 5 is possible, entrance of external light is intercepted, and stray light in case 5 can be reduced.

Here, the principle of detection in the detection apparatus 100B will be described.

As disclosed in Japanese Patent Laying-Open No. 2008-508527, it has been conventionally known that when airborne microorganisms are irradiated with ultraviolet or blue light, the particles emit fluorescence. In the air, however, other particles that emit fluorescence such as dust and lint of chemical fiber are also suspended. Therefore, it is impossible by simply detecting fluorescence to distinguish whether the light comes from microorganisms or from, for example, dust of chemical fiber.

In view of the foregoing, the inventors conducted heat treatment on microorganisms and on dust of chemical fiber and the like, and measured changes in fluorescence before and after heating. FIGS. 11 to 17 show specific results of measurement by the inventors. From the measurement results, the inventors found that the fluorescence intensity from dust did not change before and after heating, while fluorescence intensity emitted from microorganisms increased after heating.

Figure 11:
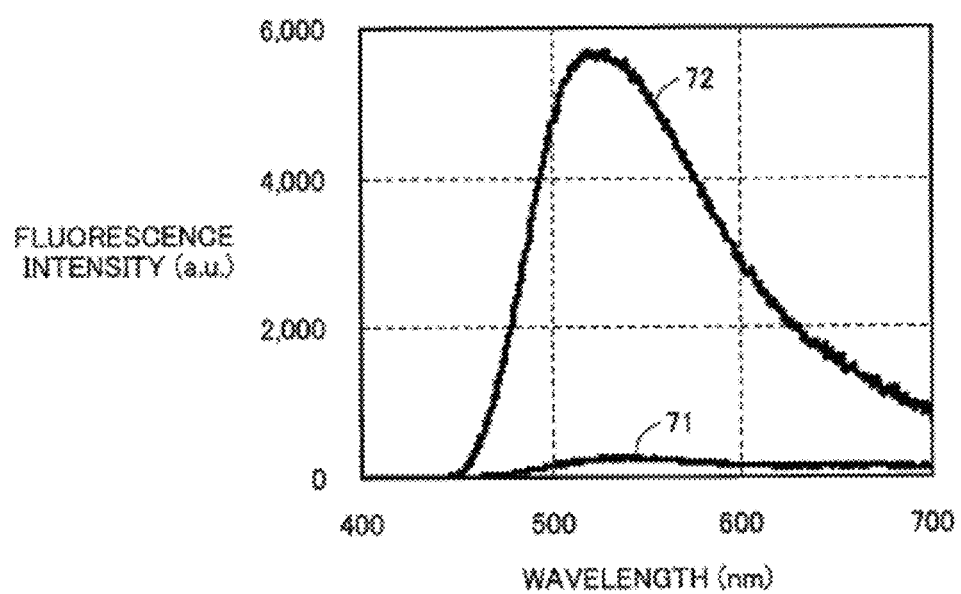
FIG. 11 shows time change of fluorescent spectrum of *Escherichia coli* before and after heat treatment.
Figure 12A:
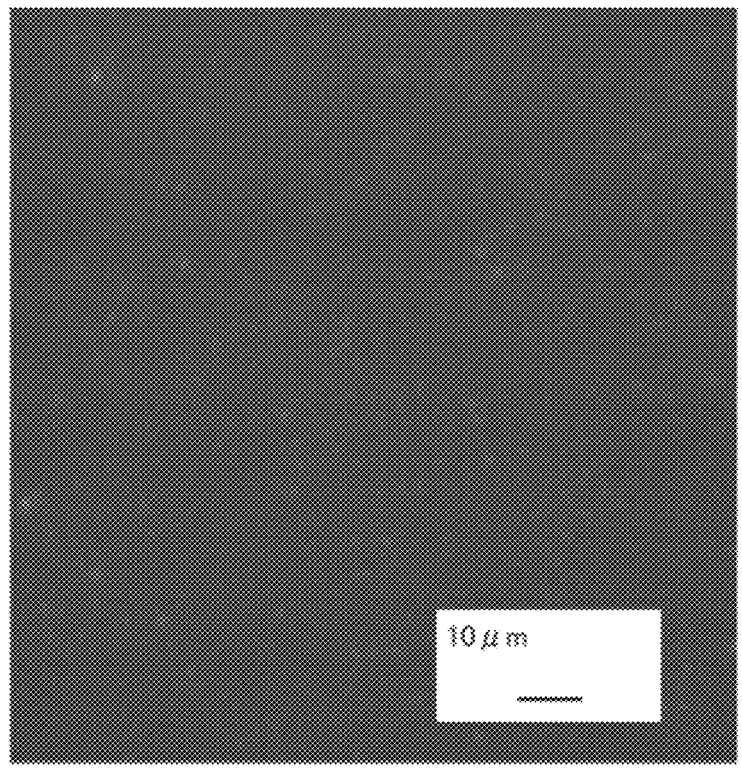
FIG. 12A is a fluorescent micrograph of *Escherichia coli* before heat treatment.
Figure 12B:
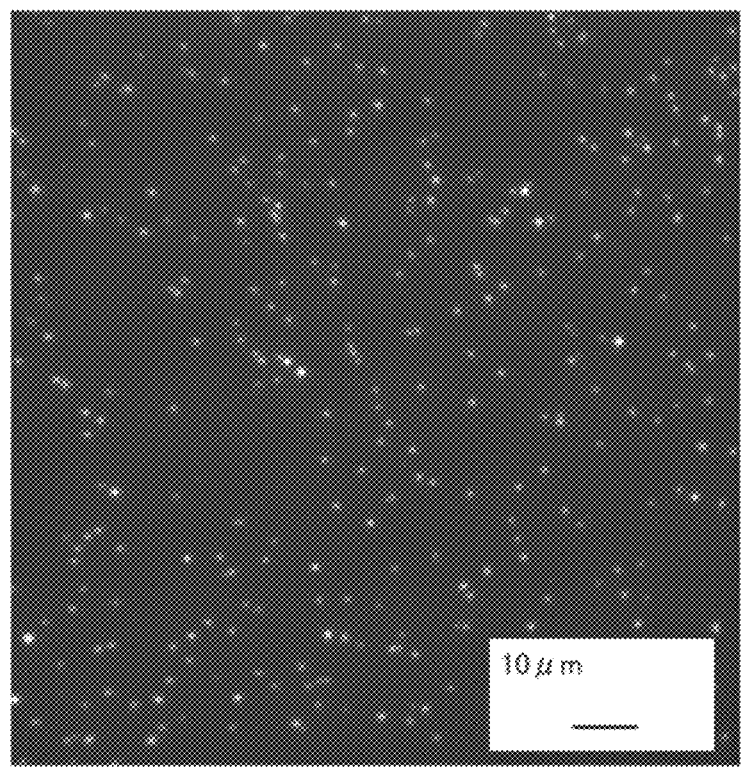
FIG. 12B is a fluorescent micrograph of *Escherichia coli* after heat treatment.

More specifically, FIG. 11 shows results of measurement of fluorescent spectra before (curve 71) and after (curve 72) heat treatment of *Escherichia coli* as biological particles at 200° C. for 5 minutes. From the results of measurement shown in FIG. 11, it can be seen that the fluorescence intensity from *Escherichia coli* increased significantly by the heat treatment. It is also apparent from the comparison between a fluorescent micrograph of *Escherichia coli* before heat treatment of FIG. 12A and a fluorescent micrograph of *Escherichia coli* after heat treatment of FIG. 12B that the fluorescence intensity from *Escherichia coli* increased significantly by the heat treatment.

Figure 13:
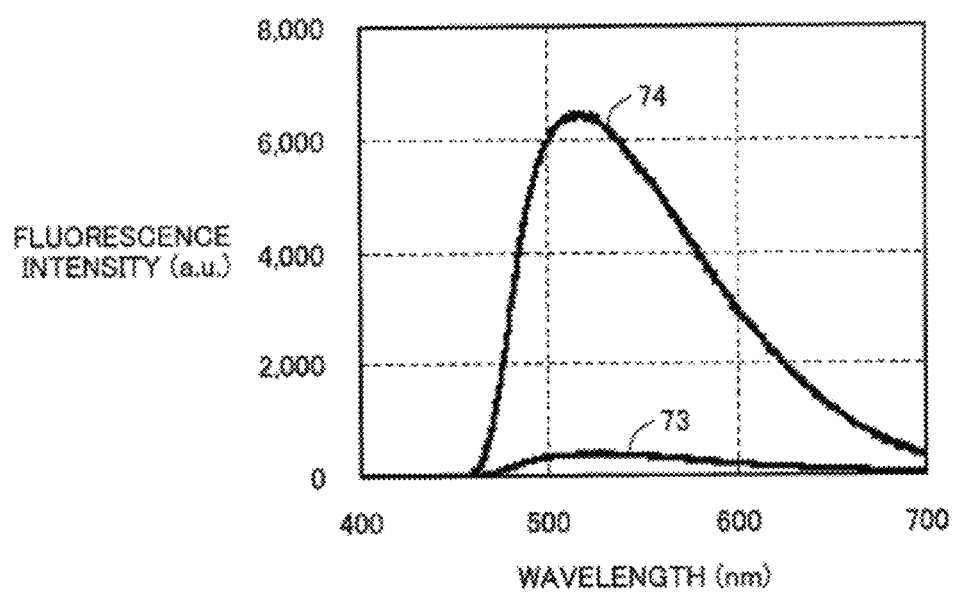
FIG. 13 shows time change of fluorescent spectrum of *Bacillius subtilis* before and after heat treatment.
Figure 14A:
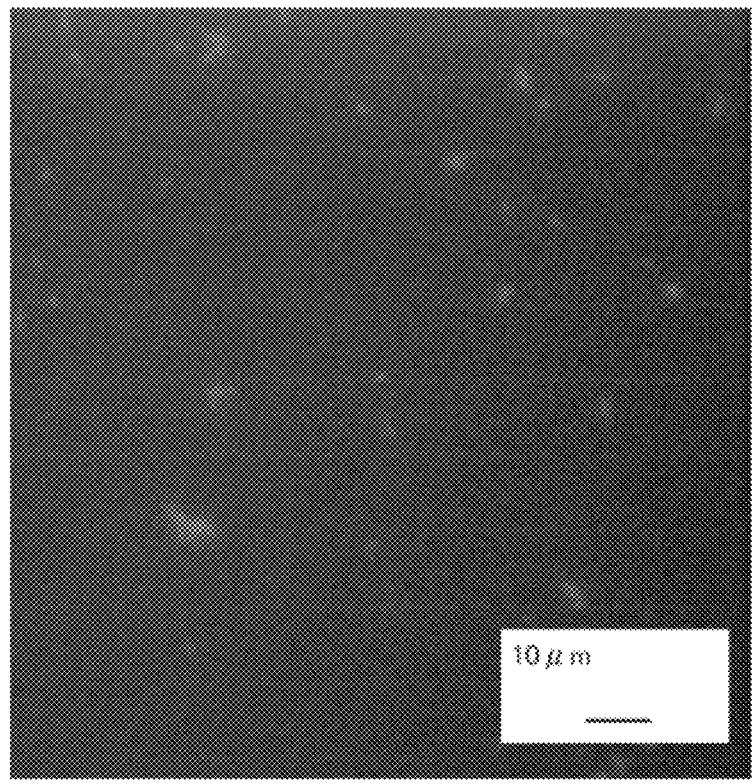
FIG. 14A is a fluorescent micrograph of *Bacillius subtilis* before heat treatment.
Figure 14B:
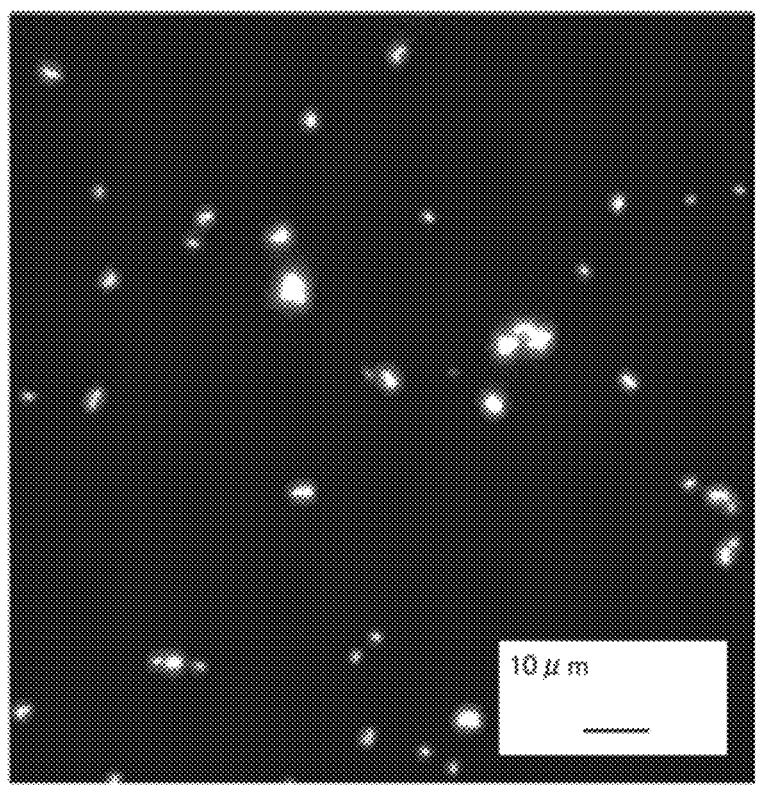
FIG. 14B is a fluorescent micrograph of *Bacillius subtilis* after heat treatment.
Figure 15:
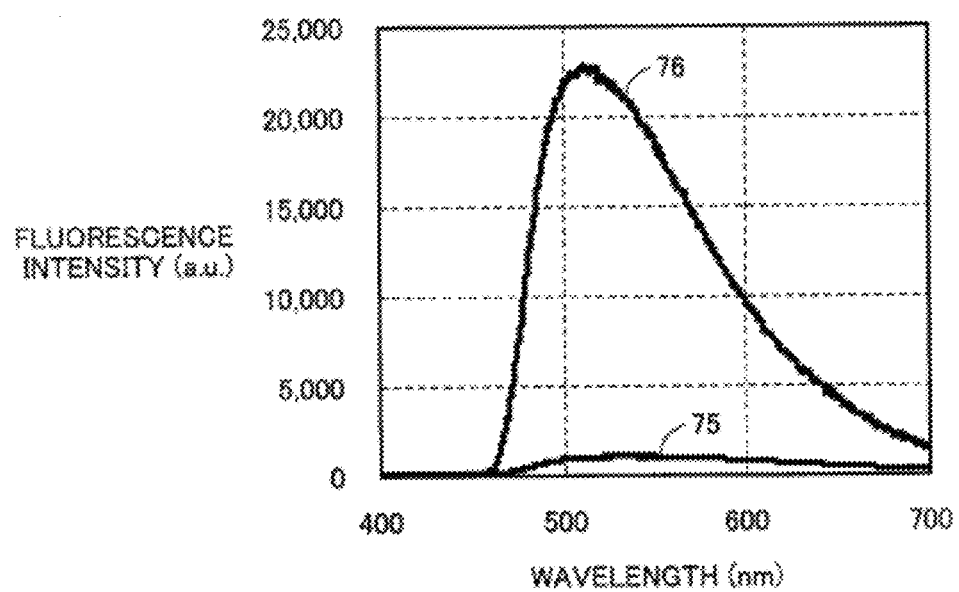
FIG. 15 shows time change of fluorescent spectrum of *Penicillium* before and after heat treatment.
Figure 16A:
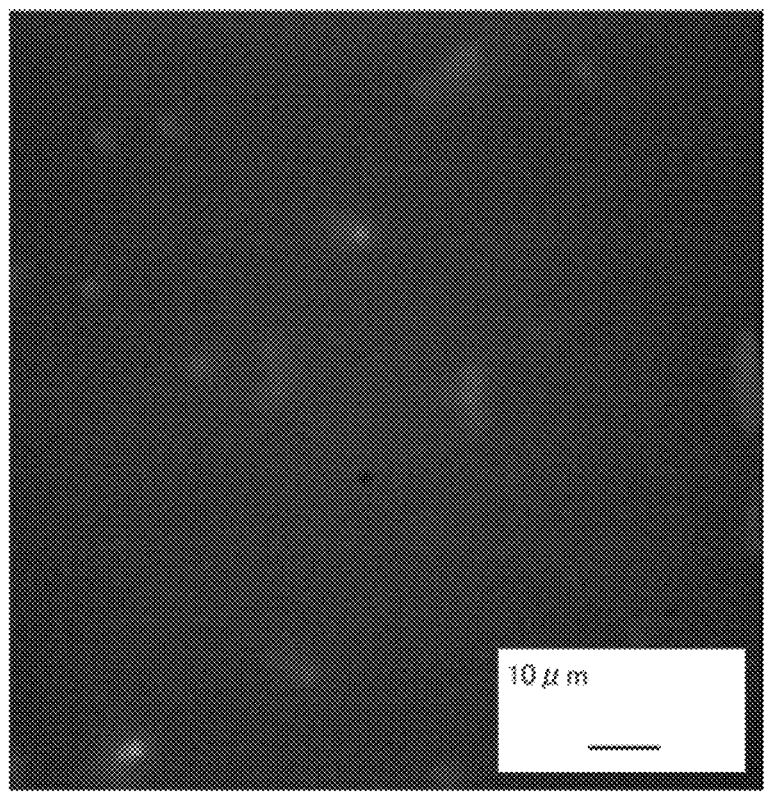
FIG. 16A is a fluorescent micrograph of *Penicillium* before heat treatment.
Figure 16B:
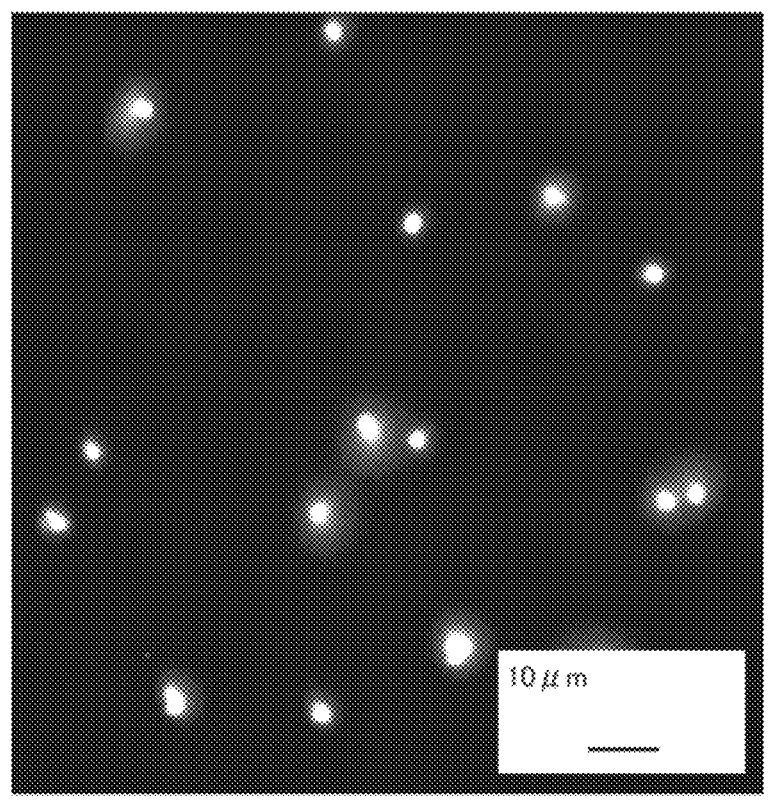
FIG. 16B is a fluorescent micrograph of *Penicillium* after heat treatment.
Figure 17A:
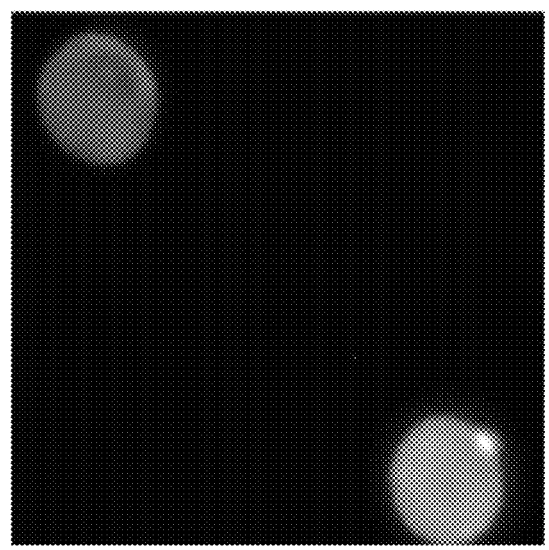
FIG. 17A is a fluorescent micrograph of cedar pollen before heat treatment.
Figure 17B:
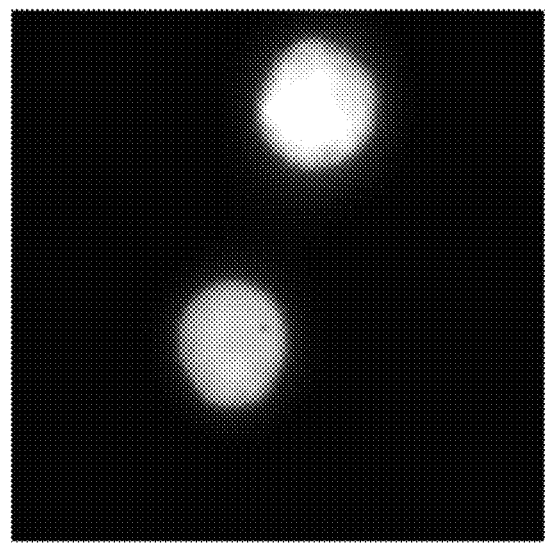
FIG. 17B is a fluorescent micrograph of cedar pollen after heat treatment.

Similarly, FIG. 13 shows results of measurement of fluorescent spectra before (curve 73) and after (curve 74) heat treatment of *Bacillius subtilis* as biological particles at 200° C. for 5 minutes, and FIG. 14A is a fluorescent micrograph before heat treatment and FIG. 14B is a fluorescent micrograph after heat treatment. FIG. 15 shows results of measurement of fluorescent spectra before (curve 75) and after (curve 76) heat treatment of *Penicillium* as biological particles at 200° C. for 5 minutes, and FIG. 16A is a fluorescent micrograph before heat treatment and FIG. 16B is a fluorescent micrograph after heat treatment. Furthermore, FIGS. 17A and 17B are fluorescent micrographs of cedar pollen as particles of biological origin before and after heat treatment, respectively, at 200° C. for five minutes. As can be seen from these results, as in the case of *Escherichia coli*, the fluorescence intensity from particles of a different biological origin is also increased significantly by the heat treatment.

Figure 18A:
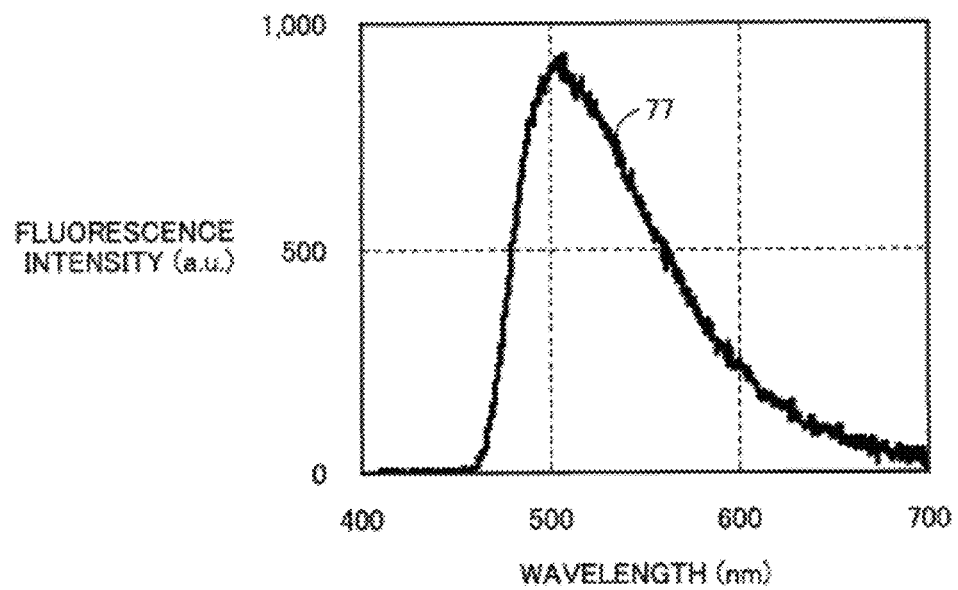
FIG. 18A shows time change of fluorescent spectrum of fluorescence-emitting dust before heat treatment.
Figure 18B:
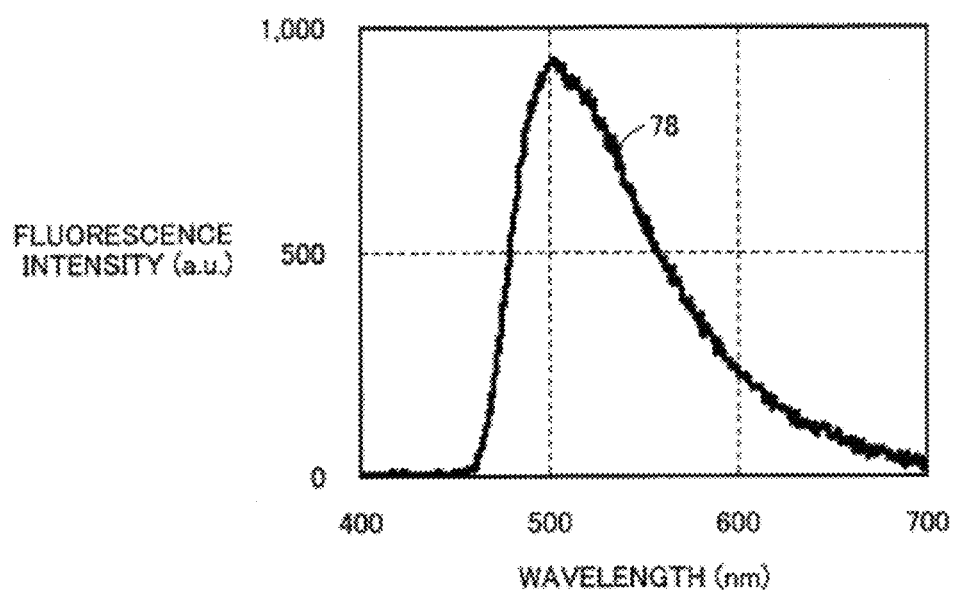
FIG. 18B shows time change of fluorescent spectrum of fluorescence-emitting dust after heat treatment.
Figure 19A:
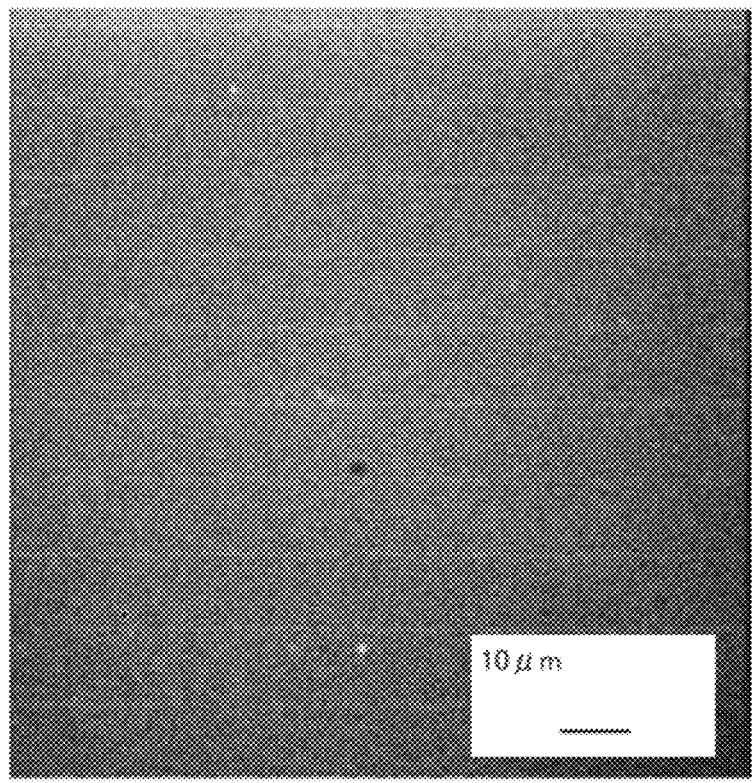
FIG. 19A is a fluorescent micrograph of fluorescence-emitting dust before heat treatment.
Figure 19B:
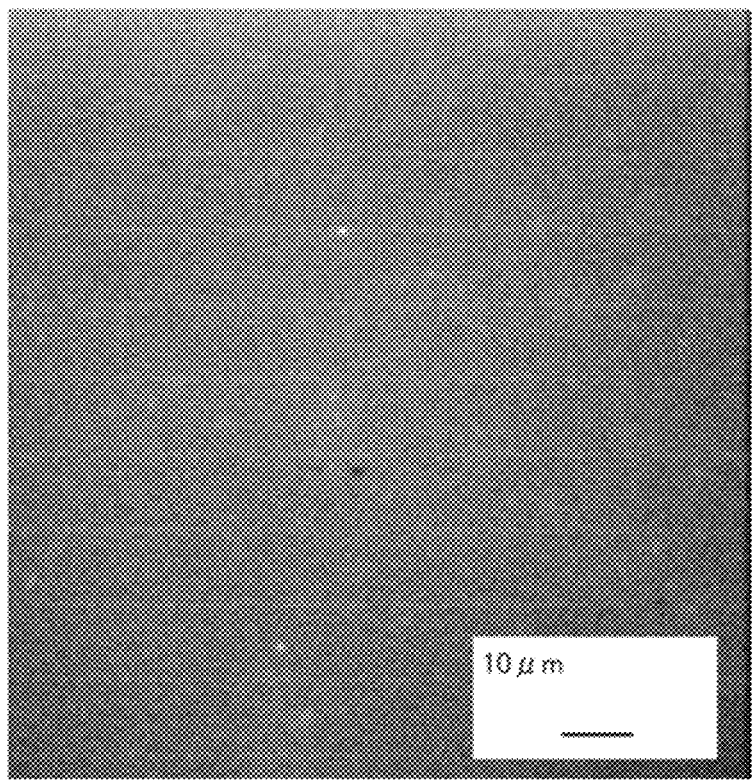
FIG. 19B is a fluorescent micrograph of fluorescence-emitting dust after heat treatment.
Figure 20:
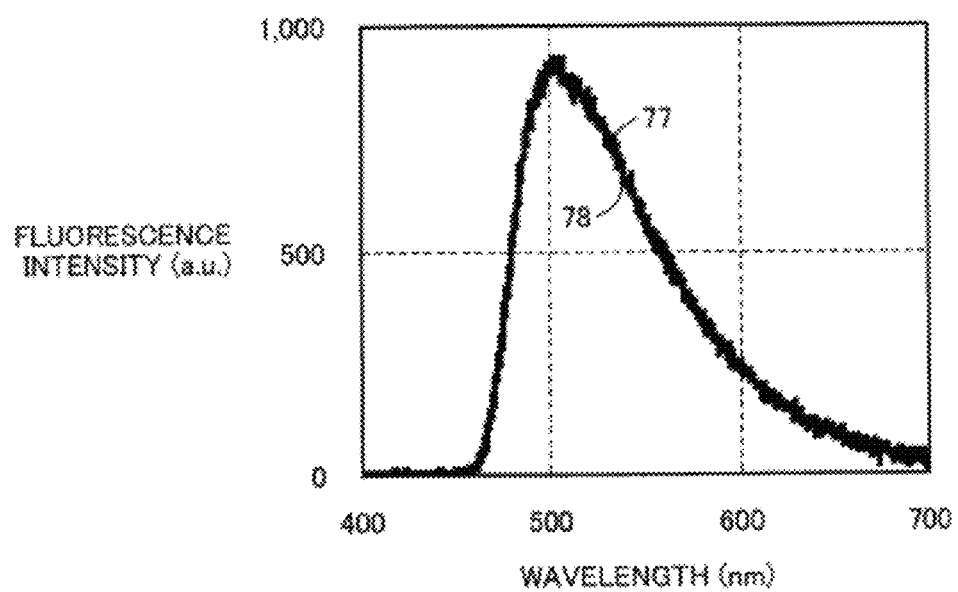
FIG. 20 shows results of comparison of fluorescent spectra of fluorescence-emitting dust before and after heat treatment.

In contrast, FIGS. 18A and 18B show results of measurement of fluorescent spectra before (curve 77) and after (curve 78) heat treatment of fluorescence-emitting dust at 200° C. for 5 minutes, and FIG. 19A is a fluorescent micrograph before heat treatment and FIG. 19B is a fluorescent micrograph after heat treatment. Placing the fluorescent spectrum of FIG. 18A on the fluorescent spectrum of FIG. 18B, we obtain FIG. 20, from which it can be verified that these spectra substantially overlap with each other. Specifically, from the result of FIG. 20 and from the comparison between FIGS. 19A and 19B, it can be seen that the fluorescence intensity from dust does not change before and after heat treatment.

As the principle of detection in detection apparatus 100B, the above-described phenomenon verified by the inventors is applied. Specifically, dust, dust with microorganisms adhered, and microorganisms are suspended in the air. From the phenomenon described above, it follows that if collected particles include fluorescence-emitting dust, the fluorescent spectra measured before heat treatment include fluorescence from microorganisms and fluorescence from fluorescence-emitting dust and, therefore, it is impossible to distinguish microorganisms from, for example, dust of chemical fiber. By the heat treatment, however, the fluorescence intensity from only the microorganisms increases, while the fluorescence intensity from fluorescence-emitting dust does not change. Therefore, by measuring the difference of fluorescence intensity before heat treatment and fluorescence intensity after prescribed heat treatment, it is possible to find the amount of microorganisms.

Figure 21:
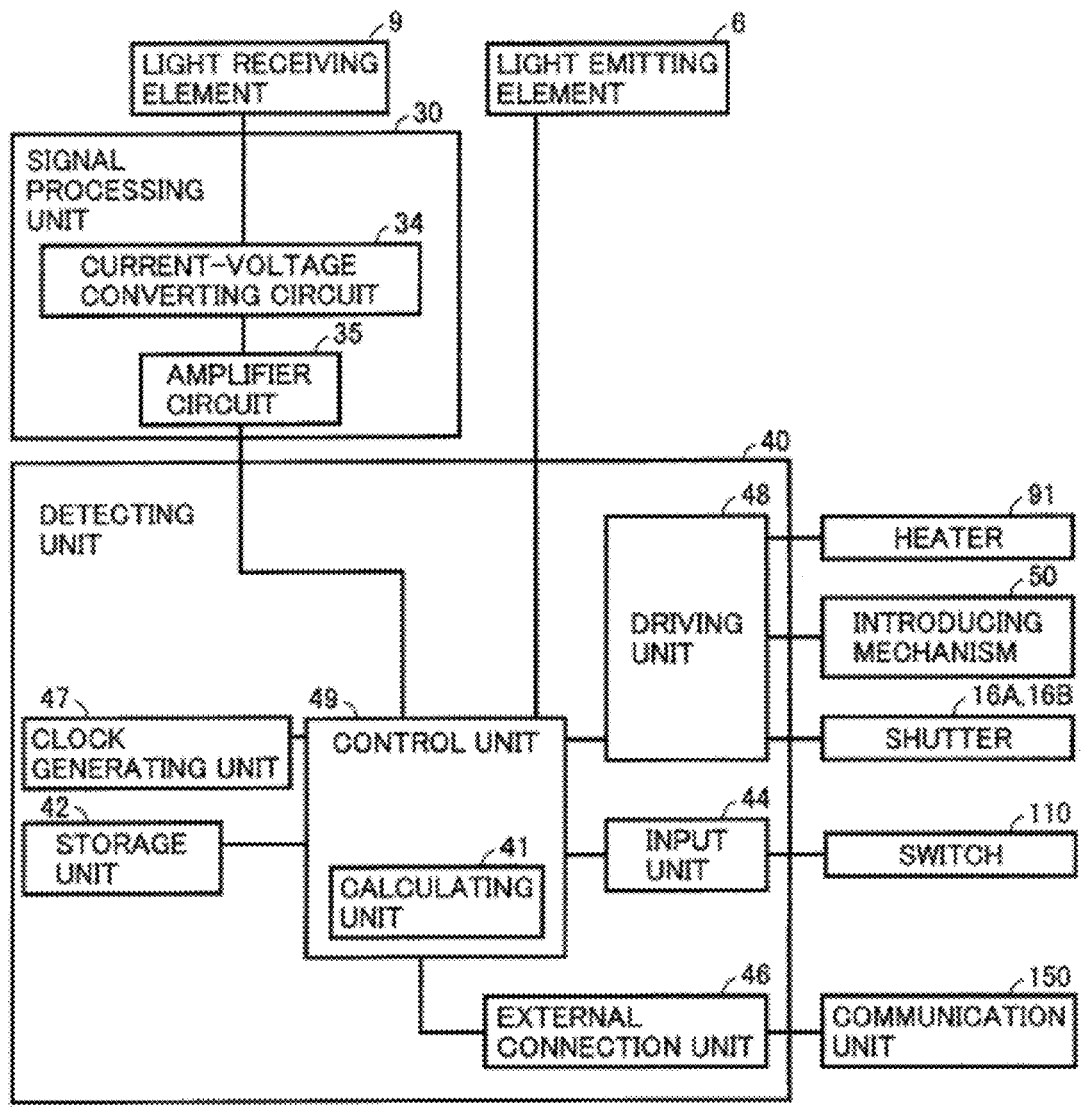
FIG. 21 is a block diagram showing an exemplary functional configuration of the detection apparatus in accordance with a third example, included in the air purifier.

FIG. 21 is a block diagram showing a specific example of the functional configuration of detection apparatus 100B for detecting airborne microorganisms utilizing the principle above. FIG. 21 again shows an example in which the functions of signal processing unit 30 are implemented by hardware configuration mainly of electric circuitry. It is noted, however, that at least part of the functions may be implemented by software configuration realized by a CPU, not shown, provided in signal processing unit 30, executing a prescribed program. Further, in the example shown, detecting unit 40 is implemented by software configuration. At least part of the functions thereof may be realized by hardware configuration such as electric circuitry.

Referring to FIG. 21, signal processing unit 30 includes a current-voltage converting circuit 34 connected to light receiving element 9, and an amplifying circuit 35 connected to current-voltage converting circuit 34.

Detecting unit 40 includes a control unit 49, a storage unit 42, and a clock generating unit 47. Further, detecting unit 40 includes: an input unit 44 for receiving input of information by receiving an input signal from switch 110 upon operation of switch 110; an external connection unit 46 performing processes required for exchanging data and the like with an external apparatus connected to communication unit 150; and a driving unit 48 for driving shutters 16A and 16B, introducing mechanism 50 and heater 91.

When particles introduced to case 5 and collected on collecting jig 12 are irradiated with light from light emitting element 6, fluorescence emitted from the particles in the irradiation region is collected at light receiving element 9. Light receiving element 9 outputs a current signal in accordance with the amount of received light to signal processing unit 30. The current signal is input to current-voltage converting circuit 34.

Current-voltage converting circuit 34 detects a peak current value H representing the fluorescence intensity from the current signal input from light receiving element 9, and converts it to a voltage value Eh. The voltage value Eh is amplified by amplifying circuit 35 by a preset gain, and the result is output to detecting unit 40. Control unit 49 of detecting unit 40 receives the input of voltage value Eh from signal processing unit 30 and successively stores in storage unit 42.

Clock generating unit 47 generates and outputs clock signals to control unit 49. With the timing based on the clock signals, control unit 49 outputs control signals for opening and closing shutters 16A and 16B to driving unit 48, to control opening/closing of shutters 16A and 16B. Further, control unit 49 is electrically connected to light emitting element 6 and light receiving element 9, and controls ON/OFF of these elements.

Figure 22:
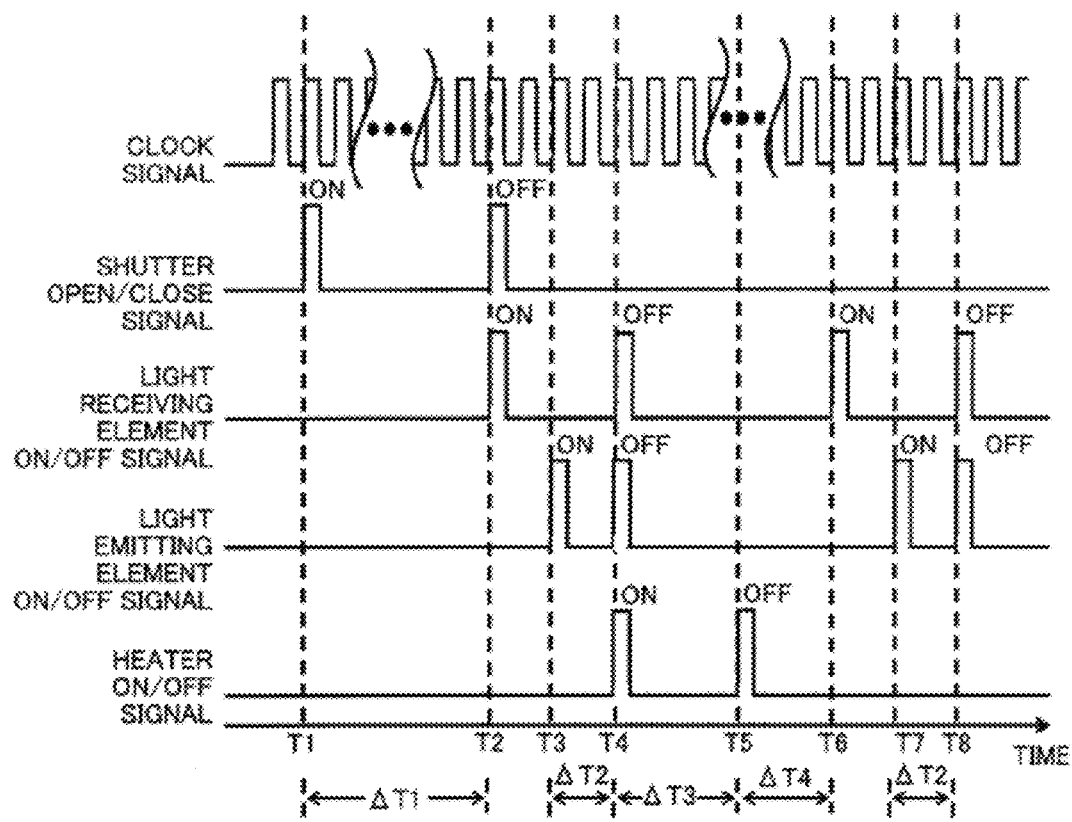
FIG. 22 is a time-chart showing a flow of operations in the detection apparatus in accordance with the third example.

Control unit 49 includes a calculating unit 41. Calculating unit 41 operates to calculate the amount of microorganisms suspended in the introduced air, using the voltage value Eh stored in storage unit 42. Specific operation will be described using a time chart of FIG. 22, showing the flow of control by control unit 49. Here, as the amount of microorganisms, it is assumed that concentration of microorganisms suspended in the air introduced to case 5 is calculated.

Referring to FIG. 22, when detection apparatus 100B is powered ON, control unit 49 of detecting unit 40 outputs a control signal to driving unit 48, to drive introducing mechanism 50. Further, at a time point T1 based on the clock signal from clock generating unit 47, control unit 49 outputs a control signal for opening (ON) shutters 16A and 16B to driving unit 48. Then, at time point T2 after the lapse of ΔT1 from T1, control unit 49 outputs a control signal for closing (OFF) shutters 16A and 16B to driving unit 48.

Thus, for the time period ΔT1 from T1, shutters 16A and 16B are opened, and as introducing mechanism 50 is driven, external air is introduced through inlet 10 to case 5. Particles suspended in the air introduced to case 5 are negatively charged by discharge electrode 17, and by the air flow and an electric field formed between discharge electrode 17 and coating 3 on the surface of collecting jig 12, the particles are collected on the surface of collecting jig 12 for the time period ΔT1.

At time point T2, shutters 16A and 16B are closed, so that the air flow in case 5 stops. Thus, collection of airborne particles by collecting jig 12 ends. Further, stray light from the outside is blocked.

At time point T2 when shutters 16A and 16B are closed, control unit 49 outputs a control signal to light receiving element 9 to start reception of light (ON). At the same time (T2) or at T3 slightly after T2, it outputs a control signal to light emitting element 6 to start emission of light (ON). Thereafter, at time point T4 after the lapse of ΔT2, which is a predetermined measurement time for measuring fluorescence intensity, from time T3, control unit 49 outputs a control signal to light receiving element 9 to stop reception of light (OFF) and a control signal to light emitting element 6 to stop emission of light (OFF). The measurement time may be set in advance in control unit 49, or it may be input or changed by an operation of, for example, switch 110, by a signal from PC 300 connected to communication unit 150 through cable, or by a signal from a recording medium attached to communication unit 150.

Specifically, from time point T3 (or from T2), emission of light from light emitting element 6 starts. The light from light emitting element 6 is directed to irradiation region 15 on the surface of collecting jig 12, and fluorescence is emitted from collected particles. Fluorescence is received by light receiving element 9 for the predetermined measuring time ΔT2 from time T3, and a voltage value in accordance with the fluorescence intensity F1 is input to detecting unit 40 and stored in storage unit 42.

At this time, a separate light emitting element such as an LED (not shown) may be provided, light emitted from this element and reflected from a reflection region (not shown), at which particles are not collected, on the surface of collecting jig 12 may be collected by a separate light receiving element (not shown), the intensity of received light may be used as a reference value I0 and the value F1/I0 may be stored in storage unit 42. By calculating the ratio to reference value I0, it becomes advantageously possible to compensate for the fluctuation of fluorescence intensity derived from environmental conditions such as moisture and temperature of light emitting element or light receiving element, or from variation in characteristics caused by deterioration or aging.

At time point T4 (or a time point slightly later than T4) when emission of light by light emitting element 6 and reception of light by light receiving element 9 are stopped, control unit 49 outputs a control signal to heater 91 to start heating (ON). Thereafter, at time point T5 after the lapse of $\Delta T3$, which is a predetermined heating time for the heat treatment, from the start of heating by heater 91 (from time point T4 or a time point slightly later than T4), control unit 49 outputs a control signal to heater 91 to stop heating (OFF).

Thus, for the time period $\Delta T3$ of heating from T4 (or a time point slightly later than T4), heat treatment is done on the particles collected in irradiation region 15 on the surface of collecting jig 12, by heater 91. The heating temperature at this time is determined in advance. By the heat treatment for the time period $\Delta T3$, the particles collected on the surface of collecting jig 12 are heated by prescribed heat inputs. As in the case of the measurement time described above, the time of heat treatment $\Delta T3$ (that is, the heat input) may be set in advance in control unit 49, or it may be input or changed by an operation of, for example, switch 110, by a signal from PC 300 connected to communication unit 150 through cable, or by a signal from a recording medium attached to communication unit 150.

Thereafter, for a time period $\Delta T4$, the heated particles are subjected to cooling. For the cooling process, introducing mechanism 50 may be used. In that case, external air may be taken in from an opening (not shown in FIG. 8A) provided with an HEPA (High Efficiency Particulate Air) filter. Alternatively, a separate cooling mechanism such as a Peltier device may be used.

Thereafter, control unit 49 outputs a control signal to end the operation of introducing mechanism 50, and at time T6, outputs a control signal to light receiving element 9 to start reception of light (ON). At the same time (T6) or at time T7 slightly later than T6, it outputs a control signal to light emitting element 6 to start emission of light (ON). Thereafter at time point T8 after the lapse of $\Delta T2$ from T7, control unit 49 outputs a control signal to light receiving unit 9 to stop reception of light (OFF) and a control signal to light emitting element 6 to stop emission of light (OFF).

In this manner, after heat treatment for the time period $\Delta T3$, from the particles collected in irradiation region 15 on the surface of collecting jig 12 irradiated by light emitting element 6, the fluorescence for the measurement time $\Delta T2$ is received by light receiving element 9. The voltage value corresponding to the fluorescence intensity F2 is input to detecting unit 40 and stored in storage unit 42.

Figure 23:
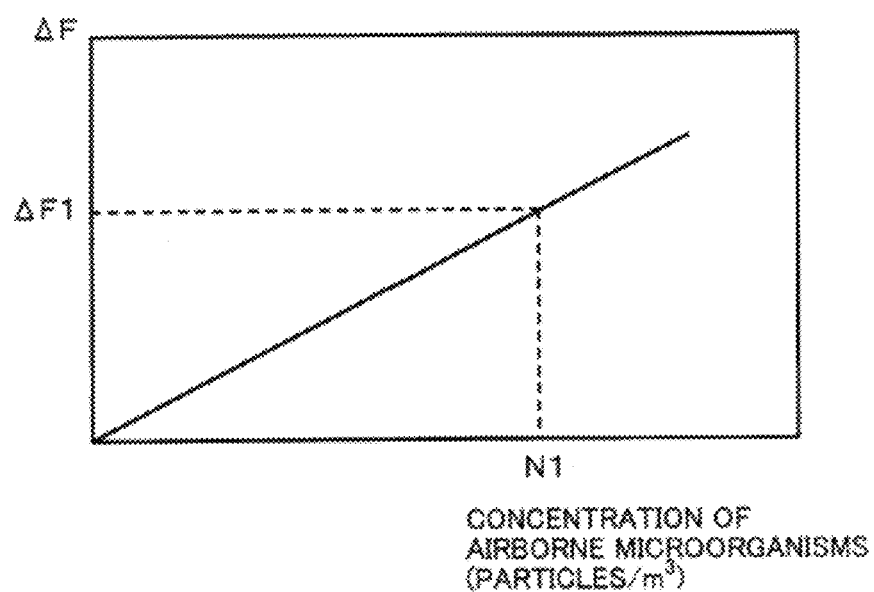
FIG. 23 is a graph showing specific relation between fluorescence decay and microorganism concentration.

Calculating unit 41 calculates a difference between the stored fluorescence intensity F1 and fluorescence intensity F2 as an amount of increase $\Delta F$. As described above, the amount of increase $\Delta F$ relates to the amount of microorganisms (the number or concentration of microorganisms). Calculating unit 41 stores beforehand the correspondence between the amount of increase $\Delta F$ and the amount of microorganisms (the concentration of particles) such as shown in FIG. 23. Then, calculating unit 41 provides the concentration of microorganisms, obtained by using the amount of increase $\Delta F$ and the correspondence relation, as the concentration of microorganisms in the air introduced to case 5 in time period $\Delta T1$.

The correspondence relation between the amount of increase $\Delta F$ and the concentration of microorganisms is experimentally determined in advance. By way of example, one type of microorganism such as *Escherichia coli*, *Bacillius subtilis* or *Penicillium* is sprayed using a nebulizer in a vessel having the size of 1 m³. While the concentration of microorganisms is kept at N (particles/m³), the microorganisms are collected using detection apparatus 100B by the method of detection described above for the time period $\Delta T1$. Then, the collected microorganisms are heated by a prescribed heat input (heating time $\Delta T3$, prescribed heating temperature) using heater 91, cooled for a prescribed time period $\Delta T4$, and the amount of increase $\Delta F$ of fluorescence intensity before and after heating is measured. Similar measurements are made for various concentrations of microorganisms, whereby the relation between the amount of increase $\Delta F$ and the microorganism concentration (particles/m³) can be found as shown in FIG. 23.

The correspondence relation between the amount of increase $\Delta F$ and the concentration of microorganisms may be input by an operation of switch 110 or the like and stored in calculating unit 41. Alternatively, a recording medium having the correspondence relation recorded thereon may be attached to communication unit 150 and read by external connection unit 46 and stored in calculating unit 41. It may be input and transmitted by PC 300, received by external connection unit 46 through cable connected to communication unit 150, and stored in calculating unit 41. If communication unit 150 is adapted to infrared or Internet communication, the correspondence relation may be received by external connection unit 46 at communication unit 150 by such communication, and stored in calculating unit 41. Further, the correspondence relation once stored in calculating unit 41 may be updated by detecting unit 40.

If the amount of increase $\Delta F$ is calculated to be a difference $\Delta F1$, calculating unit 41 identifies a value corresponding to the increased amount $\Delta F1$ from the correspondence relation shown in FIG. 22, and thereby calculates the concentration N1 (particles/m³) of microorganisms.

It is noted, however, that the correspondence relation between the amount of increase $\Delta F$ and the microorganism concentration possibly differs depending on the type of microorganism (for examples, types of microbes). Therefore, calculating unit 41 defines some microorganism as standard microorganism and stores the correspondence relation between the amount of increase $\Delta F$ and the microorganism concentration. In this manner, microorganism concentration in various environments can be calculated as the microorganism concentration in equivalence of the standard microorganism, whereby environmental management becomes easier.

Though the difference in fluorescence intensity before and after heat treatment of a prescribed heat input (prescribed heating temperature, heating time $\Delta T3$) is used as the amount of increase $\Delta F$ in the embodiment above, the ratio thereof may be used.

The concentration of collected microorganisms calculated by calculating unit 41 is output from control unit 49 to display control unit 210.

In this manner, detection apparatus 100B utilizes difference in characteristics when heated between the fluorescence from microorganisms and the fluorescence from fluorescence-emitting dust, and based on the amount of increase after a prescribed heat treatment, microorganisms are detected. Specifically, detection apparatus 100B detects the microorganisms utilizing the phenomenon that when the collected microorganisms and dust are subjected to heat treatment, the fluorescence intensity from microorganisms increases whereas the fluorescence intensity from dust does not change. Therefore, even if fluorescence-emitting dust is suspended in the introduced air, it is possible to detect microorganisms separate from fluorescence-emitting dust on real-time basis with high accuracy.

Further, detection apparatus 100B is controlled in the manner as shown in FIG. 22 and thereby shutters 16A and 16B are closed at the transition from the collecting step by the collecting mechanism to the detection step by the detecting mechanism. As a result, stray light caused by scattering at airborne particles during fluorescence measurement can be reduced and measurement accuracy can be improved.

Third Example of the Detection Apparatus

Figure 24:
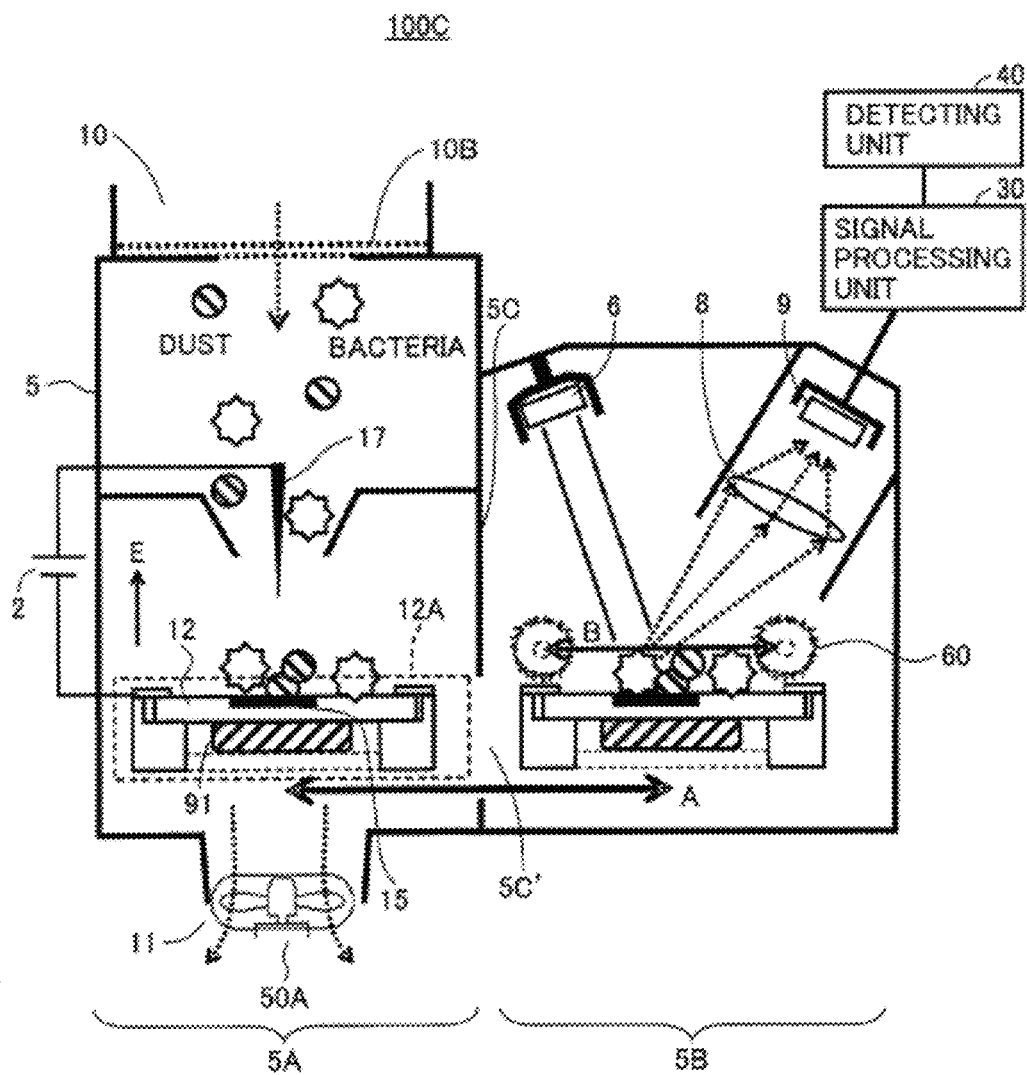
FIG. 24 shows a specific example of another basic configuration of a detection apparatus included in the air purifier.
Figure 25:
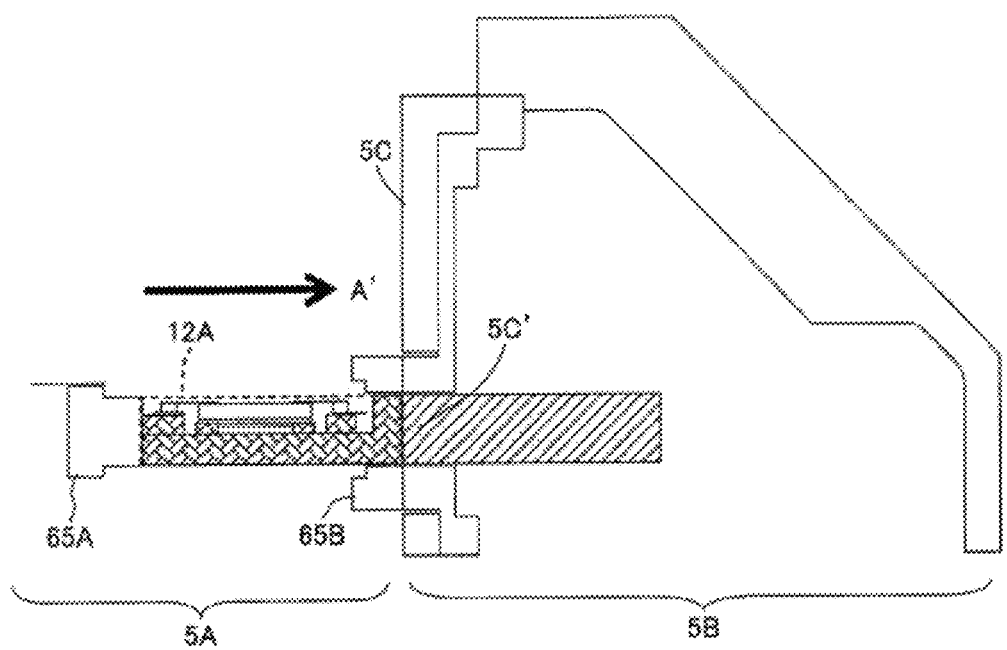
FIG. 25 is an illustration related to an operation of a collection unit of the detection apparatus in accordance with the third example.
Figure 26:
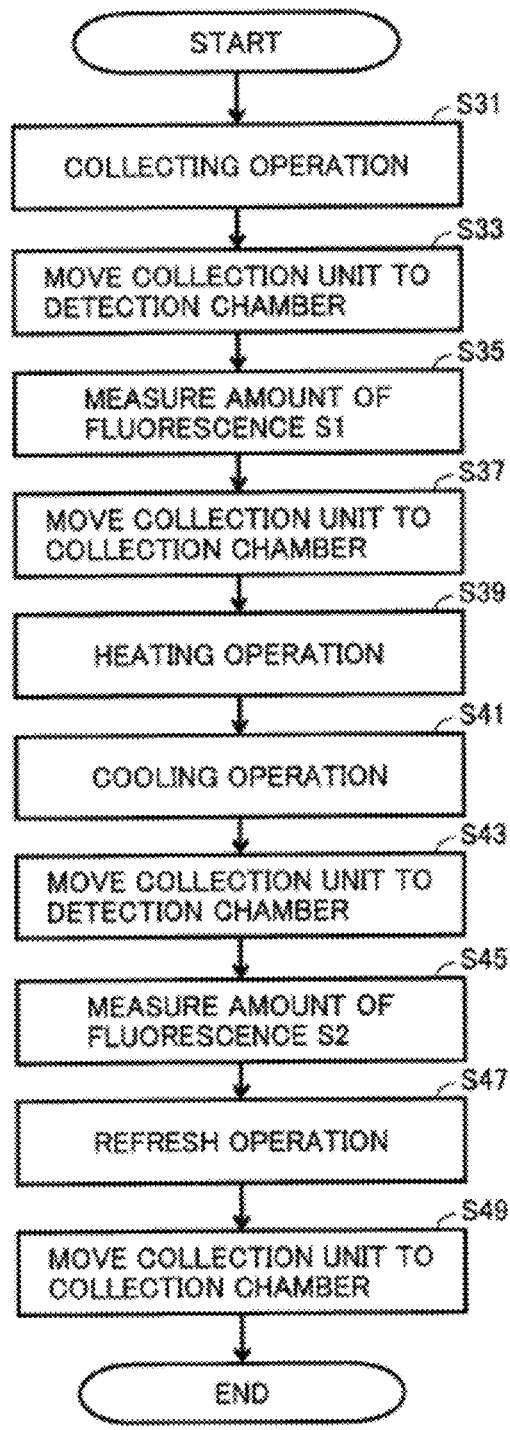
FIG. 26 is a time-chart showing a flow of operations in the detection apparatus in accordance with the third example.

FIG. 24 illustrates the third example of detection apparatus 100. The third example of detection apparatus 100 is a modification of detection apparatus 100B.

Referring to FIG. 24, a detection apparatus 100C in accordance with the third example includes a detecting mechanism, a collecting mechanism and a heating mechanism. In FIG. 24, members denoted by the same reference characters as in detection apparatus 100A in accordance with the first example and detection apparatus 100B in accordance with the second example are substantially the same as the corresponding members. In the following, the difference over detection apparatus 100B will be mainly described.

More specifically, referring to FIG. 24, detection apparatus 100C is provided with a collection chamber 5A including at least a part of the collecting mechanism, and a detection chamber 5B including the detecting mechanism, sectioned by a partition wall 5C having a hole 5C'. In collection chamber 5A, a needle-shaped discharge electrode 17 and collecting jig 12 as the collecting mechanism are provided, and in detection chamber 5B, light emitting element 6, light receiving element 9 and collecting lens 8 as the detecting mechanism are provided.

On the side of discharge electrode 17 and collecting jig 12 of collection chamber 5A, inlet 10 and outlet 11 are provided, respectively, for introducing air to collection chamber 5A. Further, as shown in FIG. 24, a filter (pre-filter) 10B may be provided at inlet 10.

Inlet 10 and outlet 11 may be provided with light shielding portions 10A and 11A such as shown in FIGS. 10A and 10B similar to those of detection apparatus 100B, for intercepting entrance of external light while allowing air flow to/from collection chamber 5A.

A fan 50A as the introducing mechanism is provided close to outlet 11. By fan 50A, the air is introduced from the inlet to collection chamber 5A. Preferably, the driving mechanism of fan 50A is controlled by detecting unit 40 such that flow rate of introduced air is regulated. Preferably, the flow rate of air introduced by fan 50A is 1 L (liter)/min to 50 m³/min. When driven by a driving mechanism, not shown, controlled by detecting unit 40, fan 50A introduces air outside collection chamber 5A through inlet 10 and discharges air in collection chamber 5A through outlet 11 to the outside of collection chamber 5A as shown by a dotted line arrow in the figure.

As the collecting mechanism, a collecting mechanism similar to that of detection apparatus 100B may be used. Specifically, referring to FIG. 24, the collecting mechanism includes discharge electrode 17, collecting jig 12, and high-voltage power supply 2. Discharge electrode 17 is electrically connected to the positive electrode of high-voltage power supply 2. Collecting jig 12 is electrically connected to a negative electrode of high-voltage power supply 2.

Collecting jig 12 is a support board formed, for example, of a glass plate, having a conductive, transparent coating, as in detection apparatus 100B. The coating side of collecting jig 12 is electrically connected to the negative electrode of high-voltage power supply 2. Thus, there is generated a potential difference between discharge electrode 17 and collecting jig 12, and an electric field in the direction indicated by an arrow E of FIG. 24 is formed.

Particles suspended in the air introduced through inlet 10 by the driving of fan 50A are negatively charged near discharge electrode 17. The negatively charged particles move toward collecting jig 12 because of electrostatic force, and are attracted and held by conductive coating, whereby the particles are collected on collecting jig 12. Here, since needle-shaped electrode is used as discharge electrode 17, it is possible to have charged particles attracted and held in a very narrow area corresponding to irradiation region 15 (as will be described later) irradiated by the light emitting element of collecting jig 12 opposite to discharge electrode 17. Consequently, in the detecting step as will be described later, it is possible to efficiently detect the attracted microorganisms.

The detecting mechanism included in detection chamber 5B includes: light emitting element 6 as a light source; light receiving element 9; and a collecting lens (or lenses) 8, provided in the direction of light reception by light receiving element 9, for collecting fluorescence generated by irradiation of airborne particles collected on collecting jig 12 by the collecting mechanism with light from light emitting element 6 to light receiving element 9. It may further include: a lens (or lenses) provided in a direction of light emission by light emitting element 6, for collimating the light beams from light emitting element 6 or to adjust the light beams to a prescribed width; an aperture; and a filter (or filters) for preventing entrance of irradiating light beam to light receiving element 9. Conventional configurations may be applied to these components. Collecting lens 8 may be formed of plastic resin or glass.

Preferably, at least the inner side of detection chamber 5B is painted black or treated with black alumite. This prevents reflection of light from the inner wall surface as a cause of stray light. Though the material of collection chamber 5A and detection chamber 5B is not specifically limited, preferably, plastic resin, metal such as aluminum or stainless steel, or a combination of these may be used. Inlet 10 and outlet 11 of case 5 have circular shape with the diameter of 1 mm to 50 mm. The shape of inlet 10 and outlet 11 is not limited to a circle, and it may be an ellipse or a rectangle.

Light emitting element 6 is similar to that of detection apparatus 100B. Light beams emitted from light emitting element 6 are collected on a surface of collecting jig 12, and form irradiation region 15 on collecting jig 12. The shape of irradiation region 15 is not specifically limited, and it may have a circular, elliptical or rectangular shape. Though the size of irradiation region 15 is not specifically limited, preferably, the diameter of a circle, the longer side length of an ellipse or the length of one side of a rectangle is in the range of about 0.05 mm to 50 mm.

Light receiving element 9 is connected to signal processing unit 30 and outputs a current signal in proportion to the intensity of received light to signal processing unit 30. Therefore, fluorescence emitted from the particles that have been suspended in the introduced air, collected to the surface of collecting jig 12 and irradiated with light from light emitting element 6, is received by light receiving element 9 and the intensity of received light is detected by signal processing unit 30.

A brush 60 for refreshing the surface of collecting jig 12 is provided at a position to touch the surface of collecting jig 12 in detection chamber 5B. Brush 60 is connected to a moving mechanism, not shown, controlled by detecting unit 40 and reciprocates on collecting jig 12 as represented by a double-sided arrow B in the figure. Consequently, dust and microorganisms deposited on collecting jig 12 are removed.

Preferably, heater 91 is arranged on that surface of collecting jig 12 which is away from discharge electrode 17, as shown in FIG. 24.

A unit including collecting jig 12 and heater 91 will be referred to as a collection unit 12A here. Collection unit 12A is connected to a moving mechanism, not shown, controlled by detecting unit 40, and moves as indicated by double-sided arrow A in the figure, that is, from collection chamber 5A to detection chamber 5B and from detection chamber 5B to collection chamber 5A, through hole 5C' formed in wall 5C. As already described, heater 91 may be arranged at a position all chamber 5B to collection chamber 5A. When the movement ends, at step S39, heating operation is done. At step S39, as in detection apparatus 100B, control unit 49 causes heater 91 to heat for the predetermined heating time ΔT3. The heating temperature at this time is determined beforehand.

After the heating operation, at step S41, a cooling operation takes place. At step S41, control unit 49 outputs a control signal to driving unit 48 to cause fan 50A to rotate in reverse direction for a prescribed cooling time. Collection unit 12A is cooled as external air is taken. Heating time ΔT3, the heating temperature and the cooling time may be set in advance in control unit 49, or may be input or changed by an operation of, for example, switch 110, by a signal from PC 300 connected to communication unit 150 through cable, or by a signal from a recording medium attached to communication unit 150.

After collection unit 12A is moved to collection chamber 5A at step S37, the heating operation and cooling operation are done in collection chamber 5A, and after cooling, collection unit 12A is moved to detection chamber 5B. Therefore, at the time of heating, heater 91 is positioned at a distance separated from the sensor equipment including light emitting element 6 and light receiving element 9 and also separated by wall 5C and, therefore, influence of heat of light emitting element 6 and light receiving element 9 can be prevented. Since heater 91 is in collection chamber 5A separated also by wall 5C and the like from the sensor equipment including light emitting element 6 and light receiving element 9 at the time of heating, heater 91 may not necessarily be positioned on the surface away from discharge electrode 17 of collection unit 12A, that is, the surface away from light emitting element 6 and light receiving element 9 when collection unit 12A moves to detection chamber 5B, but it may be on a surface close to discharge electrode 17.

When the heating operation at step S39 and the cooling operation at step S41 end, at step S43, control unit 49 outputs a control signal to driving unit 48 so that the mechanism for moving collection unit 12A is operated, and collection unit 12A is moved from collection chamber 5A to detection chamber 5B. After the movement ends, at step S45, the detecting operation is done again. The detecting operation at step S45 is the same as the detecting operation at step S35. A voltage value at this step in accordance with the fluorescence intensity F2 is input to detecting unit 40 and stored in storage unit 42. In this manner, an amount of fluorescence S2 after heating is measured.

After the amount of fluorescence S2 after heating is measured at step S45, a refreshing operation of collection unit 12A is done at step S47. At step S47, control unit 49 outputs a control signal to driving unit 48 to move the mechanism for moving brush 60, so that brush 60 reciprocates on the surface of collection unit 12A for a prescribed number of times. After the end of refreshing operation, at step S49, control unit 49 outputs a control signal to driving unit 48 to move the mechanism for moving collection unit 12A, and collection unit 12A is moved from detection chamber 5B to collection chamber 5A. Thus, the next collecting operation (S31) can be started immediately if a start instruction is received.

Calculating unit 41 calculates the difference between stored fluorescent intensities F1 and F2 as the amount of increase ΔF. As in detection apparatus 100B, the concentration of microorganisms, obtained using the calculated amount of increase ΔF and the correspondence relation (FIG. 23) between the amount of increase ΔF and the concentration of microorganisms (particle concentration) stored beforehand, is calculated as the concentration of microorganisms in the air introduced to collection chamber 5A in time period ΔT1. The calculated concentration of microorganisms among the collected particles is output from control unit 49 to display control unit 210.

As described above, in detection apparatus 100C, collection chamber 5A and detection chamber 5B are sectioned and collection unit 12A moves between the chambers for collection and detection. Therefore, it is possible to perform collection and detection continuously. Further, collecting jig 12 is heated in collection chamber 5A, cooled and thereafter moved to detection chamber 5B, as described above. Therefore, influence of heat on the sensors and the like in detection chamber 5B can be prevented.

Further, in detection apparatus 100C, when collection unit 12A moves from collection chamber 5A for the collecting step to detection chamber 5B for the detecting step, the cover provided on collection unit 12A closes hole 5C' of wall 5C. Therefore, entrance of external light to detection chamber 5B is blocked. Thus, stray light caused, for example, by scattering on airborne particles during fluorescence measurement can be reduced, and accuracy of measurement can be improved.

Though collection chamber 5A and detection chamber 5B provided as chambers partitioned by wall 5C are shown in FIG. 24, it is also possible to provide a collecting device and a detecting device as fully separated bodies, and to have collection unit 12A moved therebetween, or to have collection unit 12A set to each device, in detection apparatus 100C. In that case, heating of collecting jig 12 may be performed at a position outside the detecting device, separate from the sensor equipment including light emitting element 6 and light receiving element 9. By way of example, heating may be performed in the heating device corresponding to collection chamber 5A as described above, or at a position not in the collecting device or in the detecting device (for example, during movement from the collecting device to the detecting device). Heater 91 may be included in collection unit 12A or may be provided at a position to perform heating outside of the detecting device. Further, the collecting device and the detecting device may be used not as a set but each as a single device corresponding to collection chamber 5A or a single device corresponding to detection chamber 5B. In that case, the device used is adapted to include functions corresponding to signal processing unit 30, detecting unit 40 and the like.

Further, in FIG. 24, one collection unit 12A is provided, and by reciprocation indicated by the double-sided arrow A, the unit moves to and from collection chamber 5A and detection chamber 5B. As another example, two or more collection units 12A may be provided on a turntable and moved between collection chamber 5A and detection chamber 5B as the table turns. In such a configuration, it is possible to position one of the plurality of collection units in collection chamber 5A and positioning another in detection chamber 5B, thereby to perform the collecting operation and the detecting operation in parallel. Such a configuration enables continuous collecting operations and continuous detecting operations in parallel.

<Description of Display Control>

Display control unit 210 executes a process for displaying the results of detection received from detection apparatus 100 on display panel 130.

First Example of Display Control

Figure 27:
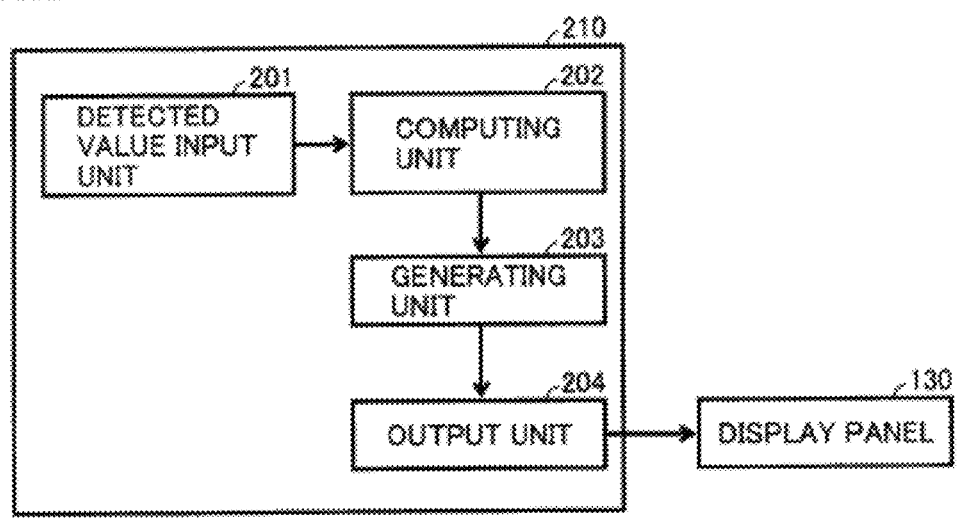
FIG. 27 is a block diagram showing a specific example of functional configuration of a display control unit in accordance with a first example.

FIG. 27 is a block diagram showing a specific example of functional configuration of display control unit 210 when display control unit 210 executes display control in accordance with the first example. The display control of the first example is for displaying pieces of information of different types related to environment in an easy-to-grasp manner. FIG. 27 shows an example in which the functions of display control unit 210 are mainly implemented by software configuration. It is noted, however, that at least part of these functions may be realized by hardware configuration such as electric circuits.

Referring to FIG. 27, display control unit 210 includes a detected value input unit 201 for receiving input of detection results from detection apparatus 100, a computing unit 202, a generating unit 203 and an output unit 204.

Computing unit 202 stores in advance "total value" of each of microorganisms and dust to be used for arithmetic operation, and carries out an operation for obtaining "relative value" for the input results of detection. Here, the "total value" represents a value as a preset reference for determining air pollution, and the "relative value" represents the ratio of the input result of detection to the "total value." In the following description, the "relative value" of microorganisms will also be referred to as "bacteria meter" and the "relative value" of dust will also be referred to as "dust meter." By way of example, assume that the number of particles is handled as the results of detection. Then, computing unit 202 stores the maximum values Nsmax and Ndmax of microorganisms and dust particles per prescribed volume (for example, the amount of air Vs introduced to case 5 per unit detection time described above). Then, by dividing the number Ns of microorganisms and the number Nd of dust particles per unit volume input as the results of detection by "total values Nsmax, Ndmax" as such, the ratio Ns/Nsmax of the number of microorganisms and the ratio Nd/Ndmax of the number of dust particles to the maximum value of particles per unit volume as "relative values" are obtained. Alternatively, assume that the concentration of particles is handled as the results of detection. Then, computing unit 202 stores the maximum values of the concentration of microorganisms and concentration of dust particles in the air, and by dividing the concentration of microorganisms and the concentration of dust particles input as the results of detection by respective "total values" as such, obtains the ratio of the concentration of microorganisms and ratio of the concentration of dust particles to the maximum values of concentration.

The "total value" of each of microorganisms and dust may be input through an operation of switch 110 or the like and stored in computing unit 202. Alternatively, such information may be read by communication unit 150 from storage medium recording the total values and thereby the information may be stored in computing unit 202. Such information may be received by communication unit 150 from a PC connected to a dedicated line, or other equipment communicating through the Internet or infrared communication, and stored in computing unit 202. Further, total values in accordance with prescribed conditions such as each environment (room) where air purifier 1 is installed, time of day, day of the week and so on may be stored, and the total values to be used may be selected by, for example, an operation of switch 110.

Generating unit 203 determines amounts of display necessary for unified display of calculated bacteria meter and dust meter, and generates display data based on the amounts of display. The "amount of display" is represented as the ratio of each relative value to the entire display area that represents the total amount. Simply, the amount of display is obtained by multiplying the value (angle, length, number of segments or the like) representing the entire display area by each calculated relative value. Specific method of display may include display of bacteria meter and dust meter in a circle graph, as described later. The manner of display is not limited to the circle graph, and other form such as a bar graph or a segment display may be possible. If the manner of display is a circle graph, the "amount of display" corresponds to the central angle, in a bar graph, the "amount of display" corresponds to the length, and in a segment display, the "amount of display" corresponds to the number of segments.

Output unit 204 performs a process for outputting the display data generated by generating unit 203. When the destination of output is display panel 130, output unit 204 realizes control for displaying on display panel 130 based on the generated display data.

As the results of detection, only the bacteria meter and dust meter may be displayed in unified manner. More preferably, the ratio of total sum of microorganism particles and dust particles in the air to the total sum of "total values" of microorganisms and dust is additionally displayed. In the following description, the "relative value" of the total sum of microorganism particles and dust particles will also be referred to as "pollution meter." The remaining ratio other than the pollution meter represents, in computation, the ratio of air not containing microorganism particles or dust particles. Therefore, this ratio may be referred to as "clean meter" opposite to the "pollution meter."

After the total sum of microorganism particles and dust particles (or the total sum of microorganism density and dust density) as the results of detection is divided by the total sum of "total value" of microorganisms and dust, respectively, based on the thus calculated ratio, the amount of display of the pollution meter may be determined by generating unit 203. Simply, the amount of display may be obtained as a sum of the amount of display of bacteria meter and the amount of display of dust meter determined by generating unit 203.

In the following description, it is assumed that in addition to the bacteria meter and the dust meter, the pollution meter and the clean meter are displayed. Further, the amount of display of pollution meter and the amount of display of clean meter are determined based on the sum of the amount of display of bacteria meter and the amount of display of dust meter.

Figure 28:
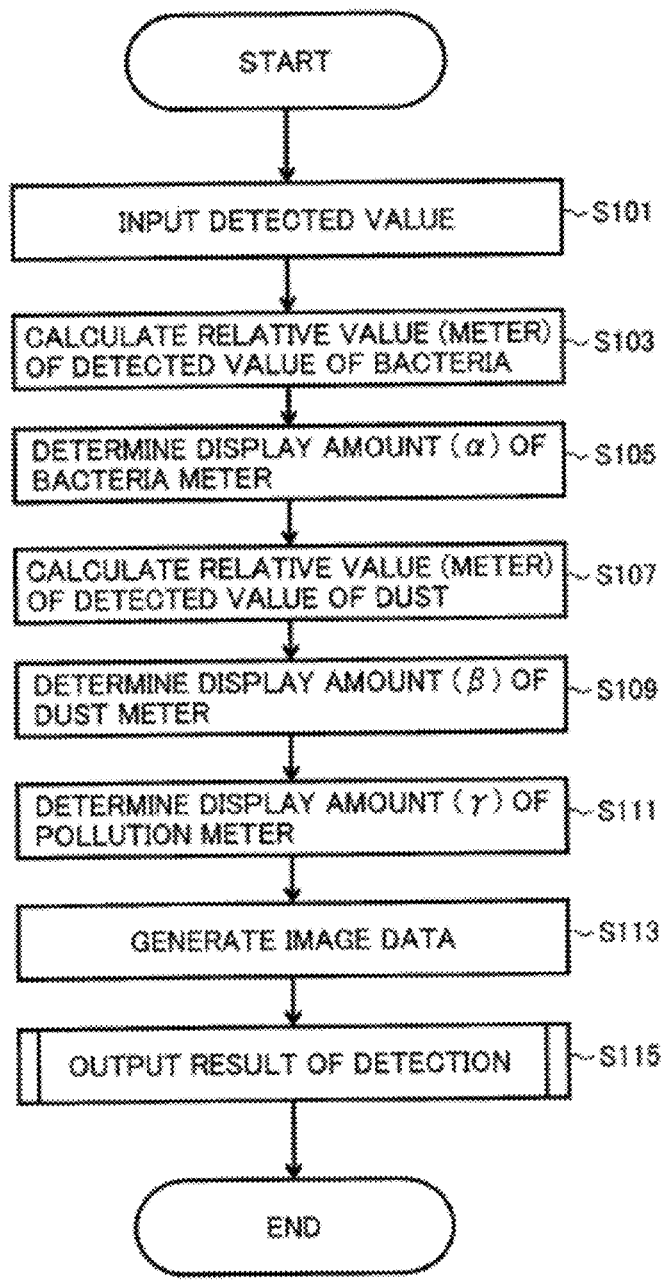
FIG. 28 is a flowchart showing a flow of control in the display control unit in accordance with the first example.
Figure 29:
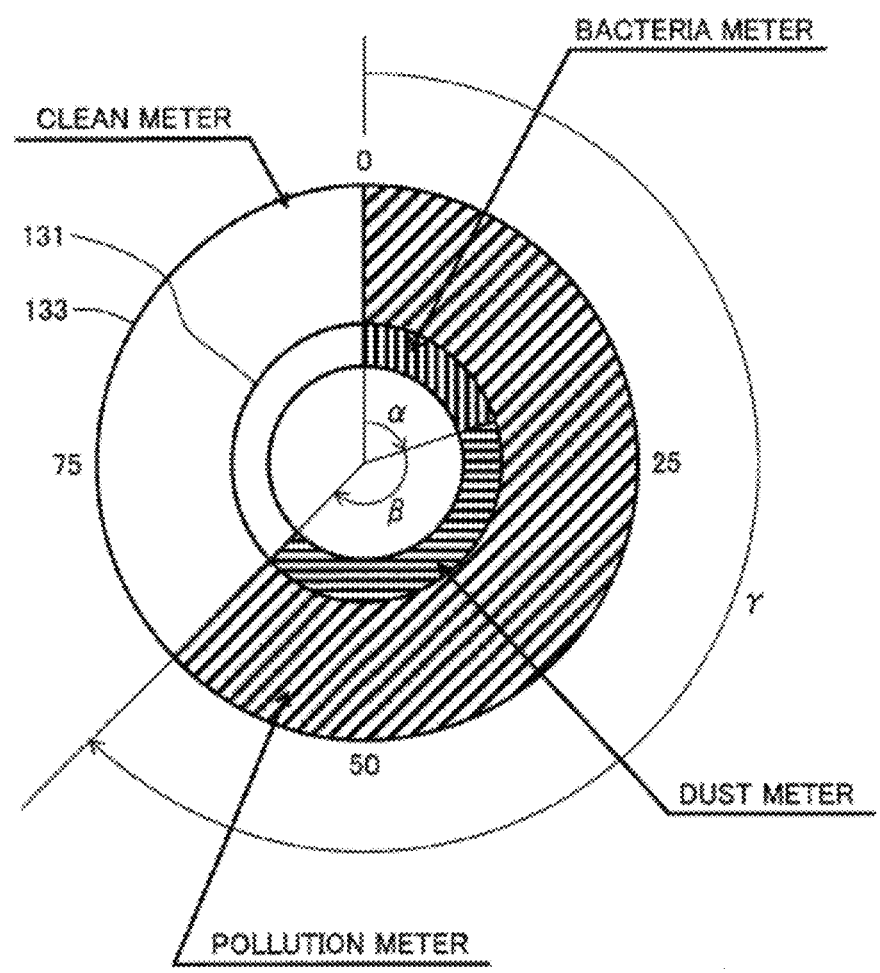
FIG. 29 shows a specific example of display.

Referring to FIG. 28, the flow of display control by display control unit 210 will be described, assuming that specific display shown in FIG. 29 is given. The process shown in the flowchart of FIG. 28 is realized by a CPU, not shown, included in control device 200 reading and executing programs stored in the memory to invoke various functions shown in FIG. 27.

Referring to FIG. 28, if input of detection result from detection apparatus 100 is received by detected value input unit 201 at S101, the relative value of microorganisms (bacteria meter) to the stored "total value" of microorganisms is calculated by computing unit 202 at S103, and the angle $\alpha$ of a circle graph as the "amount of display" for displaying the bacteria meter in a circle graph is determined by generating unit 203 at S105.

Similarly, the relative value of dust particles (dust meter) to the stored "total value" of dust is calculated by computing unit 202 at S107, and the angle $\beta$ of a circle graph as the "amount of display" for displaying the dust meter in a circle graph is determined by generating unit 203 at S109. The order of steps S103 to S109 is not limiting and the order may be changed.

At S111, generating unit 203 calculates the sum of angle $\alpha$ as the amount of display of bacteria meter determined at S105 and the angle $\beta$ as the amount of display of dust meter determined at S109, and thereby determines the angle $\gamma$ ($=\alpha+\beta$) of the circle graph as the "amount of display" for displaying the pollution meter in the circular graph.

At S113, based on these amounts of display, the display data is generated by generating unit 203. Specifically, the display data for realizing the display shown in FIG. 29 is generated. Specifically, referring to FIG. 29, the circle graph representing the results of detection includes areas 131 and 133. Area 131 is for displaying the bacteria meter and the dust meter. Area 133 is for displaying the pollution meter and the clean meter. Areas 131 and 133, in its entirety, each correspond to the total sum of "total value" of microorganisms and dust. The positional relation between areas 131 and 133 with respect to the center of the circle may be reversed.

Generating unit 203 realizes a manner of display (color, pattern) determined in advance for the bacteria meter in the area of angle α determined at S105 from the start point (in FIG. 29, the top position) of area 131, which is fixed in advance, as the area for the bacteria meter. Further, generating unit 203 realizes a manner of display determined in advance for the dust meter in the area of angle β determined at S109 from the start point that corresponds to the end point of bacteria meter of area 131. Further, generating unit 203 realizes a manner of display determined in advance for the pollution meter in the area of angle γ determined at S111 from the start point (in FIG. 29, the top position) of area 133 that is the same as start point of area 131.

In the example shown in FIG. 29, the bacteria meter and the dust meter are displayed in this order from the start point (top position) of area 131. The order, however, may be reversed. The order of pollution meter and the clean meter may also be reversed. Further, in the example shown in FIG. 29, the end point of bacteria meter is used as the start point for displaying the dust meter, that is, the bacteria meter and the dust meter are displayed successively without any gap between the bacteria meter and the dust meter. It is noted, however, that there may be some gap therebetween, or the display may be overlapped to some extent. The same applies to the pollution meter and the clean meter.

In the example of FIG. 29, each relative value is represented as percentage unit, and prescribed percentage values (0, 25, 50, 75) are displayed as indexes. The indexes may be displayed in smaller segments, or may not be displayed at all. The indexes may be displayed with scale markings. Further, specific value of each relative value may be displayed in addition to the display shown in FIG. 29. Captions "BACTERIA METER" and "DUST METER" on FIG. 29 may be additionally displayed.

When the display data as such are generated at S113, a process for output is executed by output unit 204 at S115. If the output destination is display panel 130, the display of FIG. 29 is given on display panel 130 by the process at S115.

As the process described above is executed by display control unit 210 and the display of FIG. 29 is given on display panel 130, the user can grasp in a unified manner the results of detection of microorganisms and dust particles by detection apparatus 100. Specifically, in the area 131 of circular graph, the bacteria meter is displayed in the area from the start point of area 131 fixed in advance to the angle α corresponding to the relative value, and the dust meter is displayed in the area from the end point of bacteria meter as the start point to the angle β corresponding to the relative value. Therefore, the user can grasp immediately and in a sensual manner the ratio of microorganisms and the ratio of dust particles in the air as a whole. Further, the user can grasp immediately and in a sensual manner the ratio of the sum of microorganisms and the dust particles to the air as a whole. The ratio can be grasped more aptly as it is displayed as "pollution meter" in area 133 of the circular graph. The amount of microorganisms in the air serves as helpful information to determine the risk of catching a cold or risk of mold development, both of which are much related to microorganisms. Therefore, such display helps the user to determine the risk of catching a cold or risk of mold development.

The above-described process is repeated at a prescribed interval in display control unit 210. Accordingly, the real-time results of detection of microorganisms and dust particles by detection apparatus 100 can be reflected on the display. If the circular graph shown in FIG. 29 is displayed continuously, display control unit 210 updates the display on display panel 130 every time the process described above is executed. As a result, the areas of bacteria meter and dust meter change, and the boundary between the pollution meter and clean meter moves accordingly.

Figure 30:
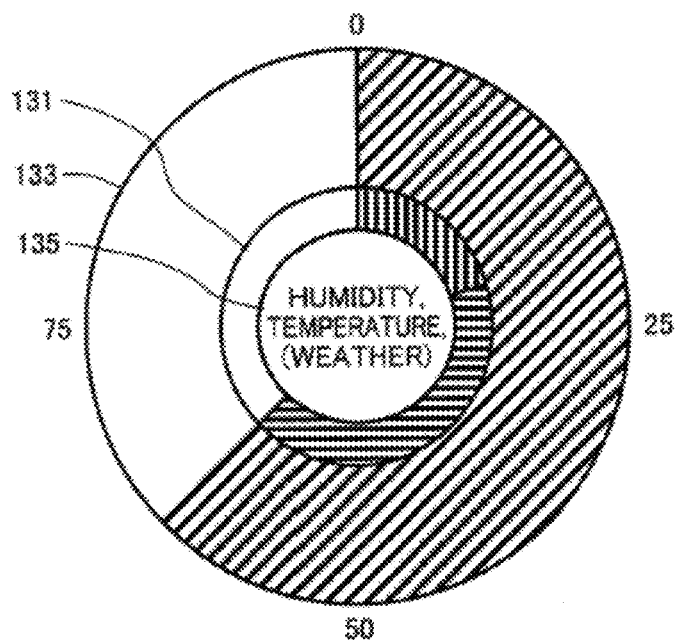
FIG. 30 shows another specific example of display.

In the example of FIG. 29, pieces of information based on the microorganisms and dust particles detected by detection apparatus 100 are displayed as information related to the environment. Display control unit 210 may additionally display other pieces of information. By way of example, if it is possible to obtain pieces of information related to humidity, temperature, weather or season through communication with other equipment by communication unit 150, such pieces of information may be displayed on an area 135 in the circular graph, as shown in FIG. 30. The display is not limited to text display such as shown in FIG. 30, and it may include an illustration, an animation, a specific color or pattern. Such display enables unified presentation of more information related to the environment. Thus, in addition to the ratio of microorganisms and the ratio of dust particles in the air as a whole, the user can grasp immediately more information related to the environment.

Figure 31:
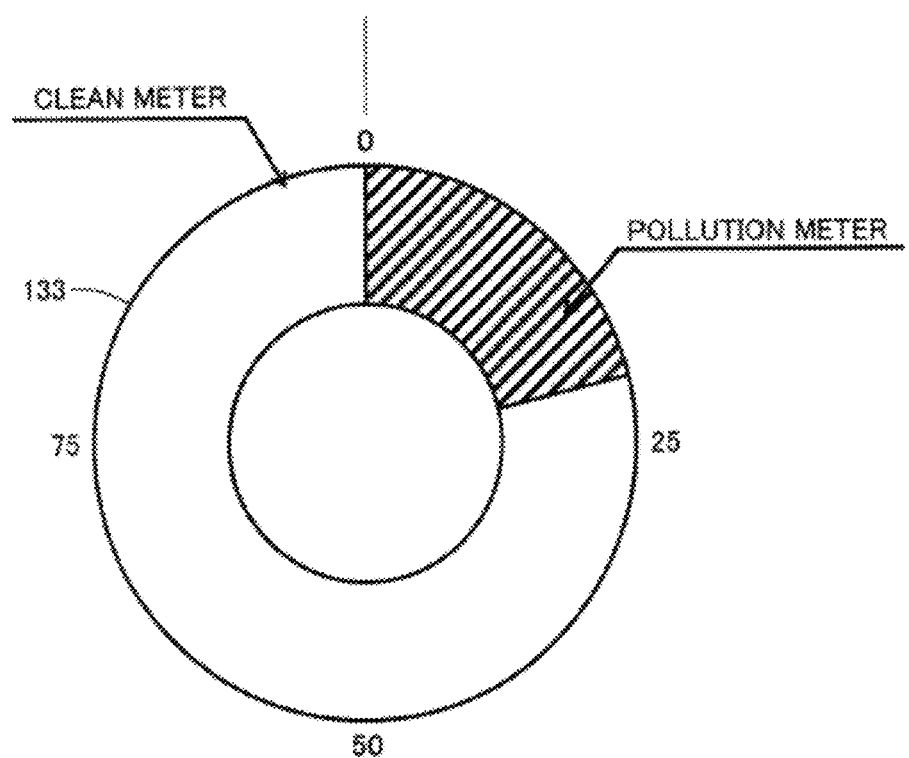
FIG. 31 shows a still another specific example of display.

In the example above, both the microorganisms and dust particles are detected by detection apparatus 100. It is sufficient if at least microorganisms are detected and the display related to the microorganisms is given as a result. Specifically, in this case, microorganisms are regarded as the cause of air pollution, and the result of detection may be represented only by the bacteria meter (=pollution meter) as shown in FIG. 31. By such an approach also, it is possible for the user to immediately grasp the ratio of microorganisms with respect to the index ("total value" for the microorganisms) for determining air pollution.

Second Example of Display Control

Figure 32:
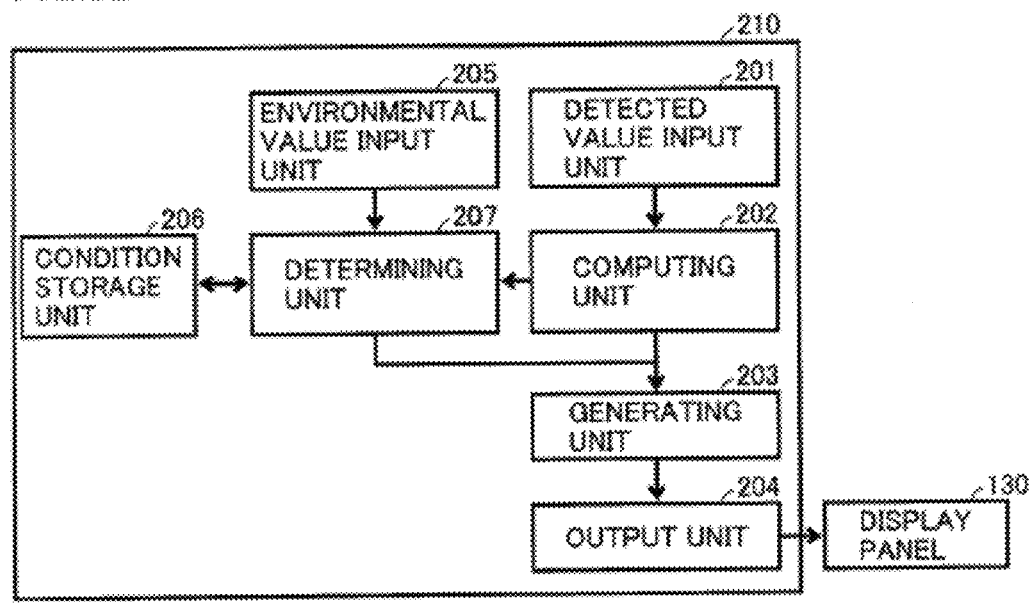
FIG. 32 is a block diagram showing a specific example of functional configuration of a display control unit in accordance with a second example.

FIG. 32 is a block diagram showing a specific example of functional configuration of display control unit 210 when display control unit 210 executes display control in accordance with the second example. The display control in accordance with the second example is for displaying messages related to the environment. FIG. 32 shows an example in which the functions of display control unit 210 are mainly implemented by software configuration. It is noted, however, that at least part of these functions may be realized by hardware configuration such as electric circuits.

Referring to FIG. 32, display control unit 210 includes detected value input unit 201 for receiving input of detection results from detection apparatus 100, computing unit 202, generating unit 203, output unit 204, an environmental value input unit 205 for receiving an environmental value received by communication unit 150 from other equipment, a condition storage unit 206 for storing conditions used for displaying messages and correspondence relations between the conditions and the messages as will be described later, and a determining unit 207 for determining and deciding the message to be displayed.

Here, the "message" refers to a message related to the environmental status, including information for presenting information related to mold development and information related to health such as a cold. Though it is assumed that the message is given as a character sequence in the following, the message may be given by an icon, an animation or voice.

Messages to be displayed in accordance with various conditions are stored in advance in condition storage unit 206. The messages may be input by an operation of switch 110 or the like and stored in condition storage unit 206 by the operation of display control unit 210. Alternatively, communication unit 150 may read such information from a recording medium recording the messages, and the information may be stored in condition storage unit 206 by the operation of display control unit 210. Further, communication unit 150 may receive such information from other equipment using, for example, a PC connected to a dedicated line, through the Internet or infrared communication and the information may be stored in condition storage unit 206 by the operation of display control unit 210. Further, the messages and the correspondence to the conditions stored in condition storage unit 206 may be updated by display control unit 210.

Computing unit 202 is the same as computing unit 202 described in connection with the first example of display control, and it calculates the "relative values" of detection results with respect to the stored "total values." Generating unit 203 is also the same as generating unit 203 described in connection with the first example of display control, and it determines amounts of display necessary for displaying the calculated bacteria meter and dust meter in unified manner, and generates the display data of bacteria meter and dust meter based on the amounts of display.

By way of example, environmental value input unit 205 receives a value representing temperature (room temperature) from a thermometer placed in a room, a value representing humidity from a hygrometer placed in the room, and pieces of information representing weather and season (for example, specific period of year such as rainy season) obtained through the Internet communication or data communication of terrestrial digital broadcast, from communication unit 150.

Condition storage unit 206 stores conditions to be used for displaying messages, constituted by combinations of the environmental values and the pieces of information obtained from the detected values. Further, specific messages corresponding to conditions are stored. Determining unit 207 refers to the stored conditions, specifies the condition from the above-described relative values from the input detected values and the environmental values, and determines a message that corresponds to the specified condition as the message to be displayed. In the embodiment, it is assumed that conditions defined by combinations of the calculated relative values and the environmental values are stored. The conditions defined by the combinations of detected values and environmental values may be stored.

Generating unit 203 generates display data for displaying the determined message, in addition to the display of detection results (the bacteria meter and the dust meter). It is assumed that the display data for displaying the messages are stored message by message in advance. Based on the display of detection results, generating unit 203 determines the position for displaying the message, and embeds the display data for displaying the determined message on the determined position and thereby generates the display data for screen image display.

Output unit 204 executes a process for outputting the display data generated by generating unit 203. When the destination of output is display panel 130, output unit 204 realizes control for displaying on display panel 130 based on the generated display data.

The result of detection is displayed in the similar manner as that described in connection with the first example of display control. Specifically, the pollution meter and the clean meter are displayed in addition to the bacteria meter and the dust meter.

Figure 33:
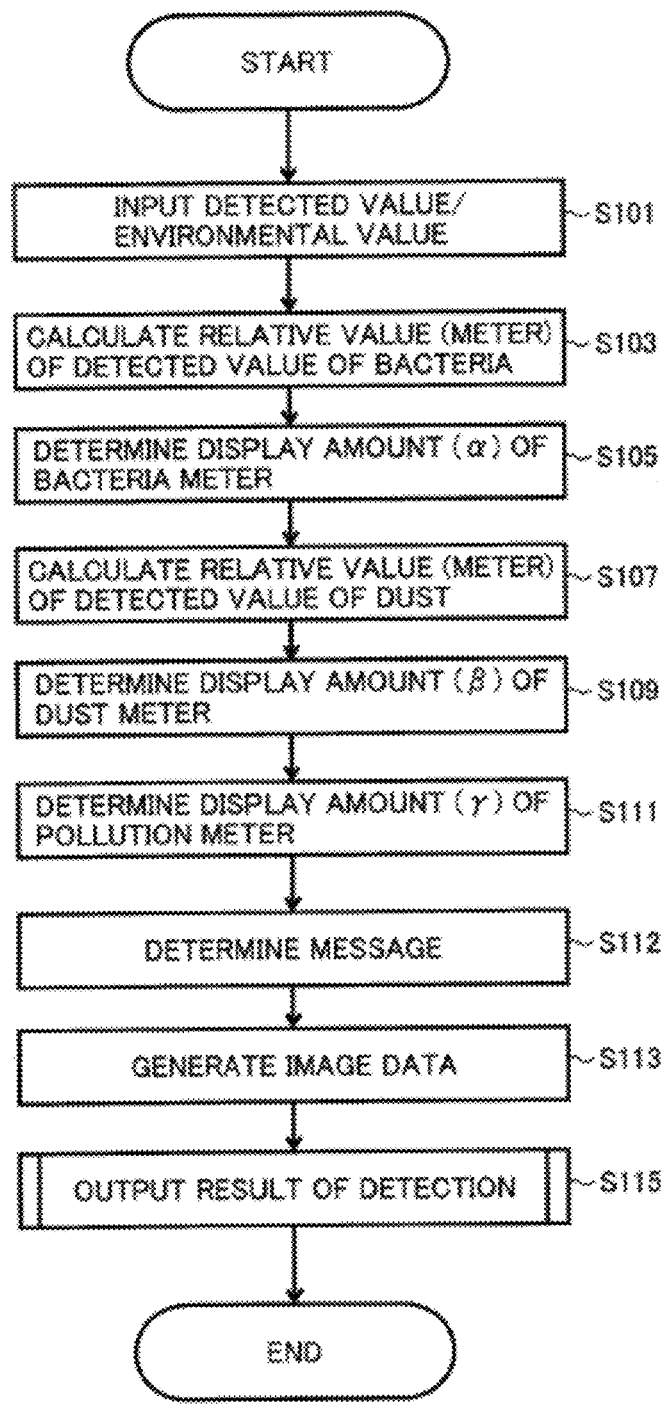
FIG. 33 is a flowchart showing a specific example of control flow in the display control unit in accordance with the second example.

FIG. 33 is a flowchart representing the flow of display control in accordance with the second example. The flow of display control by display control unit 210 will be described, using FIG. 36A as a specific example of display. The process shown in the flowchart of FIG. 33 is realized by a CPU, not shown, included in control device 200 reading and executing programs stored in the memory to invoke various functions shown in FIG. 32.

Referring to FIG. 33, in the second example of display control, after the process of S111 of the flow of display control of the first example shown in FIG. 28, the process of S112 is additionally executed. Here, the process of S112, which is different from the flow of display control of the first example, will be described.

Figures 36A, 36B, 36C:
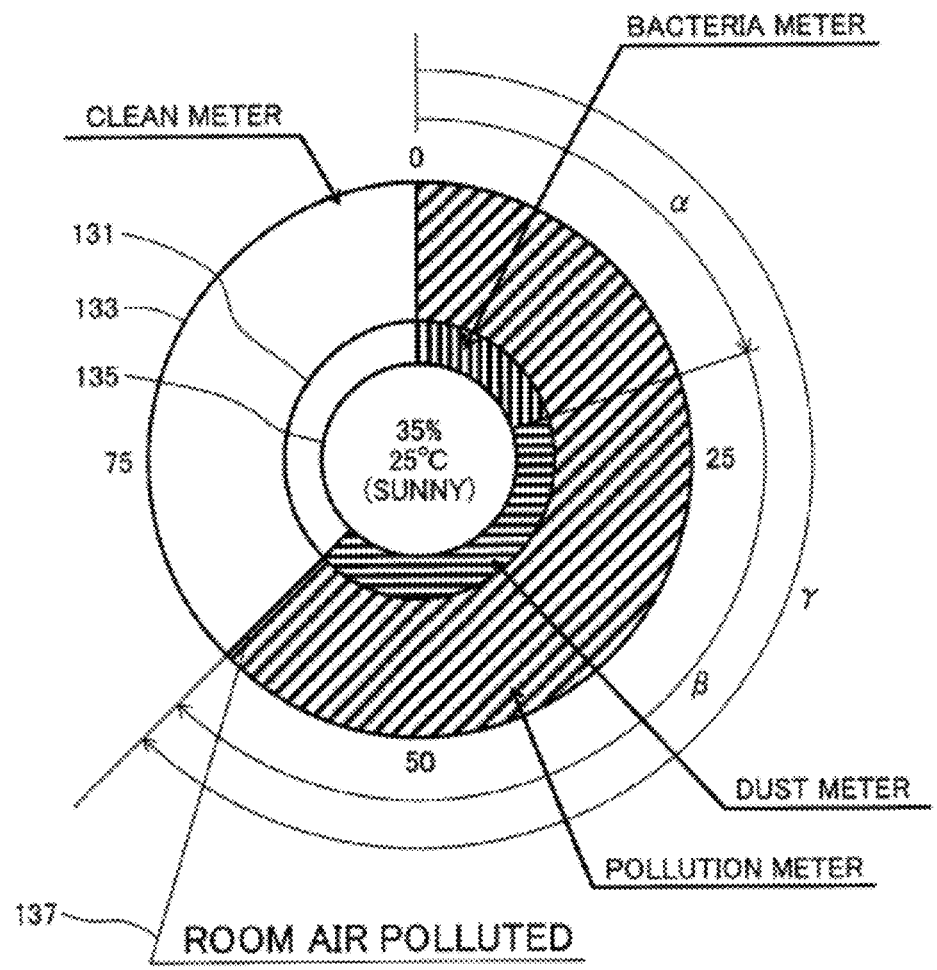
FIG. 36A shows a specific example of display.
FIG. 36B shows a specific example of displayed messages.
FIG. 36C shows a specific example of a displayed message.

At S112, determining unit 207 refers to the conditions and the correspondence relation with the messages stored in condition storage unit 206, and the message to be displayed is determined. At S113, in generating unit 203, display data is generated based on the amount of display determined at S109 and S111 and the message determined at S112. Specifically, display data for realizing the display of FIG. 36A is generated. Referring to FIG. 36A, the circular graph representing the results of detection is similar to the circular graph displayed in the first example of display control. In the second example of display control, areas 135 and 137 are additionally provided. Area 135 is for displaying the environmental value. Area 137 is for displaying the message.

In the second example of display control, generating unit 203 determines the boundary position between the pollution meter and the clean meter, that is, a position close to the position of angle γ from the display start position of bacteria meter, to be the area 137 for displaying the message. In order to display the message determined at S112, display data stored beforehand is embedded in this area. Further, in area 135, display data for displaying the environmental values received at S101 such as the temperature, humidity and weather is embedded. The display of environmental values are not limited to text display such as shown in FIG. 36A, and the display may include an illustration, an animation, a specific color or a pattern.

When such data is generated at S113, the process for outputting to output unit 204 is executed at S115. If the output destination is display panel 130, the display of FIG. 36A is displayed on display panel 130 by the process of S115.

As the process described above is executed by display control unit 210 and the display of 36A is given on display panel 130, the user can grasp the results of detection of microorganisms and dust particles by detection apparatus 100 in a unified manner. Specifically, in the area 131 of circular graph, the bacteria meter is displayed in the area from the start point of area 131 fixed in advance to the angle α corresponding to the relative value, and the dust meter is displayed in the area from the end point of bacteria meter as the start point to the angle β corresponding to the relative value. Therefore, the user can grasp immediately and in a sensual manner the ratio of microorganisms and the ratio of dust particles in the air as a whole. Further, the user can grasp immediately and in a sensual manner the ratio of the sum of microorganisms and the dust particles to the air as a whole. The ratio can be grasped more aptly as it is displayed as "pollution meter" in area 133 of the circular graph. In addition, the environmental status including risk of catching a cold or risk of mold development can easily be grasped by the displayed messages.

The above-described process is repeated at a prescribed interval in display control unit 210. Accordingly, the real-time results of detection of microorganisms and dust particles by detection apparatus 100 can be reflected on the display. If the circular graph representing the results of detection is displayed continuously, display control unit 210 updates the display on display panel 130 every time the process described above is executed. As a result, the areas of bacteria meter and dust meter change, and the boundary between the pollution meter and clean meter moves accordingly. Further, the displayed message changes.

Figure 34:
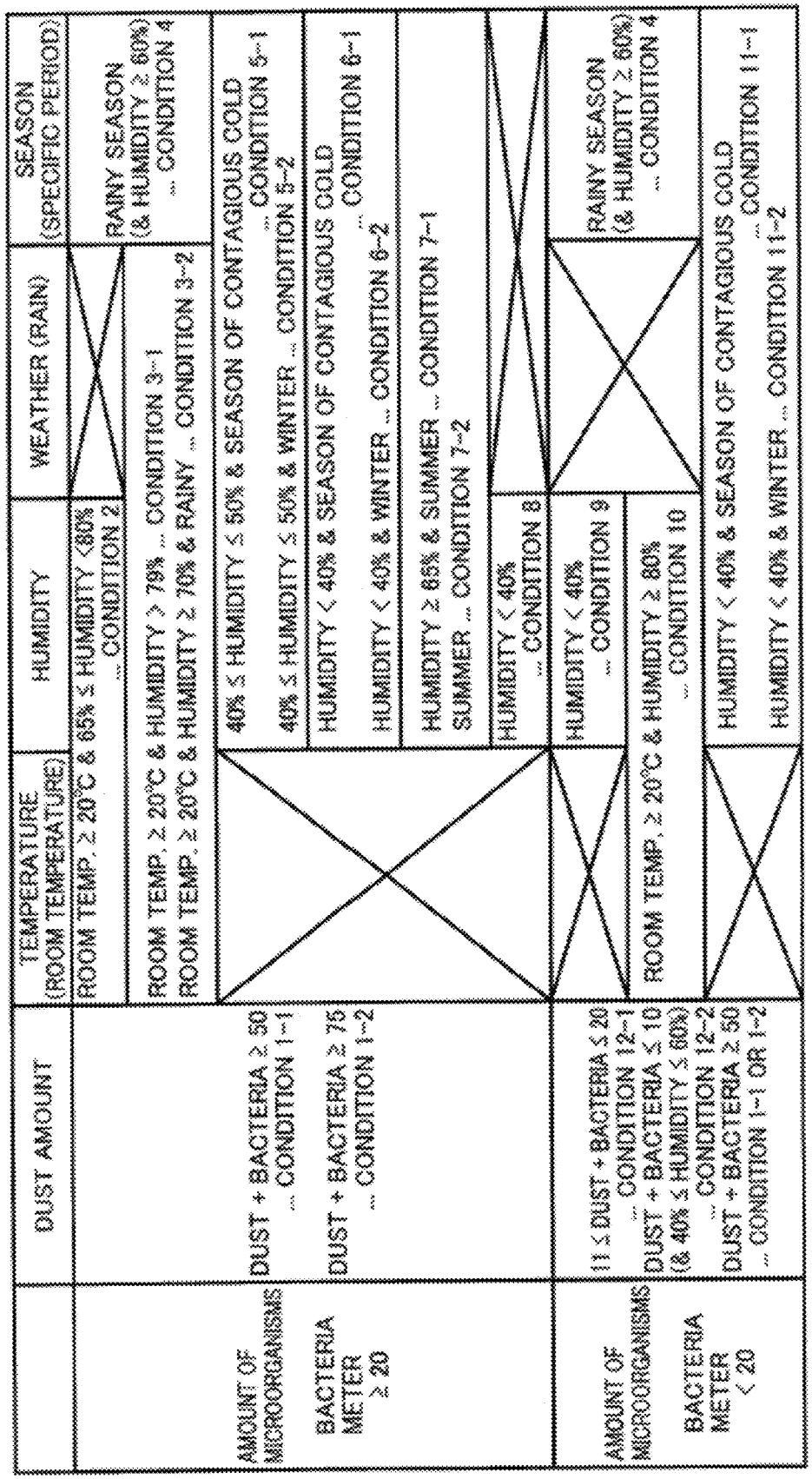
FIG. 34 shows specific examples of conditions for determining messages.

In the following, displays given when conditions of FIG. 34 are stored in condition storage unit 206 and correspondence between messages shown in FIG. 35 and respective conditions is established will be described, with reference to specific examples of display. As the environmental values are used generally as described in the following, the environmental status can be determined with high accuracy, and appropriate message can be displayed. By the message, the user can grasp the environmental status, and can take necessary measures. Specific numerical values of conditional equations in FIG. 34 are examples only, and not limiting.

From the conditions shown in FIG. 34, if the bacteria meter calculated at S103 is 20(%) or higher and the sum of dust meter and bacteria meter, that is, the pollution meter is 50 or higher, determining unit 207 determines that the condition for determining a message is condition 1-1 at S112, and from the correspondence relation shown in FIG. 35, determines the message "ROOM AIR POLLUTED" corresponding to condition 1-1 to be the message to be displayed.

When the condition is 1-1, generating unit 203 generates data for displaying the results of detection in areas 131 and 133 and for displaying the determined message "ROOM AIR POLLUTED" in area 137 near the boundary between the pollution meter and the clean meter as shown in FIG. 36A. At S115, output unit 204 outputs the display data as such to display panel 130 and by such display control, the image of FIG. 36A is displayed on display panel 130.

FIG. 35 shows an example in which only the message "ROOM AIR POLLUTED" is shown as corresponding to condition 1-1. However, a plurality of messages may be prepared to correspond to condition 1-1, as in the case of condition 7-1. By way of example, assume that a plurality of messages including "ROOM AIR POLLUTED," "WATCH OUT FOR ALLERGIES" and "RUN AIR PURIFIER" are stored. In that case, the plurality of messages may be displayed side by side as shown in FIG. 36B or may be displayed one by one (in rotation) at a prescribed time interval (of, for example, few seconds), on the area for displaying messages on the screen image.

If the bacteria meter calculated at S103 is 20(%) or higher and the pollution meter is 75 or higher, determining unit 207 determines that the condition for determining a message is both conditions 1-1 and 1-2 at S112. In determining unit 207, preferably, priority is set for preset conditions (or at least for conditions that may overlap). Therefore, in this situation, that is, when a plurality of conditions are specified by the environmental values, considering the priority, a condition having high priority is determined to be the condition for determining the message. Preferably, the priority is higher if the condition can be an environmental factor of higher risk. When we compare conditions 1-1 and 1-2, the condition corresponding to the higher value of pollution meter has higher priority. In accordance with the priority, determining unit 207 determines condition 1-2 to be the condition for determining the message. Further, from the correspondence relation shown in FIG. 35, the message "PURIFY AIR IMMEDIATELY" corresponding to condition 1-2 is determined to be the message to be displayed.

If such a determination is made and the image of FIG. 36A has already been displayed on display panel 130 as the previous image at the timing of screen display, the display is continuously switched to the next results of detection and the next message by the process described above by display control unit 210. Specifically, the areas of bacteria meter and dust meter change in accordance with the results of detection and the position of boundary between the pollution meter and the clean meter changes accordingly. Further, the message "ROOM AIR POLLUTED" of FIG. 36A is switched to the message "PURIFY AIR IMMEDIATELY."

From the conditions shown in FIG. 34, if the bacteria meter calculated at S103 is 20(%) or higher, humidity is at least 65% and lower than 80% and the room temperature is 20° C. or higher, determining unit 207 determines that the condition for determining a message is condition 2 at S112, and from the correspondence relation shown in FIG. 35, determines the message "MOLD DEVELOPMENT PROBABLE" corresponding to condition 2 to be the message to be displayed.

Figures 37A, 37B:
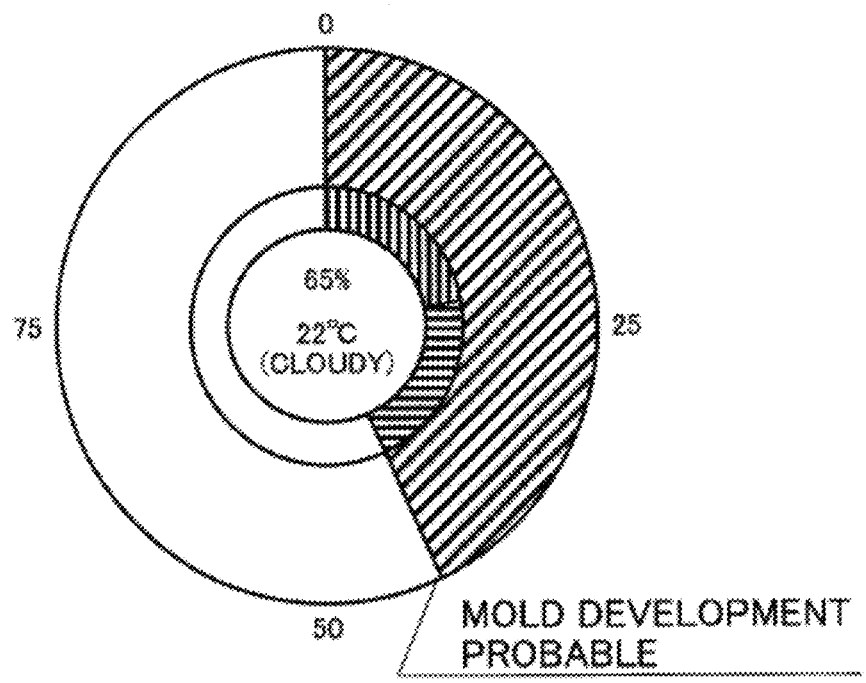
FIG. 37A shows a specific example of display.
FIG. 37B shows a specific example of displayed messages.

If the condition is 2, at S113, generating unit 203 generates display data for displaying the determined message "MOLD DEVELOPMENT PROBABLE" near the boundary between the pollution meter and the clean meter displayed as results of detection. At S115, output unit 204 outputs the display data as such to display panel 130 and by such display control, the image of FIG. 37A is displayed on display panel 130.

FIG. 35 shows an example in which only the message "MOLD DEVELOPMENT PROBABLE" is shown as corresponding to condition 2. However, a plurality of messages may be prepared to correspond to condition 2. By way of example, assume that a plurality of messages including "MOLD DEVELOPMENT PROBABLE" and "DEHUMIDIFY/REMOVE BACTERIA" are stored. In that case, the plurality of messages may be displayed side by side as shown in FIG. 37B or may be displayed one by one (in rotation) at a prescribed time interval, on the area for displaying messages on the screen image.

From the conditions shown in FIG. 34, if the bacteria meter calculated at S103 is 20(%) or higher, humidity is higher than 79% and the room temperature is 20° C. or higher, determining unit 207 determines that the condition for determining a message is condition 3-1 at S112, and from the correspondence relation shown in FIG. 35, determines the message "RISK OF MOLD DEVELOPMENT ELEVATED" corresponding to condition 3-1 to be the message to be displayed.

Similarly, if the bacteria meter calculated at S103 is 20(%) or higher, humidity is higher than 70%, the room temperature is 20° C. or higher and the weather is rainy, determining unit 207 determines that the condition for determining a message is condition 3-2 at S112, and from the correspondence relation shown in FIG. 35, determines the message "RISK OF MOLD DEVELOPMENT ELEVATED" corresponding to condition 3-2 to be the message to be displayed.

Figures 38A, 38B:
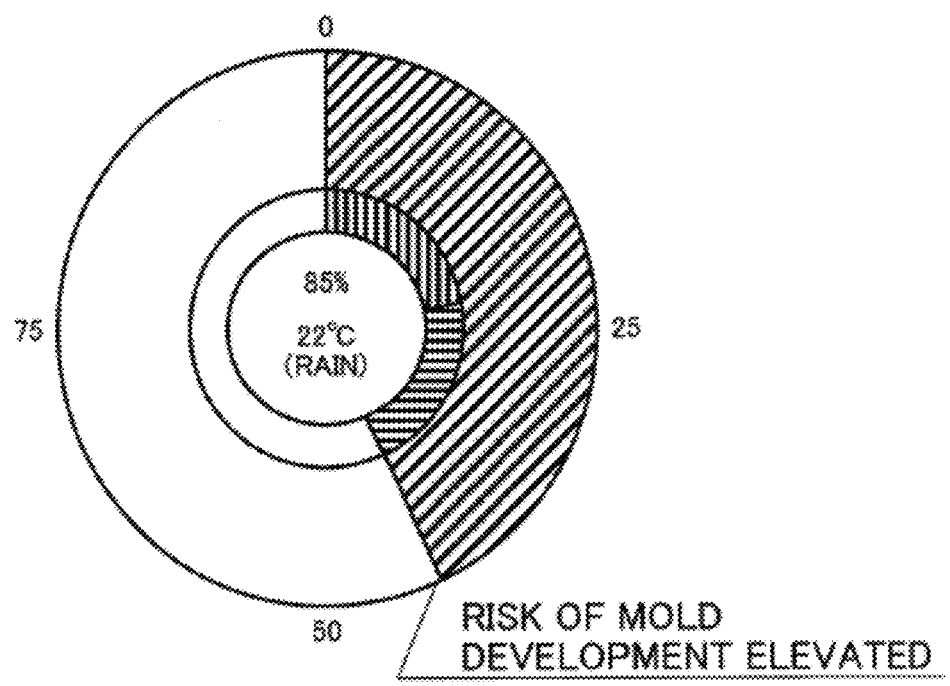
FIG. 38A shows a specific example of display.
FIG. 38B shows a specific example of displayed messages.

If the condition is 3-1 or 3-2, at S113, generating unit 203 generates display data for displaying the determined message "RISK OF MOLD DEVELOPMENT ELEVATED" near the boundary between the pollution meter and the clean meter displayed as results of detection as shown in FIG. 38A. At S115, output unit 204 outputs the display data as such to display panel 130 and by such display control, the image of FIG. 38A is displayed on display panel 130.

FIG. 35 shows an example in which only the message "RISK OF MOLD DEVELOPMENT ELEVATED" is shown as corresponding to conditions 3-1 and 3-2. However, a plurality of messages may be prepared to correspond to conditions 3-1 and 3-2. By way of example, assume that a plurality of messages including "RISK OF MOLD DEVELOPMENT ELEVATED" and "DEHUMIDIFY/REMOVE BACTERIA" are stored. In that case, the plurality of messages may be displayed side by side as shown in FIG. 38B or may be displayed one by one (in rotation) at a prescribed time interval, on the area for displaying messages on the screen image.

From the conditions shown in FIG. 34, if humidity is 60% or higher and the season information is identified to be rainy season based, for example, on information of rain front obtained through the Internet, determining unit 207 determines that the condition for determining a message is condition 4 at S112 regardless of the value of bacteria meter or the weather, and from the correspondence relation shown in FIG. 35, determines the message "RISK OF MOLD DEVELOPMENT ELEVATED" corresponding to condition 4 to be the message to be displayed.

Figures 39A, 39B:
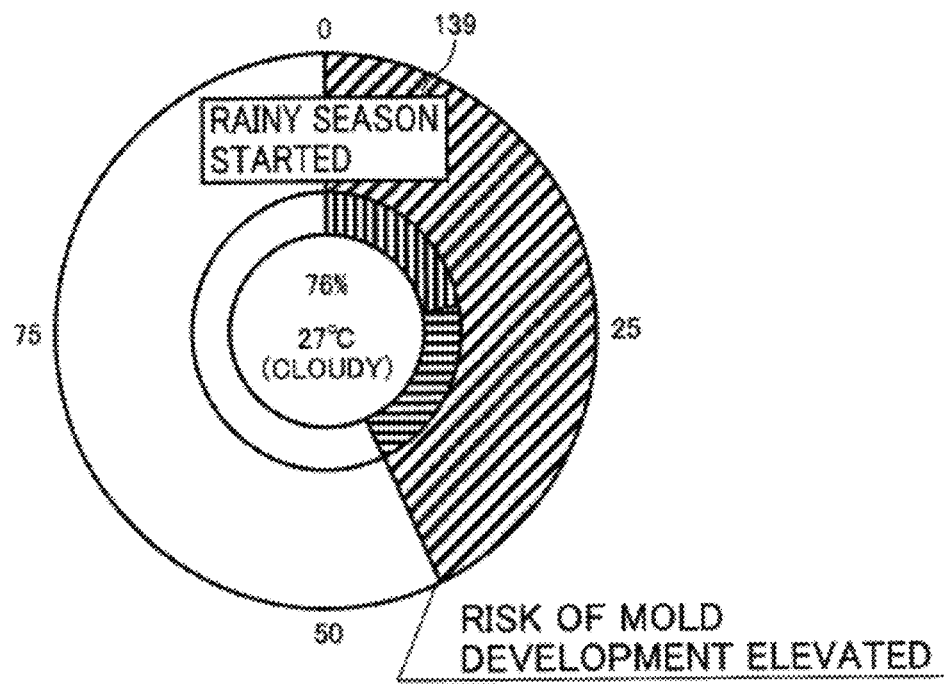
FIG. 39A shows a specific example of display.
FIG. 39B shows a specific example of displayed messages.

If the condition is 4, at S113, generating unit 203 generates display data for displaying the determined message "RISK OF MOLD DEVELOPMENT ELEVATED" near the boundary between the pollution meter and the clean meter displayed as results of detection as shown in FIG. 39A. At S115, output unit 204 outputs the display data as such to display panel 130 and by such display control, the image of FIG. 39A is displayed on display panel 130. Further, preferably, if the condition is 4, generating unit 203 generates display data for displaying a message "RAINY SEASON STARTED" indicating the rainy season in an area 139, for example, near the detection results. Display data for such a message is also stored in advance in generating unit 203 and, when condition 4 is determined, it is determined that such a message should be displayed together with the message from FIG. 35.

FIG. 35 shows an example in which only the message "RISK OF MOLD DEVELOPMENT ELEVATED" is shown as corresponding to condition 4. However, a plurality of messages may be prepared to correspond to condition 4. By way of example, assume that a plurality of messages including "RISK OF MOLD DEVELOPMENT ELEVATED" and "DEHUMIDIFY/REMOVE BACTERIA" are stored. In that case, the plurality of messages may be displayed side by side as shown in FIG. 39B or may be displayed one by one (in rotation) at a prescribed time interval, on the area for displaying messages on the screen image.

From the conditions shown in FIG. 34, if the bacteria meter calculated at S103 is 20(%) or higher, humidity is 40% to 50% and the season information is identified to be the season of cold infection based, for example, on information of cold spreading obtained through the Internet, determining unit 207 determines that the condition for determining a message is condition 5-1 at S112, and from the correspondence relation shown in FIG. 35, determines the message "WATCH OUT FOR CONTAGIOUS COLD" corresponding to condition 5-1 to be the message to be displayed.

If the bacteria meter calculated at S103 is 20(%) or higher, humidity is 40% to 50% and the season information is identified to be the winter season as determined beforehand by month, for example, determining unit 207 determines that the condition for determining a message is condition 5-2 at S112, and from the correspondence relation shown in FIG. 35, determines the message "WATCH OUT FOR FLU" corresponding to condition 5-2 to be the message to be displayed.

Figures 40A, 40B:
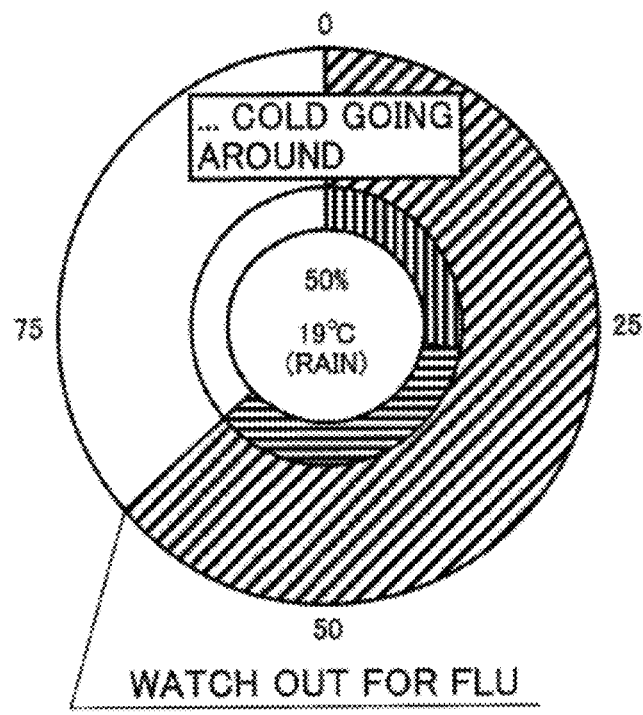
FIG. 40A shows a specific example of display.
FIG. 40B shows a specific example of displayed messages.

If the condition is 5-2, at S113, generating unit 203 generates display data for displaying the determined message "WATCH OUT FOR FLU" near the boundary between the pollution meter and the clean meter displayed as results of detection as shown in FIG. 40A. At S115, output unit 204 outputs the display data as such to display panel 130 and by such display control, the image of FIG. 40A is displayed on display panel 130. Similarly, if the condition is 5-1, display data for displaying the message "WATCH OUT FOR CONTAGIOUS COLD" near the boundary between the pollution meter and the clean meter is generated. Further, preferably, if the determined condition is 5-1 or 5-2, generating unit 203 also generates display data for additionally displaying the message " . . . COLD GOING AROUND" indicating that it is a cold season. Display data for such a message is also stored in advance in generating unit 203 and, when condition 5-1 or 5-2 is determined, it is determined that such a message should be displayed together with the message from FIG. 35.

FIG. 35 shows an example in which only the message "WATCH OUT FOR FLU" is shown as corresponding to condition 5-1. However, a plurality of messages may be prepared to correspond to condition 5-1. By way of example, assume that a plurality of messages including "WATCH OUT FOR FLU" and "WASH YOUR HANDS AND GARGLE" are stored. In that case, the plurality of messages may be displayed side by side as shown in FIG. 40B or may be displayed one by one (in rotation) at a prescribed time interval, on the area for displaying messages on the screen image.

From the conditions shown in FIG. 34, if the bacteria meter calculated at S103 is 20(%) or higher, humidity is 40% or higher and the season information is identified to be the season of cold infection based, for example, on information of cold spreading obtained through the Internet, determining unit 207 determines that the condition for determining a message is condition 6-1 at S112, and from the correspondence relation shown in FIG. 35, determines the message "WATCH OUT FOR . . . COLD" corresponding to condition 6-1 to be the message to be displayed.

If the bacteria meter calculated at S103 is 20(%) or higher, humidity is lower than 40% and the season information is identified to be the winter season, determining unit 207 determines that the condition for determining a message is condition 6-2 at S112, and from the correspondence relation shown in FIG. 35, determines the message "FLU ALARM" corresponding to condition 6-2 to be the message to be displayed.

Figures 41A, 41B:
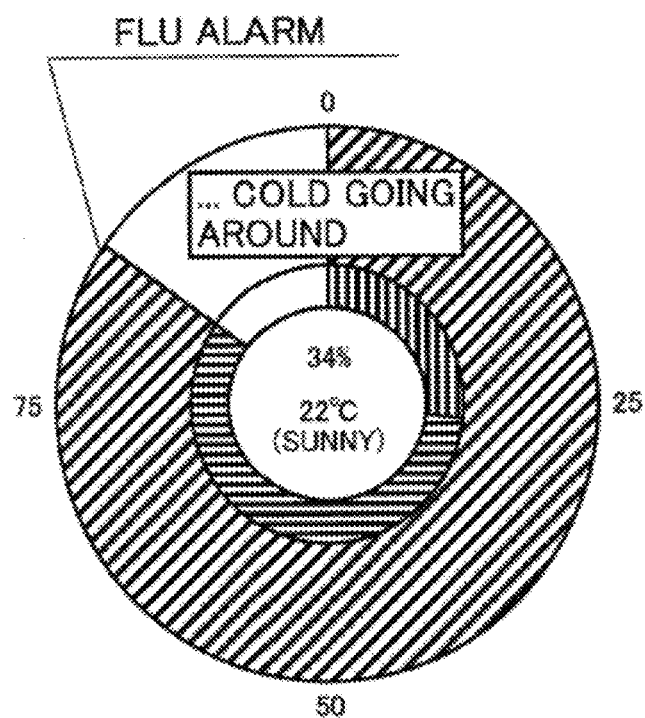
FIG. 41A shows a specific example of display.
FIG. 41B shows a specific example of displayed messages.

If the condition is 6-2, at S113, generating unit 203 generates display data for displaying the determined message "FLU ALARM" near the boundary between the pollution meter and the clean meter displayed as results of detection as shown in FIG. 41A. At S115, output unit 204 outputs the display data as such to display panel 130 and by such display control, the image of FIG. 41A is displayed on display panel 130. Similarly, if the condition is 6-1, display data for displaying the message "WATCH OUT FOR . . . COLD" near the boundary between the pollution meter and the clean meter is generated. More preferably, if the condition is 6-1 or 6-2, generating unit 203 also generates display data for additionally displaying the message " . . . COLD GOING AROUND" indicating that it is a cold season. Display data for such a message is also stored in advance in generating unit 203 and, when condition 6-1 or 6-2 is determined, it is determined that such a message should be displayed together with the message from FIG. 35.

FIG. 35 shows an example in which only the message "FLU ALARM" is shown as corresponding to condition 6-2. However, a plurality of messages may be prepared to correspond to condition 6-2. By way of example, assume that a plurality of messages including "FLU ALARM," "IMMEDIATELY HUMIDIFY/REMOVE BACTERIA" and "TAR- GET HUMIDITY 55-65%" are stored. In that case, the plurality of messages may be displayed side by side as shown in FIG. 41B or may be displayed one by one (in rotation) at a prescribed time interval, on the area for displaying messages on the screen image.

From the conditions shown in FIG. 34, if the bacteria meter calculated at S103 is 20(%) or higher, humidity is 65% or higher and the season information is identified to be the summer season, determining unit 207 determines that the condition for determining a message is condition 7-1 at S112, and from the correspondence relation shown in FIG. 35, determines the messages "MOLD DEVELOPMENT PROBABLE" and "WATCH OUT FOR SUMMER COLD" corresponding to condition 7-1 to be the messages to be displayed.

If the bacteria meter calculated at S103 is 20(%) or higher and the season information is identified to be the summer season, determining unit 207 determines that the condition for determining a message is condition 7-2 at S112 regardless of the humidity, and from the correspondence relation shown in FIG. 35, determines the message "WATCH OUT FOR SUMMER COLD" corresponding to condition 7-2 to be the message to be displayed.

Figures 42A, 42B:
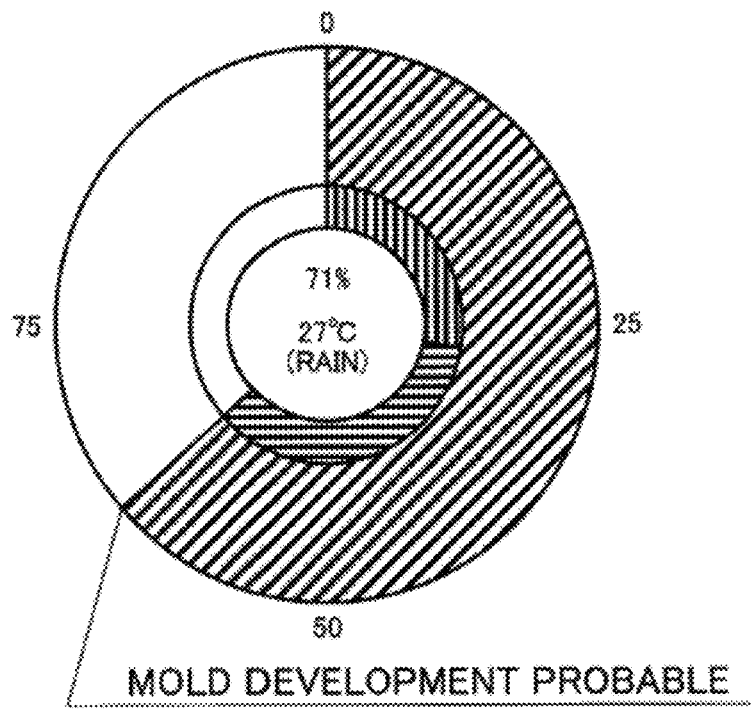
FIG. 42A shows a specific example of display.
FIG. 42B shows a specific example of displayed messages.

If the condition is 7-1, at S113, generating unit 203 generates display data for displaying the determined messages "MOLD DEVELOPMENT PROBABLE" and "WATCH OUT FOR SUMMER COLD" near the boundary between the pollution meter and the clean meter displayed as results of detection as shown in FIGS. 42A and 42B. At S115, output unit 204 outputs the display data as such to display panel 130 and by such display control, the images of FIGS. 42A and 42B are displayed on display panel 130. Similarly, if the condition is 7-2, display data for displaying the determined message "WATCH OUT FOR SUMMER COLD" near the boundary between the pollution meter and the clean meter is generated.

From the conditions shown in FIG. 34, if the bacteria meter calculated at S103 is 20(%) or higher and humidity is lower than 40%, determining unit 207 determines that the condition for determining a message is condition 8 at S112, and from the correspondence relation shown in FIG. 35, determines the messages "TAKE CARE TO PREVENT DRY THROAT" and "WATCH OUT FOR COLD" corresponding to condition 8 to be the messages to be displayed.

If the condition is 8, at S113, generating unit 203 generates display data for displaying the determined messages "TAKE CARE TO PREVENT DRY THROAT" and "WATCH OUT FOR COLD" near the boundary between the pollution meter and the clean meter displayed as results of detection as shown in FIGS. 43A and 43B. At S115, output unit 204 outputs the display data as such to display panel 130 and by such display control, the images of FIGS. 43A and 43B are displayed on display panel 130. In the condition determination described above, if the humidity is 60% or higher and the season is rainy season, determining unit 207 may specify condition 2 or condition 3-1 or 3-2, if other conditions (room temperature, weather and the like) are satisfied, other than condition 4, as the condition for determining the message. In this case also, one condition is determined in accordance with the priority set beforehand. As described above, the priority is higher if the condition can be an environmental factor of higher risk. More preferably, the time of year is given higher priority and if a condition is specified by the time of year, the condition for determining the message is determined, with the condition related to the time of year given higher priority. In the example above, of the specified conditions 2, 3-1, 3-2 and 4, the condition 4 determined by the season is determined to be the condition for determining the message.

Similarly, if humidity is 40% or lower, at S112, determining unit 207 may specify conditions 6-1 or 6-2 if other condition or conditions (season) are satisfied, in addition to condition 8. Here again, in accordance with the priority, with the time of year given higher priority, control unit 270 determines condition 6-1 or 6-2 as the condition for determining the message.

From the conditions shown in FIG. 34, if the bacteria meter calculated at S103 is lower than 20(%) and humidity is lower than 40%, determining unit 207 determines that the condition for determining a message is condition 9 at S112, and from the correspondence relation shown in FIG. 35, determines the message "TAKE CARE TO PREVENT DRY THROAT" corresponding to condition 9 to be the message to be displayed.

Figure 44:
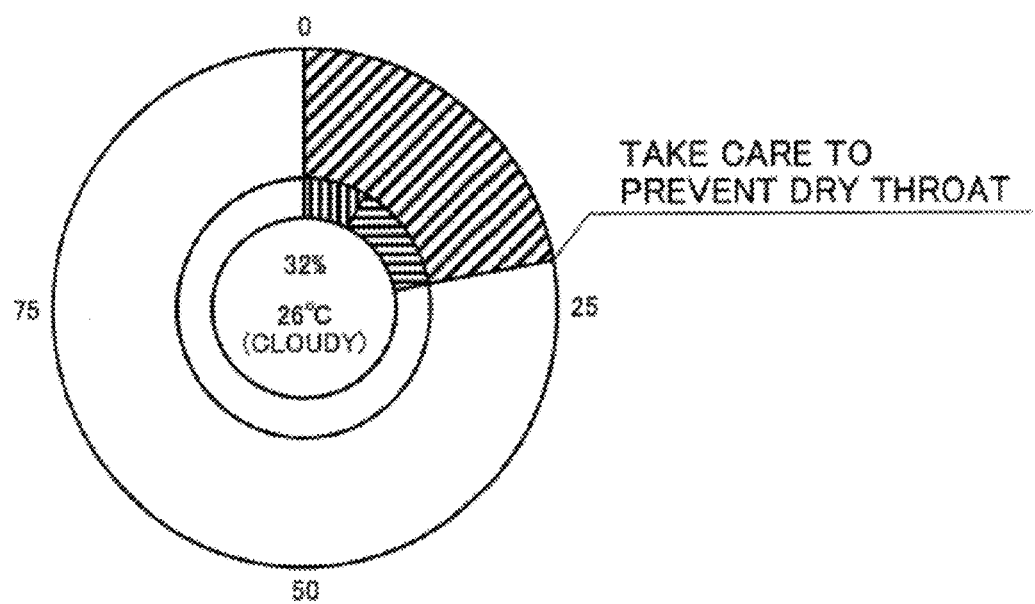
FIG. 44 shows a specific example of display.

If the condition is 9, at S113, generating unit 203 generates display data for displaying the determined message "TAKE CARE TO PREVENT DRY THROAT" near the boundary between the pollution meter and the clean meter displayed as results of detection as shown in FIG. 44. At S115, output unit 204 outputs the display data as such to display panel 130 and by such display control, the image of FIG. 44 is displayed on display panel 130.

From the conditions shown in FIG. 34, if the bacteria meter calculated at S103 is lower than 20(%), room temperature is 20° C. or higher and humidity is 80% or higher, determining unit 207 determines that the condition for determining a message is condition 10 at S112, and from the correspondence relation shown in FIG. 35, determines the message "MOLD DEVELOPMENT PROBABLE" corresponding to condition 10 to be the message to be displayed.

Figures 45A, 45B:
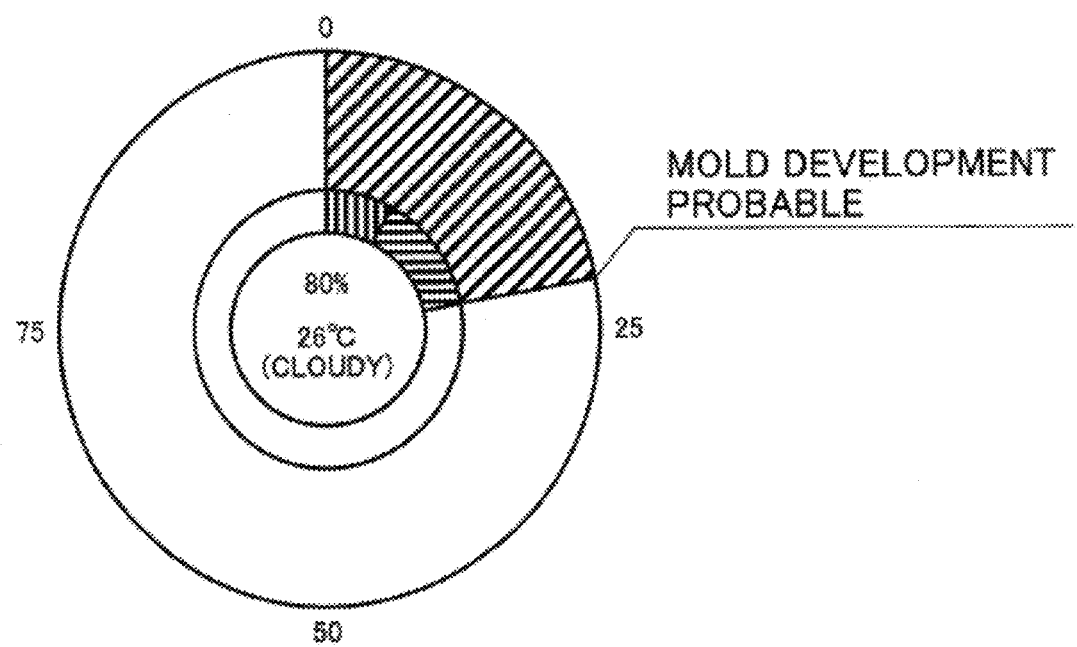
FIG. 45A shows a specific example of display.
FIG. 45B shows a specific example of displayed messages.

If the condition is 10, generating unit 203 generates display data for displaying the determined message "MOLD DEVELOPMENT PROBABLE" near the boundary between the pollution meter and the clean meter displayed as results of detection as shown in FIG. 45A. At S115, output unit 204 outputs the display data as such to display panel 130 and by such display control, the image of FIG. 45A is displayed on display panel 130.

FIG. 35 shows an example in which only the message "MOLD DEVELOPMENT PROBABLE" is shown as corresponding to condition 10. However, a plurality of messages may be prepared to correspond to condition 10. By way of example, assume that a plurality of messages including "MOLD DEVELOPMENT PROBABLE" and "DEHUMIDIFY/REMOVE BACTERIA" are stored. In that case, the plurality of messages may be displayed side by side as shown in FIG. 45B or may be displayed one by one (in rotation) at a prescribed time interval, on the area for displaying messages on the screen image.

From the conditions shown in FIG. 34, if the bacteria meter calculated at S103 is lower than 20(%), humidity is lower than 40% and the season information is identified to be the season of cold infection, determining unit 207 determines that the condition for determining a message is condition 11-1 at S112, and from the correspondence relation shown in FIG. 35, determines the message "WATCH OUT FOR . . . COLD" corresponding to condition 11-1 to be the message to be displayed.

If the bacteria meter calculated at S103 is lower than 20(%), humidity is lower than 40% and the season information is identified to be the winter season, determining unit 207 determines that the condition for determining a message is condition 11-2 at S112, and from the correspondence relation shown in FIG. 35, determines the message "WATCH OUT FOR FLU" corresponding to condition 11-2 to be the message to be displayed.

Figures 46A, 46B:
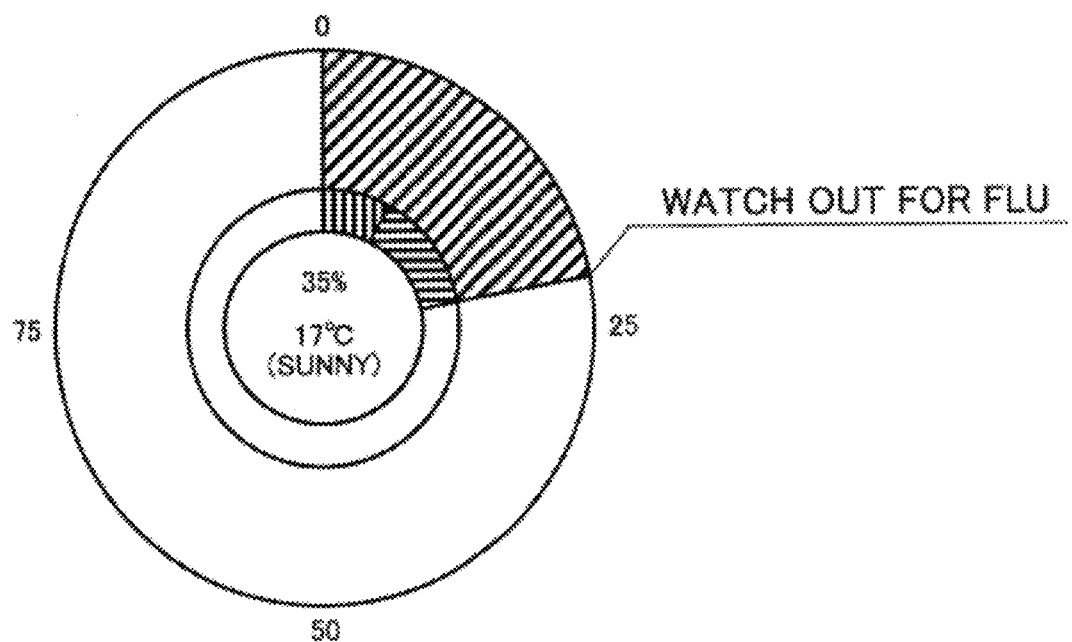
FIG. 46A shows a specific example of display.
FIG. 46B shows a specific example of displayed messages.

If the condition is 11-2, at S113, generating unit 203 generates display data for displaying the determined message "WATCH OUT FOR FLU" near the boundary between the pollution meter and the clean meter displayed as results of detection as shown in FIG. 46A. At S115, output unit 204 outputs the display data as such to display panel 130 and by such display control, the image of FIG. 46A is displayed on display panel 130. Similarly, if the condition is 11-1, display data for displaying the message "WATCH OUT FOR . . . COLD" near the boundary between the pollution meter and the clean meter is generated.

FIG. 35 shows an example in which only the message "WATCH OUT FOR FLU" is shown as corresponding to condition 11-2. However, a plurality of messages may be prepared to correspond to condition 11-2. By way of example, assume that a plurality of messages including "WATCH OUT FOR FLU" and "WASH YOUR HANDS AND GARGLE" are stored. In that case, the plurality of messages may be displayed side by side as shown in FIG. 46B or may be displayed one by one (in rotation) at a prescribed time interval, on the area for displaying messages on the screen image.

From the conditions shown in FIG. 34, if the bacteria meter calculated at S103 is lower than 20(%) and pollution meter is 11 to 20, determining unit 207 determines that the condition for determining a message is condition 12-1 at S112, and from the correspondence relation shown in FIG. 35, determines the message "CLEAN ENVIRONMENT" corresponding to condition 12-1 to be the message to be displayed.

If the bacteria meter calculated at S103 is lower than 20(%), pollution meter is lower than 10 and humidity is 40% to 60%, determining unit 207 determines that the condition for determining a message is condition 12-2 at S112, and from the correspondence relation shown in FIG. 35, determines the message "VERY CLEAN ENVIRONMENT" corresponding to condition 12-2 to be the message to be displayed.

Figure 47A:
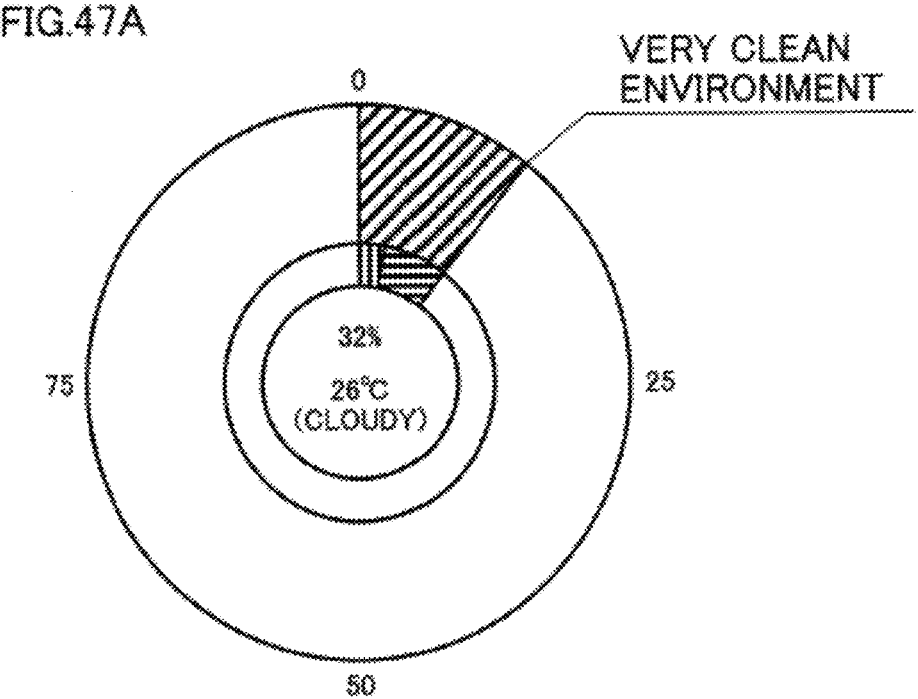
FIG. 47A shows a specific example of display.
Figure 47B:
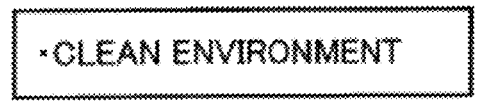
FIG. 47B shows a specific example of a displayed message.

If the condition is 12-2, at S113, generating unit 203 generates display data for displaying the determined message "VERY CLEAN ENVIRONMENT" near the boundary between the pollution meter and the clean meter displayed as results of detection as shown in FIG. 47A. At S115, output unit 204 outputs the display data as such to display panel 130 and by such display control, the image of FIG. 47A is displayed on display panel 130.

Similarly, if the condition is 12-1, display data for displaying the message "CLEAN ENVIRONMENT" near the boundary between the pollution meter and the clean meter is generated.

In the condition determination described above, if the humidity is lower than 40%, at S112, determining unit 207 may specify conditions 11-1 or 11-2 if other condition or conditions (season) are satisfied, in addition to condition 9. Here again, in accordance with the priority, with the time of year given higher priority, control unit 270 determines condition 11-1 or 11-2 as the condition for determining the message.

Modification 1 of the Second Example of Display Control

In the example described above, both the microorganisms and dust particles are detected by detection apparatus 100 and the total sum of these is used as the pollution meter. What is necessary is that at least the microorganisms are detected. In that case, the bacteria meter corresponds to the pollution meter. Such detection can also serve to determine environmental status with high accuracy and realize appropriate message display. Therefore, the user can grasp the environmental status and take necessary measure.

Figure 48:
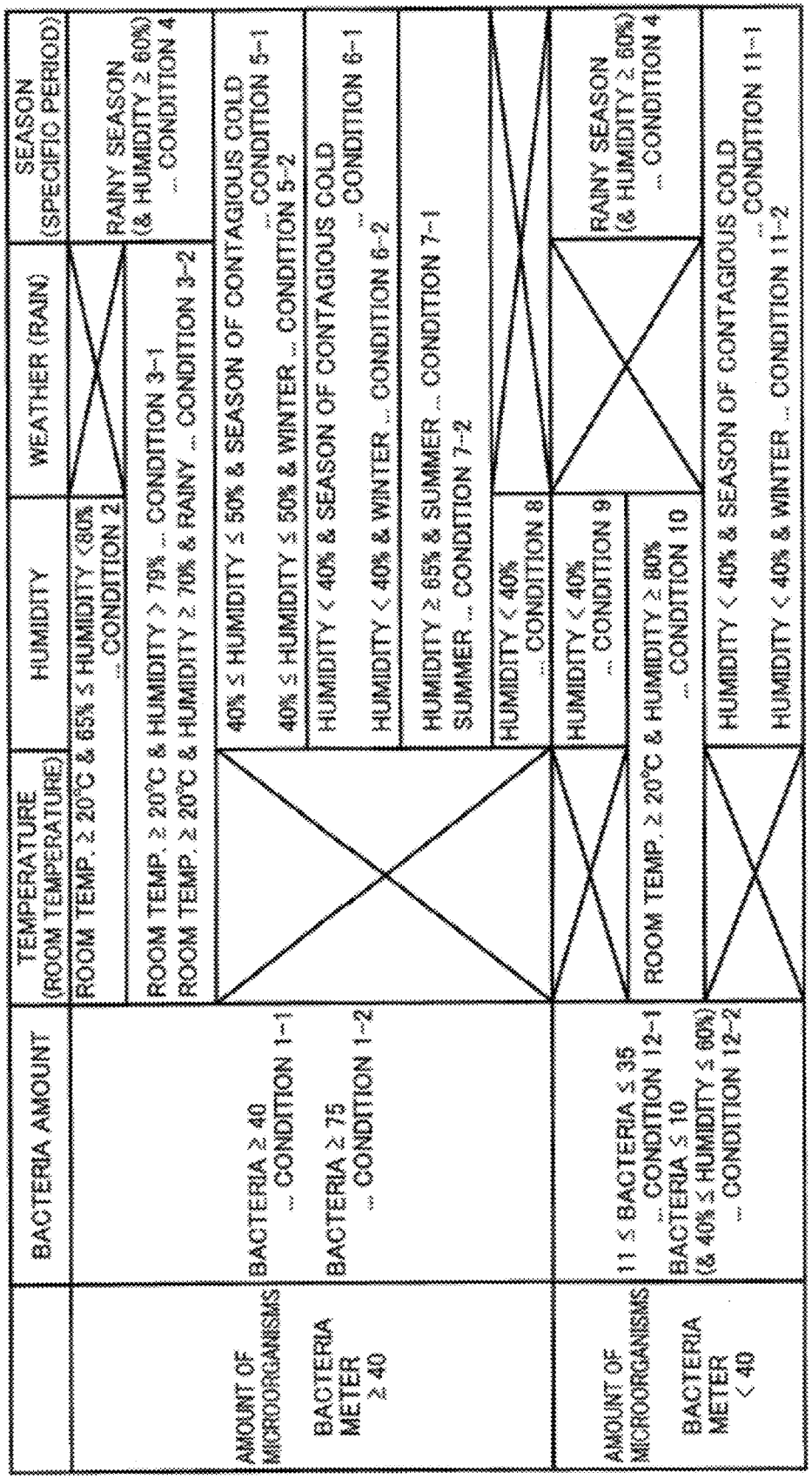
FIG. 48 shows specific examples of conditions for determining messages in accordance with Modification 1 of the display control of the second example.

As Modification 1 of the second example of display control, an example in which dust particles are not detected but only microorganisms are detected by detection apparatus 100 will be described. As the conditions for this approach, conditions shown in FIG. 48 are stored in condition storage unit 206, and messages are prepared in correspondence with the conditions as shown in FIG. 35. Display in this situation will be described with reference to specific examples. Specific numerical values of conditional equations in FIG. 48 are examples only, and not limiting.

From the conditions shown in FIG. 48, if the bacteria meter calculated at S103 is 40(%) or higher, that is, if the pollution meter is 40 or higher, determining unit 207 determines that the condition for determining a message is condition 1-1 at S112, and from the correspondence relation shown in FIG. 35, determines the message "ROOM AIR POLLUTED" corresponding to condition 1-1 to be the message to be displayed. Here, it is the case that much microorganisms floating in the air is detected and, therefore, a message such as "BACTERIA FLOATING" indicating many microorganisms is preferably prepared correspondingly.

Figures 49A, 49B, 49C:
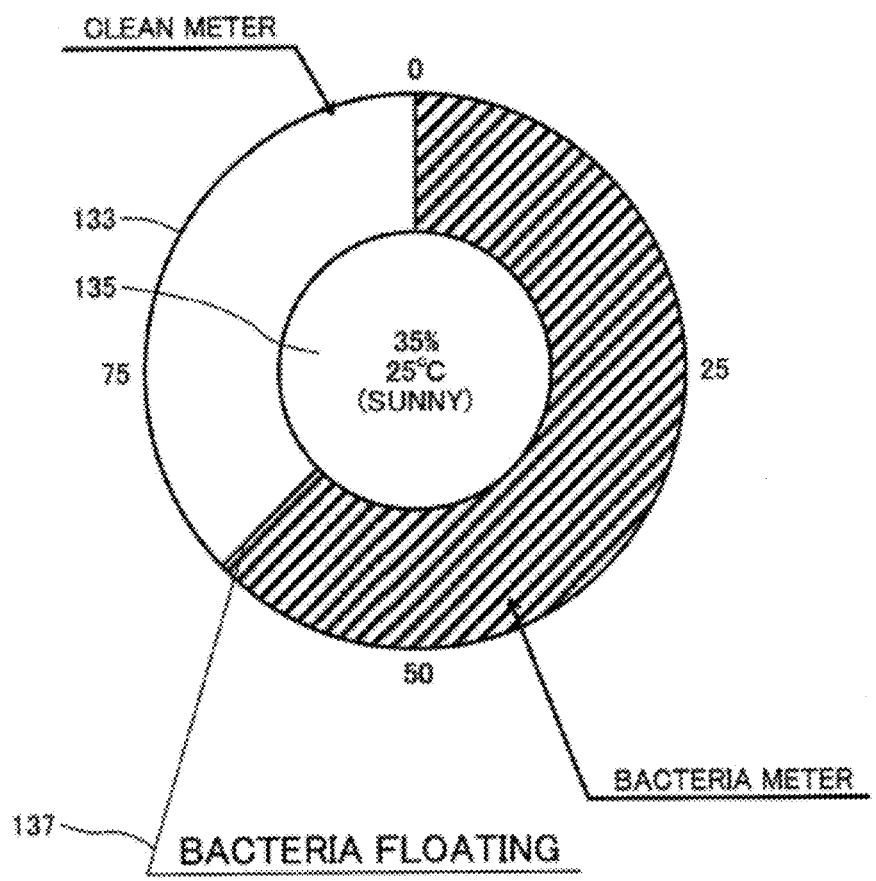
FIG. 49A shows a specific example of display in accordance with Modification 1 of the display control of the second example.
FIG. 49B shows a specific example of displayed messages.
FIG. 49C shows a specific example of displayed messages.

If the condition is 1-1, at S113, generating unit 203 generates display data for displaying the determined message "BACTERIA FLOATING" near the boundary between the pollution meter and the clean meter displayed as results of detection as shown in FIG. 49A. At S115, output unit 204 outputs the display data as such to display panel 130 and by such display control, the image of FIG. 49A is displayed on display panel 130.

A plurality of messages may be prepared to correspond to condition 1-1. By way of example, assume that a plurality of messages including "BACTERIA FLOATING", "RUN ION GENERATOR" and "RUN AIR PURIFIER" are stored. In that case, the plurality of messages may be displayed side by side as shown in FIG. 49B or may be displayed one by one (in rotation) at a prescribed time interval, on the area for displaying messages on the screen image.

From the conditions shown in FIG. 48, if the bacteria meter calculated at S103 is 40(%) or higher, humidity is higher than 79% and the room temperature is 20° C. or higher, determining unit 207 determines that the condition for determining a message is condition 3-1 at S112, and from the correspondence relation shown in FIG. 35, determines the message "RISK OF MOLD DEVELOPMENT ELEVATED" corresponding to condition 3-1 to be the message to be displayed.

Similarly, if the bacteria meter calculated at S103 is 40(%) or higher, humidity is 70% or higher, the room temperature is 20° C. or higher and the weather is rainy, determining unit 207 determines that the condition for determining a message is condition 3-2 at S112, and from the correspondence relation shown in FIG. 35, determines the message "RISK OF MOLD DEVELOPMENT ELEVATED" corresponding to condition 3-2 to be the message to be displayed.

If the condition is 3-1 or 3-2, at S113, generating unit 203 generates display data for displaying the determined message "RISK OF MOLD DEVELOPMENT ELEVATED" near the boundary between the pollution meter and the clean meter displayed as results of detection as shown in FIG. 50A. At S115, output unit 204 outputs the display data as such to display panel 130 and by such display control, the image of FIG. 50A is displayed on display panel 130.

A plurality of messages may be prepared to correspond to conditions 3-1 and 3-2. By way of example, assume that a plurality of messages including "RISK OF MOLD DEVELOPMENT ELEVATED" and "DEHUMIDIFY/REMOVE BACTERIA" are stored. In that case, the plurality of messages may be displayed side by side as shown in FIG. 50B or may be displayed one by one (in rotation) at a prescribed time interval, on the area for displaying messages on the screen image.

Modification 2 of the Second Example of Display Control

In the examples described above, the state of air at present is displayed as the results of detection by detection apparatus 100 and as the message. As another example, the state may be compared with previous state of the air and the result of comparison may be displayed.

Figure 51:
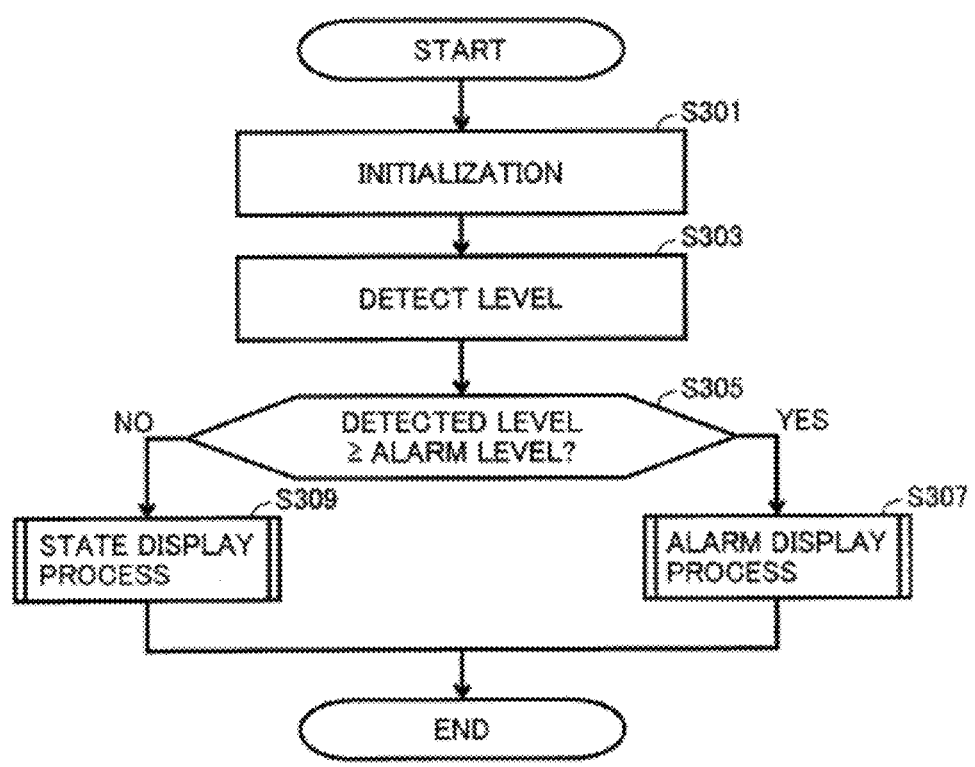
FIG. 51 is a flowchart showing a specific example of control flow in the display control unit in accordance with Modification 2 of the display control of the second example.

FIG. 51 is a flowchart representing the flow of Modification 2 of the display control in accordance with the second example. The process shown in the flowchart of FIG. 51 is realized by a CPU, not shown, included in control device 200 reading and executing programs stored in the memory to invoke various functions shown in FIG. 32.

Referring to FIG. 51, at 5301, display control unit 210 performs initial setting. Here, the initial setting may include setting of levels of pollution degree represented as relative values of the total sum of the amount of microorganisms and dust particles in the subsequent processes in the similar manner as described above. Further, the initial setting may include setting of time interval for detecting the state of air, and setting of the level for giving an alarm (hereinafter also referred to as alarm level) in the subsequent processes.

At S303, detected value input unit 201 receives input of the results of detection from detection apparatus 100, and computing unit 202 calculates the relative values of the microorganisms with respect to the "total value" of microorganisms and the relative value of dust particles with respect to the "total value" of dust, and a level corresponding to the total sum is identified, whereby the level is detected. Specifically, computing unit 202 stores beforehand the correspondence relation between the relative values and levels, such as the sum of relative values of microorganisms and dust particles up to 30% corresponds to "Level 0", 30% to 40% corresponds to "Level 1", 40% to 50% corresponds to "Level 2", 50% to 60% corresponds to "Level 3", 60% to 70% corresponds to "Level 4" and 70% and higher corresponds to "Level 5" and, by identifying the level corresponding to the calculated relative values, it can detect the level.

At S305, determining unit 207 compares the set alarm level with the detected level. As a result, if the detected level is higher than the alarm level (YES at S305), generating unit 203 reads display data for displaying an alarm message stored in advance, and passes the data to output unit 204. Thus, the process for display takes place at output unit 204, and the alarm message is displayed. The alarm message here may be the same as that in accordance with the first example of display control.

On the other hand, if the detected level is found to be not reaching the alarm level as a result of comparison at S305 (NO at S305), display control unit 210 may end the process without executing the process for displaying the alarm at step S307. Preferably, however, at S309, a process for comparing the detected level with previous level and displaying the status in accordance with the result of comparison is executed. Specifically, determining unit 207 stores the level detected at computing unit 202, and at S309, compares the level detected and stored previously with the level detected at S303. As a result, if the detected level is lower than the previous level, it is determined that the air state has been improved, and the process for improved state is executed. If the detected level is higher than the previous level, it is determined that the air state worsened, and the process for worsened state is executed. If the detected level is the same as the previous level, it is determined that the air state is maintained, and the process for maintained state is executed. Correspondence between the detected levels and messages used for respective processes are stored as conditions in condition storage unit 206.

FIG. 52 shows specific examples of the correspondence between detected levels and messages for the process when the state has been improved. When the process for improved state is to be executed, generating unit 203 refers to the correspondence shown in FIG. 52, reads the display data for displaying the message corresponding to the detected level, and passes the data to output unit 204. Thus, the process for display is executed at output unit 204, and the message corresponding to the detected level of improved state is displayed.

FIG. 53 shows specific examples of the correspondence between detected levels and messages for the process when the state has been worsened. When the process for worsened state is to be executed, generating unit 203 refers to the correspondence shown in FIG. 53, reads the display data for displaying the message corresponding to the detected level, and passes the data to output unit 204. Thus, the process for display is executed at output unit 204, and the message corresponding to the detected level of worsened state is displayed.

Figures 54, 55:
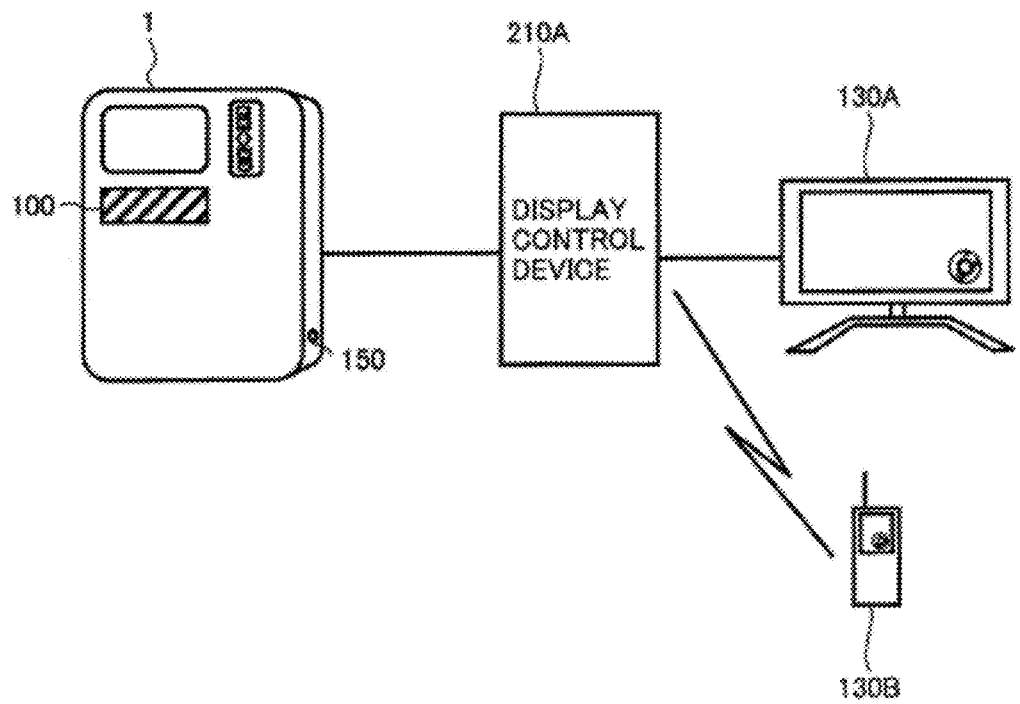
FIG. 54 shows specific examples of correspondence between messages and conditions for determining messages in accordance with Modification 2 of the display control of the second example.
FIG. 55 shows a specific example of a configuration of the display system in accordance with Modification 1.

FIG. 54 shows specific examples of the correspondence between detected levels and messages for the process when the state has been maintained. When the process for maintained state is to be executed, generating unit 203 refers to the correspondence shown in FIG. 54, reads the display data for displaying the message corresponding to the detected level, and passes the data to output unit 204. Thus, the process for display is executed at output unit 204, and the message corresponding to the detected level of maintained state is displayed.

Modification 1

The function of air purifier 1 shown in FIG. 1B may be realized by a plurality of devices. As a modification, the configuration shown in FIG. 55 realizing the functions shown in FIG. 1B will be described. Referring to FIG. 55, in the display system in accordance with the modification, a display control device 210A corresponding to display control unit 210 is connected to air purifier 1 including detection apparatus 100. Display control device 210A has the results of detection by detection apparatus 100 (or results of detection and message) displayed on a television receiver (hereinafter denoted as TV) 130A or on a portable telephone 130B as a display device.

The functional configuration of display control device 210A of the modification is similar to the functional configuration of display control unit 210 shown in FIGS. 27 and 32. It is noted, however, that in display control device 210A, detected value input unit 201 communicates with output unit 43 of detection apparatus 100 to receive the results of detection. Further, output unit 204 outputs display data to TV 130A or portable telephone 130B in place of (or in addition to) display panel 130. An application (program) for displaying the results of detection is stored in advance in TV 130A and portable telephone 130B. When the display data is received from display control device 210A, a CPU, not shown, activates the application and causes these display devices to display the results of detection (or results of detection and message).

Further, output unit 204 of display control device 210A stores the information of output destination and other conditions related to output in advance, and outputs the display data to the output destination stored in advance in accordance with the conditions, at prescribed timing. The conditions related to output may include, for example, priority as the output destination when a plurality of different types of output destinations are stored. When a plurality of output destinations of the same type are stored, for example, when a plurality of TVs are stored as TVs 130A, or when a plurality of portable telephones are stored as portable telephones 130B, the condition may include the priority as to which of these is to be used as the output destination.

Figure 56:
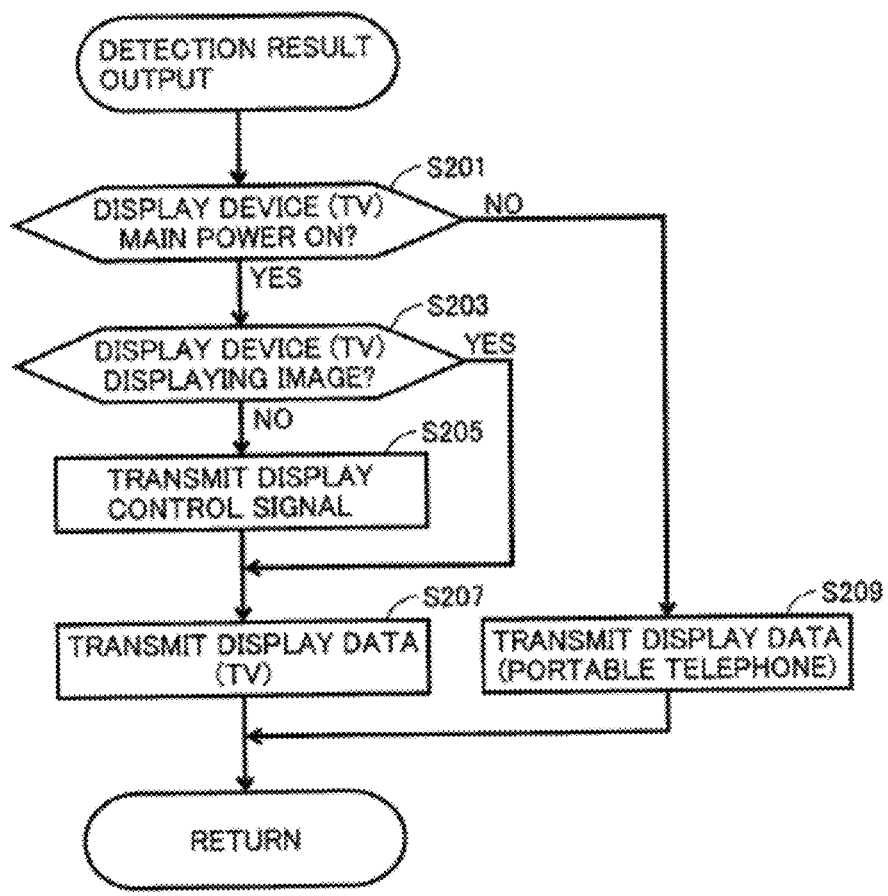
FIG. 56 is a flowchart representing a specific example of the process flow for outputting display data from the display control device to the display device, in the display system in accordance with Modification 1.

In display control device 210A, the process similar to the process shown in the flowchart of FIG. 28 or FIG. 33 is executed. It is noted, however, that in display control device 210A, in the process for outputting the display data of S115, the process such as shown in FIG. 56 is executed. FIG. 56 shows a process executed when, of TV 130A and portable telephone 130B as the output devices, higher priority as the output destination is set for TV 130A.

Referring to FIG. 56, before outputting the display data, output unit 204 determines whether or not the main power of TV 130A is ON or OFF. The method of determination is not specifically limited. By way of example, a predetermined response request is output to TV 130A and if there is no response, it is determined that the main power is OFF.

If it is determined that the main power of TV 130A is ON (YES at S201), it is expected that the user is near TV 130A. Therefore, output unit 204 further determines whether or not TV 130A is currently displaying any image. The method similar to the above may be used for determination. If TV 130A is not displaying any image (NO at S203), at S205, output unit 204 transmits a predetermined control signal for starting display on TV 130A before outputting the display data and, at S207, outputs the display data generated at S113 to TV 130A. If TV 130A is displaying any image (YES at S203), the display data is output to TV 130A at S207, without transmitting the control signal.

If it is determined that the main power of TV 130A is OFF (NO at S201), it is expected that the user is away from TV 130A. Therefore, at S207, output unit 204 outputs the display data generated at S113 to portable telephone 130B stored as the output destination of second highest priority. The output here may use a method of writing the display data in a mail format stored in advance and sending the mail.

Since the display data is output in this manner, for the user supposed to be near TV 130A, the results of detection (or the results of detection and message) are displayed on the screen of TV 130A. Further, for a user not supposed to be near TV 130A, the results of detection (or the results of detection and message) are displayed not on the screen of TV 130A but on a screen of portable telephone 130B. As to the method of display, a circle graph such as FIG. 10 or a message may be displayed superposed on a broadcast program, or the graph or message may be displayed on a display area different from the broadcast program.

Figures 57, 58:
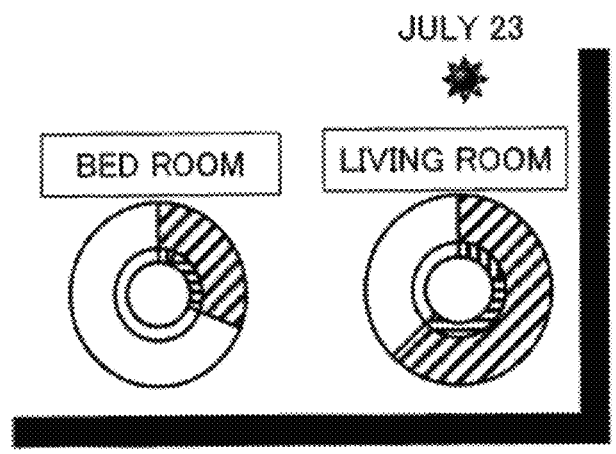
FIG. 57 shows a specific example of display in the display system in accordance with Modification 1.
FIG. 58 shows specific examples of correspondence between messages and conditions for determining messages in accordance with Modification 2.

Further, a plurality of air purifiers may be connected to display control device 210A, and the results of detection (or the results of detection and message) from the detection apparatus mounted in each air purifier may be displayed on TV 130A or portable telephone 130B as the display device. In such a case, display control device 210A stores in advance identification information allowing identification of each detection apparatus, and outputs the identification information in relation with the display device to TV 130A or portable telephone 130B. TV 130A or portable telephone 130B also stores in advance identification information allowing identification of each detection apparatus, and based on the identification information related to the display data, displays the results of detection of each detection apparatus (air purifier). FIG. 57 shows an example of display on TV 130A in that case, showing examples when display is controlled in accordance with the first example of display control. Preferably, TV 130A stores correspondence between the pieces of identification information and the air purifiers in advance, and displays, together with the circle graph or message representing the results of detection, the information indicating the air purifier (in the example of FIG. 57, the place of installment).

By the display in accordance with the modification, it becomes possible to grasp the information presented in unified manner including information related to the ratio of microorganisms and dust particles in the air as a whole and the information related to humidity, temperature, weather or season, as well as the message related to the environmental status determined generally using such information, even at a location away from detection apparatus 100.

Modification 2

In the example above, it is assumed that display control unit 210 outputs the results of detection by detection apparatus 100 or the results of detection and the message to the display device. The output, however, is not limited to display, and it may be given in a different manner. Specific examples may include voice, music, light (color, manner of flickering and the like), vibration, and a combination of these. Here, control device 200 of air purifier 1 includes an output control unit in accordance with the manner of output in place of display control unit 210, and the output control unit executes a process for outputting the results of detection by detection apparatus 100 or the results of detection and the message by voice, music, light, vibration, or a combination of these.

By way of example, let us consider the process (the process for improved state, the process for worsened state, the process for maintained state) when the detected level does not reach the alarm level in Modification 2 of the second example of display control. In place of displaying the message as described above, if the message is to be presented by sound or light (color or manner of flickering), correspondences shown in FIGS. 58 to 60 are stored in condition storage unit 206 in place of correspondences shown in FIGS. 52 to 54. The output control unit that is provided in place of display control unit 210 controls the output such that the output is given in the manner corresponding to the detected level, referring to the correspondence.

Further, it is also possible to provide a program for causing a computer to execute the process of display control unit 210 or display control device 210A. Such a program may be recorded on a computer readable recording medium such as a flexible disk, CD-ROM (Compact Disk-Read Only Memory), an ROM (Read Only Memory), an RAM (Random Access Memory) or a memory card attached to the computer, and provided as a program product. Alternatively, the program may be provided recorded on a recording medium such as a hard disk mounted inside the computer. Further, the program may be provided by downloading through a network.

The program may be realized by calling and executing, from program modules provided as part of the operating system (OS) of a computer, necessary modules at prescribed timing in a prescribed sequence. In that case, the modules themselves are not included in the program itself, and the process is executed in cooperation with the OS.

Further, the program may be provided incorporated in a part of another program. In that case also, the program itself does not include any module included in said another program, and the process is executed in cooperation with said another program.

The provided program product is executed, installed in a program storage unit such as the hard disk. The program product includes the program itself and the recording medium on which the program is recorded.

Although the present invention has been described and illustrated in detail, it is clearly understood that the same is by way of illustration and example only and is not to be taken by way of limitation, the scope of the present invention being interpreted by the terms of the appended claims.

REFERENCE SIGNS LIST 1 air purifier, 2 high voltage power source, 3 coating, 4 support board, 5 case, 5A collection chamber, 5B detection chamber, 5C wall, 5C' hole, 6 light emitting element, 7 lens, 8 collecting lens, 9 light receiving element, 10 inlet, 10A, 11A light shielding portion, 10a, 10b light shielding plate, 11 outlet, 12 collecting jig, 12A collection unit, 13 aperture, 14 filter, 15 irradiation region, 16A, 16B shutter, 17 discharge electrode, 20 sensor, 30 signal processing unit, 31 filter circuit, 32 pulse width measuring circuit, 33, 34 voltage converting circuit, 35 amplifier circuit, 36 voltage comparing circuit, 40 detecting unit, 41 calculating unit, 42 storage unit, 43, 204 output unit, 44 input unit, 46 external connection unit, 47 clock generating unit, 48 driving unit, 49 control unit, 50 introducing mechanism, 50A fan, 60 brush, 65A cover, 65B adaptor, 91 heater, 100, 100A, 100B, 100C detection apparatus, 110 switch, 130 display panel, 130A TV, 130B portable telephone, 150 communication unit, 200 control device, 201 detected value input unit, 202 computing unit, 203 generating unit, 205 environmental value input unit, 206 condition storage unit, 207 determining unit, 210 display control unit, 210A display control device, 220 detection control unit.

The invention claimed is:

1. A display control device, causing a display device to give a display based on result of detection related to amount of microorganisms by a detection apparatus comprising:
a first input unit for receiving an input of detection result related to amount of microorganisms in the air from said detection apparatus; and
a computing device; wherein
said computing device stores a predetermined amount as the amount of microorganisms as a reference for determining air pollution, and
said computing device executes
a computing process for obtaining a relative value of the amount of microorganisms detected by said detection apparatus with respect to said predetermined amount of microorganisms, and
a display process for causing said display device to give a first display representing the amount of microorganisms detected by said detection apparatus in an area corresponding to said relative value, in a first display area representing said predetermined amount of microorganisms, wherein said detection apparatus includes
a light emitting element,
a light receiving element having a light receiving direction at a prescribed angle to direction of irradiation of said light emitting element, and
a processing device for processing amount of light received by said light receiving element as a detection signal; and
said processing device includes
an input unit for receiving an input of the amount of light received by said light receiving element as a detection signal, and
a storage unit, and executes
a process for comparing said detection signal with an arbitrary condition, for determining whether or not detected object is a microorganism, and
a process for writing result of said determination in said storage unit.

2. The display control unit according to claim 1, wherein said first input unit includes a communication unit for communication with said detection apparatus; and
said computing device includes a communication unit for communication with said display device.

3. The display control device according to claim 1, wherein said first input unit further receives input of result of detection of amount of particles other than microorganisms in the air from said detection apparatus;
said computing device further executes a computing process for obtaining relative value of the amount of particles detected by said detection apparatus with respect to a predetermined amount of said particles other than microorganisms; and
in said first display, a total sum of the predetermined amount of said microorganisms and the predetermined amount of said particles other than microorganisms is represented in said first display area, and said amount of particles is represented in an area corresponding to the relative value of said amount of particles other than microorganisms in said first display area.

4. The display control device according to claim 3, wherein said computing device causes said display device, by said display process, to give a second display representing amount of particles in the air in an area corresponding to relative values of said microorganisms and said particles other than microorganisms in a second display area representing total sum of said predetermined amounts, together with said first display.

5. The display control device according to claim 1, further comprising
a second input unit for receiving an input of information related to environment from another device; and
said computing device causes said display device, by said display process, to give a third display representing said information related to environment, together with said first display.

6. The display control device according to claim 1, wherein said detection apparatus includes
the light receiving element for receiving fluorescence;
a calculating unit for calculating, based on change in amount of fluorescence, caused by irradiation of air introduced to said detection apparatus by said light emitting element, received by said light receiving element before and after heating of said air introduced to said detection apparatus, amount of microorganisms in said introduced air, and
an output unit for outputting result of said calculation as result of detection of said amount of microorganisms to said display control device.

7. A display control device causing a display device to give a display based on result of detection related to amount of microorganisms by a detection apparatus, comprising:

a first input unit for receiving an input of detection result related to amount of microorganisms in the air from said detection apparatus; and a computing device; wherein said computing device includes a storage unit for storing a plurality of messages of different types in relation to result of detection by said detection apparatus, and said computing device executes a process for determining a message to be displayed from the plurality of messages of different types at least based on the detection result received by said first input unit, and a process for generating display data causing said display device to display an image including said determined message, wherein said detection apparatus includes a light emitting element, a light receiving element having a light receiving direction at a prescribed angle to direction of irradiation of said light emitting element, and a processing device for processing amount of light received by said light receiving element as a detection signal; and said processing device includes an input unit for receiving an input of the amount of light received by said light receiving element as a detection signal, and a storage unit, and executes a process for comparing said detection signal with an arbitrary condition, for determining whether or not detected object is a microorganism, and a process for writing result of said determination in said storage unit.

8. The display control device according to claim 7, wherein said first input unit includes a communication unit for communication with said detection apparatus; and said computing device includes a communication unit for communication with said display device.

9. The display control device according to claim 7, further comprising a second input unit for receiving an input of information related to environment from another device; and in said process for determining a message to be displayed, said computing device determines a message to be displayed based on the detection result received by said first input unit and on the value received by said second input unit.

10. The display control device according to claim 7, wherein said image includes said message and said detection result received by said first input unit.

11. The display control device according to claim 7, wherein said first input unit further receives input of detection result of amount of particles other than microorganism in the air from said detection apparatus.

12. The display control device according to claim 7, wherein said detection apparatus includes the light receiving element for receiving fluorescence;

a calculating unit for calculating, based on change in amount of fluorescence, caused by irradiation of air introduced to said detection apparatus by said light emitting element, received by said light receiving element before and after heating of said air introduced to said detection apparatus, amount of microorganisms in said introduced air, and an output unit for outputting result of said calculation as result of detection of said amount of microorganisms to said display control device.

\* \* \* \* \*